(12) United States Patent
Bala et al.

(10) Patent No.: US 9,403,810 B2
(45) Date of Patent: Aug. 2, 2016

(54) CARBOXAMIDE DERIVATIVES

(71) Applicant: Novartis AG, Basel (CH)

(72) Inventors: Kamlesh Jagdis Bala, Horsham (GB); Andrew Brearley, Oxfordshire (GB); James Dale, New Market (GB); Anne-Marie Edwards, Surrey (GB); Mahbub Ahmed, Horsham (GB); David Porter, Horsham (GB); Robert Alexander Pulz, Basel (CH); Lisa Ann Rooney, Surrey (GB); David Andrew Sandham, Horsham (GB); Duncan Shaw, Sharon, MA (US); Nichola Smith, Horsham (GB); Jessica Louise Taylor, Surrey (GB); Roger John Taylor, Southwater (GB); Thomas Josef Troxler, Wahlen b. Laufen (CH); Joe Wrigglesworth, Notts (GB)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/711,684

(22) Filed: May 13, 2015

(65) Prior Publication Data
US 2015/0329529 A1 Nov. 19, 2015

(30) Foreign Application Priority Data

May 14, 2014 (EP) .................................. 14168303

(51) Int. Cl.
*C07D 413/12* (2006.01)
*C07D 413/14* (2006.01)
*A61K 31/4155* (2006.01)
*A61K 31/422* (2006.01)

(52) U.S. Cl.
CPC .......... *C07D 413/12* (2013.01); *A61K 31/4155* (2013.01); *A61K 31/422* (2013.01); *C07D 413/14* (2013.01)

(58) Field of Classification Search
None
See application file for complete search history.

(56) References Cited

U.S. PATENT DOCUMENTS

| 7,354,722 B1 | 4/2008 | Thomsen et al. |
| 2006/0223873 A1 | 10/2006 | Shaw et al. |
| 2009/0163545 A1 | 6/2009 | Goldfarb et al. |
| 2015/0329549 A1 | 11/2015 | Edwards et al. |

FOREIGN PATENT DOCUMENTS

| GB | 1696383 | 8/1981 |
| WO | 2004106306 A1 | 12/2004 |
| WO | 2005030128 A2 | 4/2005 |
| WO | 2008121861 A2 | 10/2008 |
| WO | 2009011850 A2 | 1/2009 |
| WO | 2009016241 A1 | 2/2009 |
| WO | 2011151361 A1 | 12/2011 |

OTHER PUBLICATIONS

International Search Report and Written Opinion for International Application No. PCT/US2015/030817 mailed Jun. 25, 2015. 17 pages.
Database PubChem Compound. Compound Summary for: CID 3245828. http://pubchem.ncbi.nlm.nih.gov/summary.cgi?cid=3245828. XP002729647. Published Aug. 16, 2005. Printed Nov. 9, 2014. 9 pages.
Database PubChem Compound. Compound Summary for: CID 3241509. http://pubchemncbi.nlm.nih.gov/summary/summary.cgi?cid=3241509. XP002729648. Published Aug. 16, 2005. Printed Nov. 9, 2014. 9 pages.
Database PubChem Compound. Compound Summary for: CID 3243396. http://pubchem.ncbi.nlm.nih.gov/summary/summary.cgi?cid=3243396. XP002729649. Published Aug. 16, 2005. Printed Nov. 9, 2014. 10 pages.
Database PubChem Compound. Compound Summary for: CID 9550635. http://pubchem.ncbi.nlm.nih.gov/summary/summary,cgi?cid=9550635. XP002729650. Published Oct. 20, 2006. Printed Nov. 9, 2014. 9 pages.
Database PubChem Compound. Compound Summary for: CID 9550628. http://pubchem.ncbi.nlm.nih.gov/summary/summary,cgi?cid=9550628. XP002729651. Published Oct. 20, 2006. Printed Nov. 9, 2014. 9 pages.
Database PubChem Compound. Compound Summary for: CID 3244433 http://pubchem.ncbi.nlm.nih.gov/summary/summary,cgi?cid=3244423. XP002729654. Published Aug. 16, 2005. Printed Nov. 9, 2014. 9 pages.

(Continued)

*Primary Examiner* — Samantha Shterengarts
(74) *Attorney, Agent, or Firm* — Shawn D. Britt

(57) ABSTRACT

The present invention provides a compound of formula (I) or a pharmaceutically acceptable salt thereof;

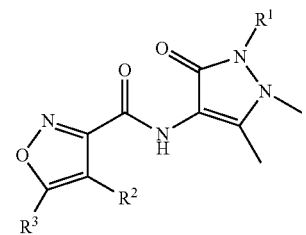

(I)

a method for manufacturing the compounds of the invention, and its therapeutic uses. The present invention further provides a combination of pharmacologically active agents and a pharmaceutical composition.

17 Claims, No Drawings

(56) References Cited

OTHER PUBLICATIONS

Database PubChem Compound. Compound Summary for: CID 1302330. http://pubchem.ncbi.nlm.nih.gov/summary/summary,cgi?cid=1302330. XP002729652. Published Jul. 11, 2005. Printed Nov. 9, 2014. 11 pages.
Database PubChem Compound. Compound Summary for: CID 9550632. http://pubchem.ncbi.nlm.nih.gov/summary/summary,cgi?cid=9550632. XP002729653. Published Oct. 20, 2006. Printed Nov. 9, 2014. 10 pages.
Database PubChem Compound. Compound Summary for: CID 9550738. http://pubchem.ncbi.nlm.nih.gov/summary/summary,cgi?cid=9550738. XP002729655. Published Oct. 20, 2006. Printed Nov. 9, 2014. 9 pages.
Database PubChem Compound. Compound Summary for: CID 3242075. http://pubchem.ncbi.nlm.nih.gov/summary/summary,cgi?cid=3242075. XP002729656. Published Aug. 16, 2005. Printed Nov. 9, 2014. 10 pages.
Database PubChem Compound. Compound Summary for: CID 9551038. http://pubchem.ncbi.nlm.nih.gov/summary/summary,cgi?cid=9551038. XP002729657. Published Oct. 20, 2006. Printed Nov. 9, 2014. 10 pages.
Database PubChem Compound. Compound Summary for: CID 3242216. http://pubchem.ncbi.nlm.nih.gov/summary/summary,cgi?cid=3242216. XP002729658 Published Aug. 16, 2005. Printed Nov. 9, 2014. 10 pages.
CAS Registry No. 898468-25-2. "3-Isoxazolecarboxamide, N-(2,3-dihydro-1,5-dimethyl-3-oxo-2-phenyl-1H-pyrazol-4-yl)-5-(4-ethoxyphenyl)—(CA Index Name)." Aug. 3, 2006.
CAS Registry No. 1015557-03-5. "3-Isoxazolecarboxamide, N-(2,3-dihydro-1,5-dimethyl-3-oxo-2-phenyl-1H-pyrazol-4-yl)-5[4-(ethylsulfonyl)phenyl]—(CA Index Name)." Apr. 18, 2008.
CAS Registry No. 912760-79-3. "3-Isoxazolecarboxamide, 5-(3-chlorophenyl)-N-(2,3-dihydro-1,5-dimethyl-3-oxo-2-phenyl-1H-pyrazol-4-yl)—(CA Index Name)." Nov. 9, 2006.
CAS Registry No. 912781-64-7. "3-Isoxazolecarboxamide, N-(2,3-dihydro-1,5-dimethyl-3-oxo-2-phenyl-1H-pyrazol-4-yl)-5-(2-hydroxyphenyl)—(CA Index Name)." Nov. 9, 2006.
CAS Registry No. 912788-96-6. "3-Isoxazolecarboxamide, N-(2,3-dihydro-1,5-dimethyl-3-oxo-2-phenyl-1H-pyrazol-4-yl)-5-(4-hydroxyphenyl)—(CA Index Name)." Nov. 9, 2006.
CAS Registry No. 912791-65-2. "3-Isoxazolecarboxamide, 5-(4-bromophenyl)-N-(2,3-dihydro-1,5-dimethyl-3-oxo-2-phenyl-1H-pyrazol-4-yl)—(CA Index Name)." Nov. 9, 2006.
CAS Registry No. 1209692-48-7. "3-Isoxazolecarboxamide, N-(2,3-dihydro-1,5-dimethyl-3-oxo-2-phenyl-1H-pyrazol-4-yl)-5-(3-pyridinyl)—(CA Index Name)." Mar. 14, 2010.
CAS Registry No. 12797-84-3. "3-Isoxazolecarboxamide, N-(2,3-dihydro-1,5-dimethyl-3-oxo-2-phenyl-1H-pyrazol-4-yl)-5-(3,4-dimethoxyphenyl)—(CA Index Name)." Nov. 9, 2006.
CAS Registry No. 898498-23-2. "3-Isoxazolecarboxamide, N-(2,3-dihydro-1,5-dimethyl-3-oxo-2-phenyl-1H-pyrazol-4-yl)-5-(3,4-dimethylphenyl)—(CA Index Name)." Aug. 3, 2006.
CAS Registry No. 717878-93-8. "3-Isoxazolecarboxamide, N-(2,3-dihydro-1,5-dimethyl-3-oxo-2-phenyl-1H-pyrazol-4-yl)-5-(4-methylphenyl)—(CA Index Name)." Jul. 28, 2004.
CAS Registry No. 1015604-48-4. "3-Isoxazolecarboxamide, N-(2,3-dihydro-1,5-dimethyl-3-oxo-2-phenyl-1H-pyrazol-4-yl)-5-(propylsulfonyl)phenyl]—(CA Index Name)." Apr. 18, 2008.
CAS Registry No. 912775-67-8. "3-Isoxazolecarboxamide, 5-(3,4-dichlorophenyl)-N-(2,3-dihydro-1,5-dimethyl-3-oxo-2-phenyl-1H-pyrazol-4-yl)—(CA Index Name)." Nov. 9, 2006.
CAS Registry No. 912787-86-1. "3-Isoxazolecarboxamide, 5-(4-chlorophenyl)-N-(2,3-dihydro-1,5-dimethyl-3-oxo-2-phenyl-1H-pyrazol-4-yl)—(CA Index Name)." Nov. 9, 2006.
CAS Registry No. 912790-12-6. "3-Isoxazolecarboxamide, N-(2,3-dihydro-1,5-dimethyl-3-oxo-2-phenyl-1H-pyrazol-4-yl)-5-(3-hydroxyphenyl)—(CA Index Name)." Nov. 9, 2006.
CAS Registry No. 912795-89-2. "3-Isoxazolecarboxamide, N-(2,3-dihydro-1,5-dimethyl-3-oxo-2-phenyl-1H-pyrazol-4-yl)-5-(4-methoxyphenyl)—(CA Index Name)." Nov. 9, 2006.
CAS Registry No. 206037-29-7. "3-Isoxazolecarboxamide, 5-(3,4-difluorophenyl)-N-(2,3-dihydro-1,5-dimethyl-3-oxo-2-phenyl-1H-pyrazol-4-yl)—(CA Index Name)." Feb. 11, 2010.
CAS Registry No. 901665-66-5. "3-Isoxazolecarboxamide, 5-(2,3-dihydro-1,4-benzodioxin-6-yl)-N-(2,3-dihydro-1,5-dimethyl-3-oxo-2-phenyl-1H-pyrazol-4-yl)—(CA Index Name)." Aug. 16, 2006.
CAS Registry No. 907986-78-1. Index Name Not Yet Assigned. Sep. 20, 2006.
CAS Registry No. 1302184-45-7. "3-Isoxazolecarboxamide, N-(2,3-dihydro-1,5-dimethyl-3-oxo-2-phenyl-1H-pyrazol-4-yl)-5-(2-fluorophenyl)—(CA Index Name)." May 29, 2011.
CAS Registry No. 688050-41-1. "3-Isoxazolecarboxamide, N-(2,3-dihydro-1,5-dimethyl-3-oxo-2-phenyl-1H-pyrazol-4-yl)-5-(4-fluorophenyl)—(CA Index Name)." Jun. 1, 2004.
International Search Report and Written Opinion for International Application No. PCT/IB2015/001539 mailed Oct. 27, 2015.
Database PubChem Compound. Compound Summary for: CID 55855650. XP002727692. Published on Jan. 25, 2012. Printed on Jul. 23, 2014. 3 pages. https://pubchem.ncbi.nlm.nih.gov/summary/summary.cgi?cid=55855650.
Database PubChem Compound. Compound Summary for: CID 55882610. XP002727693. Published on Jan. 25, 2012. Printed on Jul. 23, 2014. 3 pages. https://pubchem.ncbi.nlm.nih.gov/summary/summary.cgi?cid=55882610.

CARBOXAMIDE DERIVATIVES

FIELD OF THE INVENTION

The present invention describes organic compounds useful in therapy. The compounds demonstrate properties as selective Smurf-1 inhibitors and may thus be useful in the treatment of a range of disorders, such as for example, pulmonary arterial hypertension, glaucoma, hereditary hemorrhagic telangiectasia (HHT), proteinuria, wound healing, as well as COPD and asthma.

BACKGROUND OF THE INVENTION

Smurf-1 (Smad ubiquitination regulatory factor 1) is a member of the HECT family of E3 ubiquitin ligase marking specific substrates for proteolytic degradation via the ubiquitin-dependent proteolytic pathway. Major substrates of Smurf-1 include RhoA, bone morphogenetic protein (BMP) receptor (BMPR) 1 and 2, smad1 and 5, TNFα receptor associated factor (TRAF) 6 and myD88 (Andrews, P. S. et al. Assay Drug Dev. Technol. 2010). Given the list of substrates, Smurf-1 has established roles in regulating BMP signaling (Chen, D et al. Growth Factors, 2004), neuronal cell polarity (Stiess, M. and Bradke, F. Neuron, 2011), cell migration (Huang, C. Cell Adh. Migr. 2010), tumor cell invasion (Sahai, E. et al. JCB, 2007), mitochondrial autophagy (Orvedahl, A. Nature, 2011) mesenchymal stem cell proliferation (Zhao, L. et al. J. Bone Miner. Res. 2010) and epithelial-mesenchymal transition (EMT) (Ozdamar, B et al. Science 2005).

Pulmonary arterial hypertension (PAH) is a life-threatening aggressive and complex disease of multiple etiologies, characterized by a progressive pulmonary vasculopathy leading to right ventricular hypertrophy/failure and in most cases premature death. Current pharmacological therapies are palliative. Whilst improvements in life expectancy have been observed, current therapies, which focus on altering the vasoconstrictive elements of the disease, do not halt or reverse progression of the disease, and transplantation (double lung or heart-lung) remains the only curative treatment. Given the limited effect of current treatment classes, novel therapies targeting the underlying progressive pulmonary vascular remodeling of PAH are needed.

Germline mutations in the transforming growth factor β (TGF-β) superfamily receptor bone morphogenetic protein receptor II (BMPR-II) gene are prevalent in seventy percent of heritable and some sporadic forms of idiopathic PAH (IPAH). Bone morphogenetic proteins are signaling molecules that belong to the TGF-β superfamily. Bone morphogenetic proteins were originally identified by their ability to induce formation of cartilage and bone, and subsequently identified to be multifunctional proteins that regulate a wide spectrum of function such as proliferation, differentiation, and apoptosis in a large variety of cell types, including osteoblasts, epithelial cells, neurons, immune cells, and smooth muscle cells. So far, >20 mammalian BMPs have been identified, but only three type I and three type II receptors (BMPR-I and BMPR-II, respectively) that are capable of binding with BMPs have been cloned in mammals. Bone morphogenetic proteins are synthesized and secreted from a variety of cell types, including pulmonary vascular smooth muscle cells and endothelial cells. In addition to mutations in BMPR-I and -II, lungs from patients with non-familial PAH display markedly reduced levels of vascular BMPR-1 and -II implying a central role for disrupted BMP signaling in many forms of PAH (Du, L et al. N. Eng. J. Med, 2003). Restoration of BMP signaling in the pulmonary vasculature of PAH patients is therefore of considerable interest in the development of novel anti-remodeling therapeutics for the treatment of PAH.

Smurf-1 has been shown to mediate degradation of BMPR-I, -II and smad1 and 5 in a variety of cell types including osteoblasts (Zhao, M et al. JBC, 2003), myoblasts (Ying, S X et al. JBC, 2003), lung epithelium (Shi W, et al. Am. J. Physiol. Cell. Mol. Physiol, 2004), neuronal tissue (Kallan, T et al. Mol. Cell. Biol, 2009) and endocardial cells (Towsend, T A, et al. Cells Tissues Organs, 2011). Recently, the first evidence has emerged supporting a role for Smurf-1 in PAH where enhanced levels of Smurf-1 were observed in the chronic hypoxia and monocrotaline pre-clinical in-vivo models of PAH and associated with down-regulation of BMPR1 and 2 (Murakami, K, et al. Exp. Biol. Med, 2010 and Yang, J. et al. Circ. Res, 2010).

SUMMARY OF THE INVENTION

There remains a need for new treatments and therapies for pulmonary arterial hypertension. The invention provides compounds, pharmaceutically acceptable salts or co-crystals thereof, pharmaceutical compositions thereof and combinations thereof, which compounds are Smurf-1 inhibitors. The invention further provides methods of treating, preventing, or ameliorating pulmonary arterial hypertension, comprising administering to a subject in need thereof an effective amount of a Smurf-1 inhibitors.

According to a first aspect of the invention, Embodiment 1, there is provided a compound of formula (I):

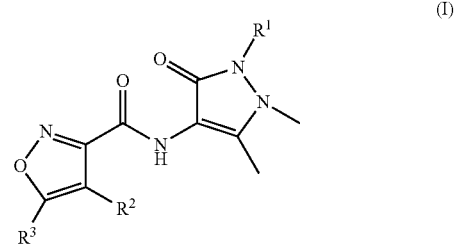

(I)

or a pharmaceutically acceptable salt or co-crystal thereof, wherein $R^1$ is $(C_3-C_6)$alkyl or $(C_3-C_6)$cycloalkyl;

$R^2$ is methyl;

$R^3$ is selected from $(C_6-C_{10})$branched alkyl, $(C_6-C_{10})$ branched alkenyl, $(C_5-C_8)$cycloalkenyl, $(C_5-C_8)$cycloalkyl, or Het; wherein the $(C_5-C_8)$cycloalkenyl or $(C_5-C_8)$cycloalkyl is unsubstituted or is substituted by one, two, three or four substituents $R^4$; and wherein Het is substituted by one, two, three or four substituents $R^4$;

each $R^4$ is independently selected from halo, $(C_1-C_4)$alkyl, halo$(C_1-C_4)$alkyl, $(C_1-C_4)$alkoxy, or halo$(C_1-C_4)$alkoxy; or two $R^4$ groups, when attached to the same carbon atom, may be taken together with the carbon atom to which they are attached to form a cyclopentyl, tetrahydrofuran or dioxolane ring; and Het is a 5 or 6 membered fully saturated or partially saturated heterocyclic ring comprising a) 1 oxygen atom in the 2- or 3-position, or b) 2 oxygen atoms in the 2- and 5-, or 2- and 6-positions, wherein the numbering is relative to the point of attachment; and $(C_5-C_8)$cycloalkyl may be a monocyclic ring or a bridged ring system containing 5, 6, 7 or 8 carbon atoms.

In another embodiment is provided a compound of Formula (I) as defined above or a pharmaceutically acceptable salt thereof.

In another embodiment, the invention provides a pharmaceutical composition comprising a therapeutically effective amount of a compound according to the definition of formula (I), or a pharmaceutically acceptable salt or co-crystal thereof, or subformulae thereof and one or more pharmaceutically acceptable carriers. In another embodiment, the invention provides a pharmaceutical composition comprising a therapeutically effective amount of a compound according to the definition of formula (I), or a pharmaceutically acceptable salt thereof, or subformulae thereof and one or more pharmaceutically acceptable carriers.

In another embodiment, the invention provides a method of treating a disorder or disease selected from Pulmonary Hypertension, including Pulmonary arterial hypertension (PAH), Fibrosis, Rheumatoid Arthritis, Fracture healing, glaucoma, hereditary hemorrhagic telangiectasia (HHT), proteinuria, wound healing, as well as COPD and asthma, comprising administering to the subject a therapeutically effective amount of the compound according to the definition of formula (I), or a pharmaceutically acceptable salt or co-crystal thereof, or subformulae thereof or a pharmaceutically acceptable salt or co-crystal thereof. In some embodiments, the subject is administered a therapeutically effective amount of a compound according to the definition of formula (I), or a pharmaceutically acceptable salt thereof. In other embodiments, the subject is administered a therapeutically effective amount of a compound according to a subgenera of formula (I), or a pharmaceutically acceptable salt thereof. Still other embodiments provide a method of treating a disorder or disease selected from glaucoma, hereditary hemorrhagic telangiectasia (HHT), proteinuria, wound healing, COPD and asthma.

In another embodiment, the invention provides a combination, in particular a pharmaceutical combination, comprising a therapeutically effective amount of the compound according to the definition of formula (I), or a pharmaceutically acceptable salt or co-crystal thereof, or subformulae thereof and one or more therapeutically active agents.

Various embodiments of the invention are described herein.

DETAILED DESCRIPTION

The invention therefore provides a compound of the formula (I) or a pharmaceutically acceptable salt or co-crystal thereof, as described hereinabove as Embodiment 1.

Embodiment 2

A compound according to Embodiment 1 or a pharmaceutically acceptable salt or co-crystal thereof, wherein $R^1$ is iso-propyl, cyclobutyl or cyclohexyl.

Embodiment 3

A compound according to Embodiment 1 or a pharmaceutically acceptable salt or co-crystal thereof, wherein $R^1$ is cyclohexyl.

Embodiment 4

A compound according to any preceding Embodiment or a pharmaceutically acceptable salt or co-crystal thereof, wherein $R^3$ is selected from 2,2-dimethylpentyl, 2,2-dimethylpent-2-enyl, cyclopentyl, cyclohexyl, cyclohexenyl, tetrahydropyranyl, dihydropyranyl, dioxanyl, tetrahydrofuranyl, dioxolanyl and bicyclo[2.2.2]octanyl; wherein the cyclopentyl, cyclohexyl, cyclohexenyl, tetrahydropyranyl, dihydropyranyl, dioxanyl, tetrahydrofuranyl, dioxolanyl or bicyclo[2.2.2]octanyl ring is unsubstituted or is substituted by one, two, three or four substituents $R^4$; and each $R^4$ is independently selected from halo, $(C_1-C_4)$alkyl, halo$(C_1-C_4)$alkyl, $(C_1-C_4)$alkoxy, or halo$(C_1-C_4)$alkoxy; or two $R^4$ groups, when attached to the same carbon atom, may be taken together with the carbon atom to which they are attached to form a tetrahydrofuran or dioxolane ring.

Embodiment 5

A compound according to any preceding Embodiment, or a pharmaceutically acceptable salt or co-crystal thereof, wherein $R^3$ is

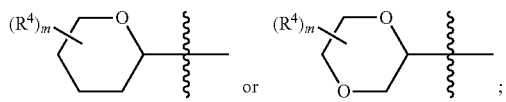

and m is 1, 2, 3 or 4.

Embodiment 6

A compound according to any preceding Embodiment, or a pharmaceutically acceptable salt or co-crystal thereof, wherein $R^3$ is

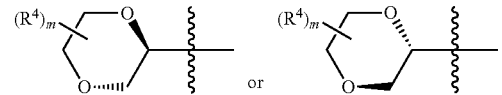

and m is 1, 2, 3 or 4.

Embodiment 7

A compound according to any preceding Embodiment, or a pharmaceutically acceptable salt or co-crystal thereof, wherein each $R^4$ is independently selected from methyl, isopropyl, tert-butyl and methoxy.

Embodiment 8

A compound of formula (I), according to Embodiment 1, wherein the compound is selected from Example 1

[N-(2-Cyclohexyl-1,5-dimethyl-3-oxo-2,3-dihydro-1H-pyrazol-4-yl)-5-(4-isopropylcyclohex-1-en-1-yl)-4-methylisoxazole-3-carboxamide];

Example 1.1

N-(2-Cyclohexyl-1,5-dimethyl-3-oxo-2,3-dihydro-1H-pyrazol-4-yl)-5-(6-ethyl-4-methylcyclohex-1-en-1-yl)-4-methylisoxazole-3-carboxamide;

Example 1.2

N-(2-Cyclohexyl-1,5-dimethyl-3-oxo-2,3-dihydro-1H-pyrazol-4-yl)-5-(6,6-dimethylcyclohex-1-en-1-yl)-4-methylisoxazole-3-carboxamide;

Example 1.3

[N-(2-Cyclohexyl-1,5-dimethyl-3-oxo-2,3-dihydro-1H-pyrazol-4-yl)-5-(4-ethylcyclohex-1-en-1-yl)-4-methylisoxazole-3-carboxamide];

Example 1.4

[5-(4-(tert-Butyl)cyclohex-1-en-1-yl)-N-(2-cyclohexyl-1,5-dimethyl-3-oxo-2,3-dihydro-1H-pyrazol-4-yl)-4-methylisoxazole-3-carboxamide];

Example 1.5

[N-(2-Cyclohexyl-1,5-dimethyl-3-oxo-2,3-dihydro-1H-pyrazol-4-yl)-4-methyl-5-(4-methylcyclohex-1-en-1-yl)isoxazole-3-carboxamide];

Example 1.6

5-(Cyclohept-1-en-1-yl)-N-(2-cyclohexyl-1,5-dimethyl-3-oxo-2,3-dihydro-1H-pyrazol-4-yl)-4-methylisoxazole-3-carboxamide;

Example 1.7

[N-(2-Cyclohexyl-1,5-dimethyl-3-oxo-2,3-dihydro-1H-pyrazol-4-yl)-4-methyl-5-(4-(trifluoromethyl)cyclohex-1-en-1-yl)isoxazole-3-carboxamide];

Example 2

N-(2-Cyclohexyl-1,5-dimethyl-3-oxo-2,3-dihydro-1H-pyrazol-4-yl)-4-methyl-5-(spiro[4.5]dec-7-en-8-yl)isoxazole-3-carboxamide;

Example 2.1

[N-(2-Cyclohexyl-1,5-dimethyl-3-oxo-2,3-dihydro-1H-pyrazol-4-yl)-4-methyl-5-(1-oxaspiro[4.5]dec-7-en-8-yl)isoxazole-3-carboxamide];

Example 2.2

N-(2-Cyclohexyl-1,5-dimethyl-3-oxo-2,3-dihydro-1H-pyrazol-4-yl)-5-(4,4-dimethylcyclohex-1-en-1-yl)-4-methylisoxazole-3-carboxamide;

Example 3

N-(2-Cyclohexyl-1,5-dimethyl-3-oxo-2,3-dihydro-1H-pyrazol-4-yl)-5-(4,4-dimethylcyclopent-1-en-1-yl)-4-methylisoxazole-3-carboxamide;

Example 4

[N-(2-Cyclohexyl-1,5-dimethyl-3-oxo-2,3-dihydro-1H-pyrazol-4-yl)-4-methyl-5-(2-oxaspiro[4.5]dec-7-en-8-yl)isoxazole-3-carboxamide];

Example 5

[N-(2-Cyclohexyl-1,5-dimethyl-3-oxo-2,3-dihydro-1H-pyrazol-4-yl)-5-(4-isopropoxycyclohex-1-en-1-yl)-4-methylisoxazole-3-carboxamide];

Example 6

N-(2-Cyclohexyl-1,5-dimethyl-3-oxo-2,3-dihydro-1H-pyrazol-4-yl)-5-(4,4-dimethylcyclohexyl)-4-methylisoxazole-3-carboxamide;

Example 6.1

[N-(2-Cyclohexyl-1,5-dimethyl-3-oxo-2,3-dihydro-1H-pyrazol-4-yl)-5-(3,3-dimethylcyclopentyl)-4-methylisoxazole-3-carboxamide];

Example 7

N-(2-Cyclohexyl-1,5-dimethyl-3-oxo-2,3-dihydro-1H-pyrazol-4-yl)-5-(3,3-dimethylbutyl)-4-methylisoxazole-3-carboxamide;

Example 8

(Z)—N-(2-Cyclohexyl-1,5-dimethyl-3-oxo-2,3-dihydro-1H-pyrazol-4-yl)-5-(3,3-dimethylbut-1-en-1-yl)-4-methylisoxazole-3-carboxamide;

Example 9

(E)-N-(2-Cyclohexyl-1,5-dimethyl-3-oxo-2,3-dihydro-1H-pyrazol-4-yl)-5-(3,3-dimethylbut-1-en-1-yl)-4-methylisoxazole-3-carboxamide;

Example 10

5-Cyclohexyl-N-(2-cyclohexyl-1,5-dimethyl-3-oxo-2,3-dihydro-1H-pyrazol-4-yl)-4-methylisoxazole-3-carboxamide;

Example 11

N-(2-Cyclohexyl-1,5-dimethyl-3-oxo-2,3-dihydro-1H-pyrazol-4-yl)-4-methyl-5-(1,4-dioxaspiro[4.5]decan-8-yl)isoxazole-3-carboxamide;

Example 12

5-(6-(tert-butyl)-4-methoxytetrahydro-2H-pyran-2-yl)-N-(2-cyclohexyl-1,5-dimethyl-3-oxo-2,3-dihydro-1H-pyrazol-4-yl)-4-methylisoxazole-3-carboxamide;

Example 13

5-(6-(tert-butyl)-4-methoxytetrahydro-2H-pyran-2-yl)-N-(2-cyclohexyl-1,5-dimethyl-3-oxo-2,3-dihydro-1H-pyrazol-4-yl)-4-methylisoxazole-3-carboxamide;

Example 14

5-(6-(tert-butyl)-4-methoxytetrahydro-2H-pyran-2-yl)-N-(2-cyclobutyl-1,5-dimethyl-3-oxo-2,3-dihydro-1H-pyrazol-4-yl)-4-methylisoxazole-3-carboxamide;

Example 15

5-(6-(tert-butyl)tetrahydro-2H-pyran-2-yl)-N-(2-cyclobutyl-1,5-dimethyl-3-oxo-2,3-dihydro-1H-pyrazol-4-yl)-4-methylisoxazole-3-carboxamide;

Example 16

5-(6-(tert-butyl)tetrahydro-2H-pyran-2-yl)-N-(2-cyclohexyl-1,5-dimethyl-3-oxo-2,3-dihydro-1H-pyrazol-4-yl)-4-methylisoxazole-3-carboxamide;

Example 17

5-(6-(tert-butyl)tetrahydro-2H-pyran-2-yl)-N-(2-isopropyl-1,5-dimethyl-3-oxo-2,3-dihydro-1H-pyrazol-4-yl)-4-methylisoxazole-3-carboxamide;

Example 18

N-(2-cyclohexyl-1,5-dimethyl-3-oxo-2,3-dihydro-1H-pyrazol-4-yl)-5-(6-isopropyl-3,6-dihydro-2H-pyran-2-yl)-4-methylisoxazole-3-carboxamide;

Example 19

N-(2-cyclohexyl-1,5-dimethyl-3-oxo-2,3-dihydro-1H-pyrazol-4-yl)-4-methyl-5-(6-methyl-3,6-dihydro-2H-pyran-2-yl)isoxazole-3-carboxamide;

Example 20

N-(2-Cyclohexyl-1,5-dimethyl-3-oxo-2,3-dihydro-1H-pyrazol-4-yl)-4-methyl-5-((2R,3S)-3,5,5-trimethyl-1,4-dioxan-2-yl)isoxazole-3-carboxamide;

Example 21.1

[5-(4-Bromo-5-methyltetrahydro-2H-pyran-2-yl)-N-(2-cyclohexyl-1,5-dimethyl-3-oxo-2,3-dihydro-1H-pyrazol-4-yl)-4-methylisoxazole-3-carboxamide];

Example 21.2

N-(2-cyclohexyl-1,5-dimethyl-3-oxo-2,3-dihydro-1H-pyrazol-4-yl)-4-methyl-5-(5-methyl-3,6-dihydro-2H-pyran-2-yl)isoxazole-3-carboxamide;

Example 22

N-(2-cyclohexyl-1,5-dimethyl-3-oxo-2,3-dihydro-1H-pyrazol-4-yl)-4-methyl-5-(5-methyltetrahydro-2H-pyran-2-yl)isoxazole-3-carboxamide;

Example 23

5-(4-(2-bromopropan-2-yl)tetrahydrofuran-2-yl)-N-(2-cyclohexyl-1,5-dimethyl-3-oxo-2,3-dihydro-1H-pyrazol-4-yl)-4-methylisoxazole-3-carboxamide;

Example 24

N-(2-cyclohexyl-1,5-dimethyl-3-oxo-2,3-dihydro-1H-pyrazol-4-yl)-5-(4-isopropyltetrahydrofuran-2-yl)-4-methylisoxazole-3-carboxamide;

Example 25

5-(4-(tert-butyl)-1,3-dioxolan-2-yl)-N-(2-cyclohexyl-1,5-dimethyl-3-oxo-2,3-dihydro-1H-pyrazol-4-yl)-4-methylisoxazole-3-carboxamide;

Example 26

N-(2-Cyclohexyl-1,5-dimethyl-3-oxo-2,3-dihydro-1H-pyrazol-4-yl)-5-(5,5-dimethyl-1,3-dioxan-2-yl)-4-methylisoxazole-3-carboxamide;

or a pharmaceutically acceptable salt or co-crystal thereof.

Embodiment 9

A compound of formula (I), according to Embodiment 1, wherein the compound is selected from

Example 20

N-(2-Cyclohexyl-1,5-dimethyl-3-oxo-2,3-dihydro-1H-pyrazol-4-yl)-4-methyl-5-((2R,3S)-3,5,5-trimethyl-1,4-dioxan-2-yl)isoxazole-3-carboxamide;

Example 26

N-(2-Cyclohexyl-1,5-dimethyl-3-oxo-2,3-dihydro-1H-pyrazol-4-yl)-5-(5,5-dimethyl-1,3-dioxan-2-yl)-4-methylisoxazole-3-carboxamide;

Example 2.2

N-(2-Cyclohexyl-1,5-dimethyl-3-oxo-2,3-dihydro-1H-pyrazol-4-yl)-5-(4,4-dimethylcyclohex-1-en-1-yl)-4-methylisoxazole-3-carboxamide;

Example 2.1

[N-(2-Cyclohexyl-1,5-dimethyl-3-oxo-2,3-dihydro-1H-pyrazol-4-yl)-4-methyl-5-(1-oxaspiro[4.5]dec-7-en-8-yl)isoxazole-3-carboxamide]; and

Example 11

N-(2-Cyclohexyl-1,5-dimethyl-3-oxo-2,3-dihydro-1H-pyrazol-4-yl)-4-methyl-5-(1,4-dioxaspiro[4.5]decan-8-yl)isoxazole-3-carboxamide;

or a pharmaceutically acceptable salt or co-crystal thereof.

Embodiment 10

A compound of formula (I), according to embodiment 1, wherein the compound is

Example 20

N-(2-Cyclohexyl-1,5-dimethyl-3-oxo-2,3-dihydro-1H-pyrazol-4-yl)-4-methyl-5-((2R,3S)-3,5,5-trimethyl-1,4-dioxan-2-yl)isoxazole-3-carboxamide, or a pharmaceutically acceptable salt or co-crystal thereof.

Embodiment 11

A compound of formula (I), according to embodiment 1, wherein the compound is

Example 26

N-(2-Cyclohexyl-1,5-dimethyl-3-oxo-2,3-dihydro-1H-pyrazol-4-yl)-5-(5,5-dimethyl-1,3-dioxan-2-yl)-4-methylisoxazole-3-carboxamide, or a pharmaceutically acceptable salt or co-crystal thereof.

Embodiment 12

A compound of formula (I), according to embodiment 1, wherein the compound is

Example 2.2

N-(2-Cyclohexyl-1,5-dimethyl-3-oxo-2,3-dihydro-1H-pyrazol-4-yl)-5-(4,4-dimethylcyclohex-1-en-1-yl)-4-methyl-isoxazole-3-carboxamide or a pharmaceutically acceptable salt or co-crystal thereof.

Embodiment 13

A compound of formula (I), according to embodiment 1, wherein the compound is

Example 2.1

[N-(2-Cyclohexyl-1,5-dimethyl-3-oxo-2,3-dihydro-1H-pyrazol-4-yl)-4-methyl-5-(1-oxaspiro[4.5]dec-7-en-8-yl) isoxazole-3-carboxamide] or a pharmaceutically acceptable salt or co-crystal thereof.

Embodiment 14

A compound of formula (I), according to embodiment 1, wherein the compound is

Example 11

N-(2-Cyclohexyl-1,5-dimethyl-3-oxo-2,3-dihydro-1H-pyrazol-4-yl)-4-methyl-5-(1,4-dioxaspiro[4.5]decan-8-yl) isoxazole-3-carboxamide or a pharmaceutically acceptable salt or co-crystal thereof.

As used herein, the term "halo" (or halogen) refers to fluorine, bromine, chlorine or iodine, in particular fluorine, chlorine. Halogen-substituted groups and moieties, such as alkyl substituted by halogen (haloalkyl) can be mono-, poly- or per-halogenated.

As used herein, the term "hetero atoms" refers to nitrogen (N), oxygen (O) or sulfur (S) atoms, in particular nitrogen or oxygen.

As used herein, the term "alkyl" refers to a fully saturated branched or unbranched hydrocarbon moiety having up to 10 carbon atoms. Unless otherwise provided, alkyl refers to hydrocarbon moieties having 1 to 10 carbon atoms, 1 to 6 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. Representative examples of branched alkyl include, but are not limited to, iso-propyl, sec-butyl, iso-butyl, tert-butyl, isopentyl, 3-methylhexyl, 2,2-dimethylpentyl, 2,3-dimethylpentyl, and the like. A substituted alkyl is an alkyl group containing one or more, such as one, two or three substituents selected from halogen, hydroxy or alkoxy groups.

As used herein, the term "haloalkyl" refers to an alkyl as defined herein, which is substituted by one or more halo groups as defined herein. The haloalkyl can be monohaloalkyl, dihaloalkyl or polyhaloalkyl including perhaloalkyl. A monohaloalkyl can have one iodo, bromo, chloro or fluoro within the alkyl group. Dihaloalkyl and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Typically, alkoxy groups have 1-4 carbon atoms.

As used herein, the term "haloalkoxy" refers to an alkoxy as defined herein, which is substituted by one or more halo groups as defined herein.

Unless otherwise provided, as used herein, the term "cycloalkyl" refers to saturated monocyclic, bicyclic, or spirocyclic hydrocarbon groups of 3-8 carbon atoms. Unless otherwise provided, cycloalkyl refers to cyclic hydrocarbon groups having between 3 and 6 or between 5 and 8 ring carbon atoms.

As used herein, the term "cycloalkenyl" refers to partially saturated monocyclic, bicyclic, or spirocyclic hydrocarbon groups of 3-8 carbon atoms. Unless otherwise provided, cycloalkenyl refers to cyclic hydrocarbon groups having between 3 and 6 or between 5 and 8 ring carbon atoms.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

In many cases, the compounds of the present invention are capable of forming acid and/or base salts and or co-crystals by virtue of the presence of the carboxamide group or groups similar thereto.

Pharmaceutically acceptable acid addition salts or co-crystals can be formed with inorganic acids and organic acids.

Inorganic acids from which salts or co-crystals can be derived include, for example, hydrochloric acid, hydrobromic acid, sulfuric acid, nitric acid, phosphoric acid, and the like.

Organic acids from which salts or co-crystals can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, and the like.

Pharmaceutically acceptable base addition salts or co-crystals can be formed with inorganic and organic bases.

Inorganic bases from which salts or co-crystals can be derived include, for example, ammonium salts and metals from columns I to XII of the periodic table. In certain embodiments, the salts are derived from sodium, potassium, ammonium, calcium, magnesium, silver, and zinc; particularly suitable salts include ammonium, potassium, sodium, calcium and magnesium salts.

Organic bases from which salts or co-crystals can be derived include, for example, primary, secondary, and tertiary amines, substituted amines including naturally occurring substituted amines, cyclic amines, basic ion exchange resins, and the like. Certain organic amines include cholinate, lysine, meglumine, piperazine and tromethamine.

In another aspect, the present invention provides compounds of formula I in acetate, ascorbate, adipate, aspartate, benzoate, besylate, bromide/hydrobromide, bicarbonate/carbonate, bisulfate/sulfate, caprate, chloride/hydrochloride, citrate, ethandisulfonate, fumarate, gluceptate, gluconate, glucuronate, glutamate, glutarate, glycolate, hippurate, hydroiodide/iodide, isethionate, lactate, lactobionate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfate, tartrate, tosylate trifenatate, or xinafoate salt or co-crystal form.

In one embodiment, the present invention provides N-(2-Cyclohexyl-1,5-dimethyl-3-oxo-2,3-dihydro-1H-pyrazol-4-yl)-4-methyl-5-((2R,3S)-3,5,5-trimethyl-1,4-dioxan-2-yl)isoxazole-3-carboxamide in acetate, ascorbate, adipate, aspartate, benzoate, besylate, bromide/hydrobromide, bicarbonate/carbonate, bisulfate/sulfate, caprate, chloride/hydrochloride, citrate, ethandisulfonate, fumarate, gluceptate, gluconate, glucuronate, glutamate, glutarate, glycolate, hippurate, hydroiodide/iodide, isethionate, lactate, lactobionate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfate, tartrate, tosylate trifenatate, or xinafoate salt or co-crystal form.

In another embodiment, the present invention provides N-(2-Cyclohexyl-1,5-dimethyl-3-oxo-2,3-dihydro-1H-pyrazol-4-yl)-5-(5,5-dimethyl-1,3-dioxan-2-yl)-4-methylisoxazole-3-carboxamide in acetate, ascorbate, adipate, aspartate, benzoate, besylate, bromide/hydrobromide, bicarbonate/carbonate, bisulfate/sulfate, caprate, chloride/hydrochloride, citrate, ethandisulfonate, fumarate, gluceptate, gluconate, glucuronate, glutamate, glutarate, glycolate, hippurate, hydroiodide/iodide, isethionate, lactate, lactobionate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfate, tartrate, tosylate trifenatate, or xinafoate salt or co-crystal form.

In another embodiment, the present invention provides N-(2-Cyclohexyl-1,5-dimethyl-3-oxo-2,3-dihydro-1H-pyrazol-4-yl)-5-(4,4-dimethylcyclohex-1-en-1-yl)-4-methylisoxazole-3-carboxamide in acetate, ascorbate, adipate, aspartate, benzoate, besylate, bromide/hydrobromide, bicarbonate/carbonate, bisulfate/sulfate, caprate, chloride/hydrochloride, citrate, ethandisulfonate, fumarate, gluceptate, gluconate, glucuronate, glutamate, glutarate, glycolate, hippurate, hydroiodide/iodide, isethionate, lactate, lactobionate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfate, tartrate, tosylate trifenatate, or xinafoate salt or co-crystal form.

In another embodiment, the present invention provides [N-(2-Cyclohexyl-1,5-dimethyl-3-oxo-2,3-dihydro-1H-pyrazol-4-yl)-4-methyl-5-(1-oxaspiro[4.5]dec-7-en-8-yl)isoxazole-3-carboxamide] in acetate, ascorbate, adipate, aspartate, benzoate, besylate, bromide/hydrobromide, bicarbonate/carbonate, bisulfate/sulfate, caprate, chloride/hydrochloride, citrate, ethandisulfonate, fumarate, gluceptate, gluconate, glucuronate, glutamate, glutarate, glycolate, hippurate, hydroiodide/iodide, isethionate, lactate, lactobionate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfate, tartrate, tosylate trifenatate, or xinafoate salt or co-crystal form.

In another embodiment, the present invention provides N-(2-Cyclohexyl-1,5-dimethyl-3-oxo-2,3-dihydro-1H-pyrazol-4-yl)-4-methyl-5-(1,4-dioxaspiro[4.5]decan-8-yl)isoxazole-3-carboxamide in acetate, ascorbate, adipate, aspartate, benzoate, besylate, bromide/hydrobromide, bicarbonate/carbonate, bisulfate/sulfate, caprate, chloride/hydrochloride, citrate, ethandisulfonate, fumarate, gluceptate, gluconate, glucuronate, glutamate, glutarate, glycolate, hippurate, hydroiodide/iodide, isethionate, lactate, lactobionate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfate, tartrate, tosylate trifenatate, or xinafoate salt or co-crystal form.

In another aspect, the present invention provides compounds of formula I in sodium, potassium, ammonium, calcium, magnesium, silver, zinc, cholinate, lysine, meglumine, piperazine or tromethamine salt or co-crystal form.

In one embodiment, the present invention provides N-(2-Cyclohexyl-1,5-dimethyl-3-oxo-2,3-dihydro-1H-pyrazol-4-yl)-4-methyl-5-((2R,3S)-3,5,5-trimethyl-1,4-dioxan-2-yl)isoxazole-3-carboxamide in sodium, potassium, ammonium, calcium, magnesium, silver, zinc, cholinate, lysine, meglumine, piperazine or tromethamine salt or co-crystal form.

In one embodiment, the present invention provides N-(2-Cyclohexyl-1,5-dimethyl-3-oxo-2,3-dihydro-1H-pyrazol-4-yl)-5-(5,5-dimethyl-1,3-dioxan-2-yl)-4-methylisoxazole-3-carboxamide in sodium, potassium, ammonium, calcium, magnesium, silver, zinc, cholinate, lysine, meglumine, piperazine or tromethamine salt or co-crystal form.

In one embodiment, the present invention provides N-(2-Cyclohexyl-1,5-dimethyl-3-oxo-2,3-dihydro-1H-pyrazol-4-yl)-5-(4,4-dimethylcyclohex-1-en-1-yl)-4-methylisoxazole-3-carboxamide in sodium, potassium, ammonium, calcium, magnesium, silver, zinc, cholinate, lysine, meglumine, piperazine or tromethamine salt or co-crystal form.

In one embodiment, the present invention provides [N-(2-Cyclohexyl-1,5-dimethyl-3-oxo-2,3-dihydro-1H-pyrazol-4-yl)-4-methyl-5-(1-oxaspiro[4.5]dec-7-en-8-yl)isoxazole-3-carboxamide] in sodium, potassium, ammonium, calcium, magnesium, silver, zinc, cholinate, lysine, meglumine, piperazine or tromethamine salt or co-crystal form.

In one embodiment, the present invention provides N-(2-Cyclohexyl-1,5-dimethyl-3-oxo-2,3-dihydro-1H-pyrazol-4-yl)-4-methyl-5-(1,4-dioxaspiro[4.5]decan-8-yl)isoxazole-3-carboxamide in sodium, potassium, ammonium, calcium, magnesium, silver, zinc, cholinate, lysine, meglumine, piperazine or tromethamine salt or co-crystal form.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}P$, $^{35}S$, $^{36}Cl$, $^{123}I$, $^{124}I$, $^{125}I$ respectively. The invention includes various isotopically labeled compounds as defined herein, for example those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by Smurf-1, or (ii) associated with Smurf-1 activity, or (iii) characterized by activity (normal or abnormal) of Smurf-1; or (2) reduce or inhibit the activity of Smurf-1; or (3) reduce or inhibit the expression of Smurf-1. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of Smurf-1; or at least partially reducing or inhibiting the expression of Smurf-1.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, co-crystals, hydrates and solvates thereof, may inherently or by design form polymorphs.

Generic Schemes

Typically, the compounds of formula (I) can be prepared according to the Schemes provided infra.

The compounds of the present invention may be prepared by the routes described in the following Schemes or the Examples.

All abbreviations are as defined in the examples section hereinbelow.

Scheme 1

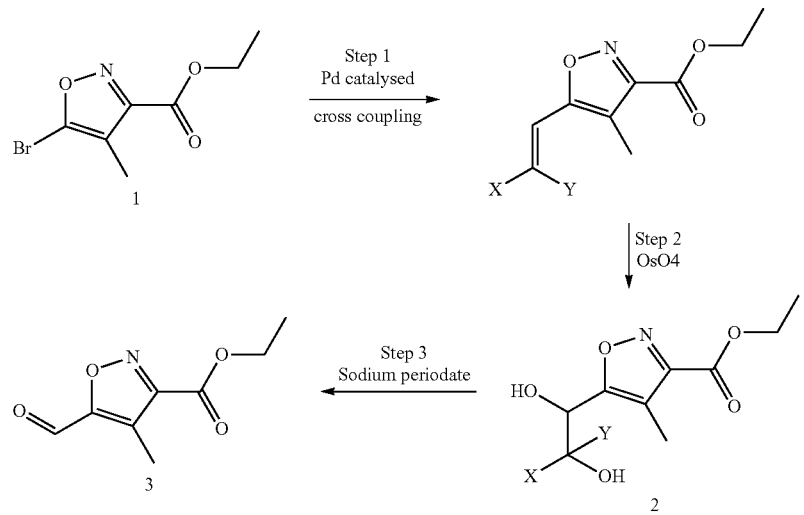

Wherein X and Y are independently H or —$(C_1$-$C_6)$alkyl.

Step 1: A Palladium Catalysed Cross Coupling Reaction.

Typical conditions: Palladium (0) catalyst; a suitable boron tin or zinc compound such as a boronic acid, boronate ester or stannane; organic or inorganic base; in water; in a suitable solvent at 80-110° C.

Preferred conditions: Bis(diphenylphosphino)ferrocene-palladium(II)dichloride, Vinyl Trifluoroborate salt, triethylamine in ethanol at 90° C.

Step 2: Dihydroxylation

Typical conditions: Osmium tetroxide; a suitable co-oxidant such as N-Methylmorpholine-N-Oxide; in a suitable solvent Preferred conditions: Osmium tetroxide (Admix alpha or Admix beta) may be used to access chiral diols, with a suitable additive such as Methane sulphonamide. A preferred solvent system is tButanol/water.

Step 3: Oxidative Cleavage

Typical conditions: Sodium Periodate in a THF/Water solvent system

When $R^2$ is methyl, a compound of formula (I) may be prepared according to Scheme 2.

Preferred conditions: a) LDA in THF at −78° C., followed by quenching with 1,1,1-trifluoro-N-(pyridin-2-yl)-N-((trifluoromethyl)sulfonyl)methanesulfonamide. b) 1,1'-Bis(diphenylphosphino)ferrocene-palladium(II)dichloride dichloromethane complex and bispinacolatodiboron, potassium acetate, in dioxane, at 80-100° C., for 4-16 h.

Step 2: Palladium Catalysed Cross Coupling

Typical conditions: As described in Scheme 1, step 1

Preferred conditions: 1,1'-Bis(diphenylphosphino)ferrocene-palladium(II)dichloride dichloromethane complex, Potassium carbonate (2M in water) in MeCN at 80° C., for 1.5 h Step 3a Saponification Typical conditions: A suitable aqueous base, optionally with a suitable co-solvent such as THF Preferred conditions: 2M Sodium Hydroxide (aq.) with THF at r.t. for 30 mins Step 3b Amide Coupling Typical conditions: A suitable coupling reagent such as HATU, T3P, EDCl etc, in the presence of a suitable base such as triethylamine, DIPEA etc, in a suitable aprotic solvent.

Scheme 2

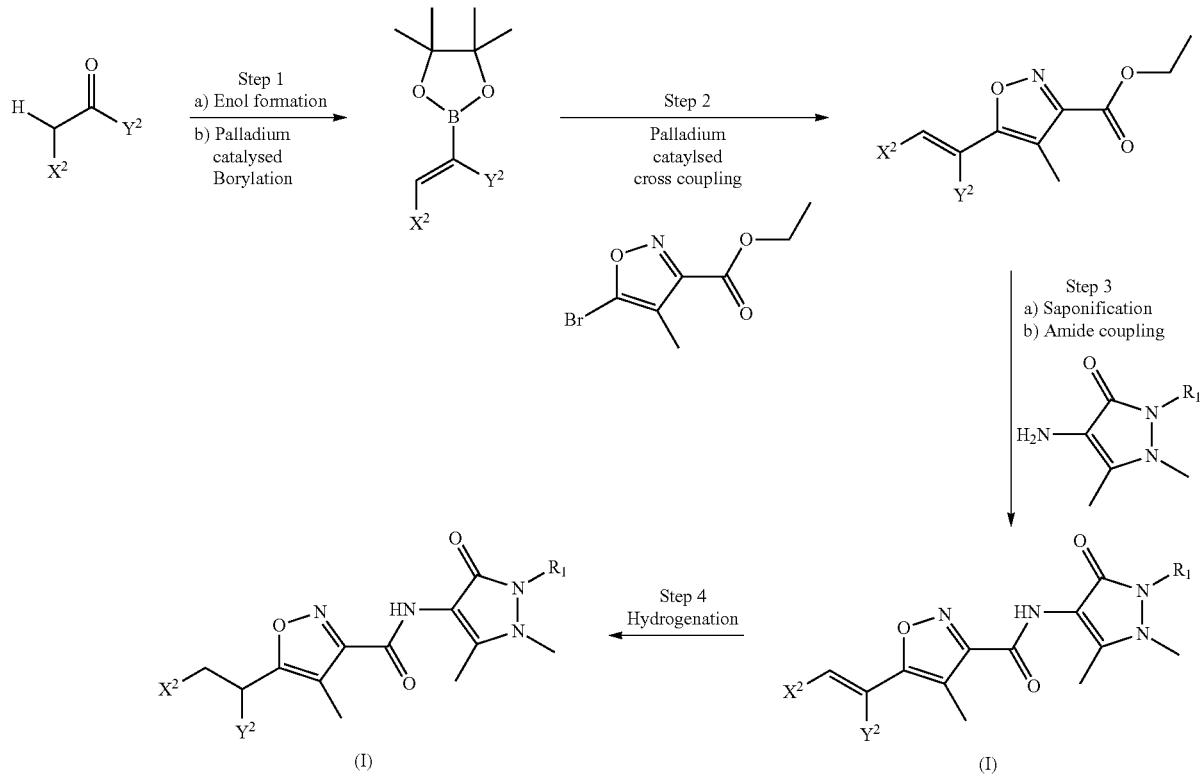

Wherein $X^2$ and $Y^2$ are defined such that, together with the carbon atoms to which they are attached, they form the $R^3$ substituent.

Step 1: Vinyl Boronate Formation

Typical conditions: a) Enolisation in the presence of a strong base, such as LDA or LHMDS, followed by quenching with a suitable haloalkyl sulphonate or sulphonamide to give the stabilised enol form. b) Palladium (0) cataylsed borylation of the enolate using a suitable Palladium (0) catalyst and bis pinacolatodiboron Preferred conditions: HATU and DIPEA in DMF at r.t. for around 2 h Step 4 Hydrogenation A compound of formula (I), wherein $R^3$ contains a C═C double bond, may be converted to a compound of formula (I), wherein $R^3$ is fully saturated, via a hydrogenation reaction.

Typical conditions: A non-soluble Palladium catalyst, Hydrogen gas, in a suitable solvent such as an alcohol Preferred conditions: 10% Palladium on Carbon and Hydrogen gas in ethanol Scheme 3

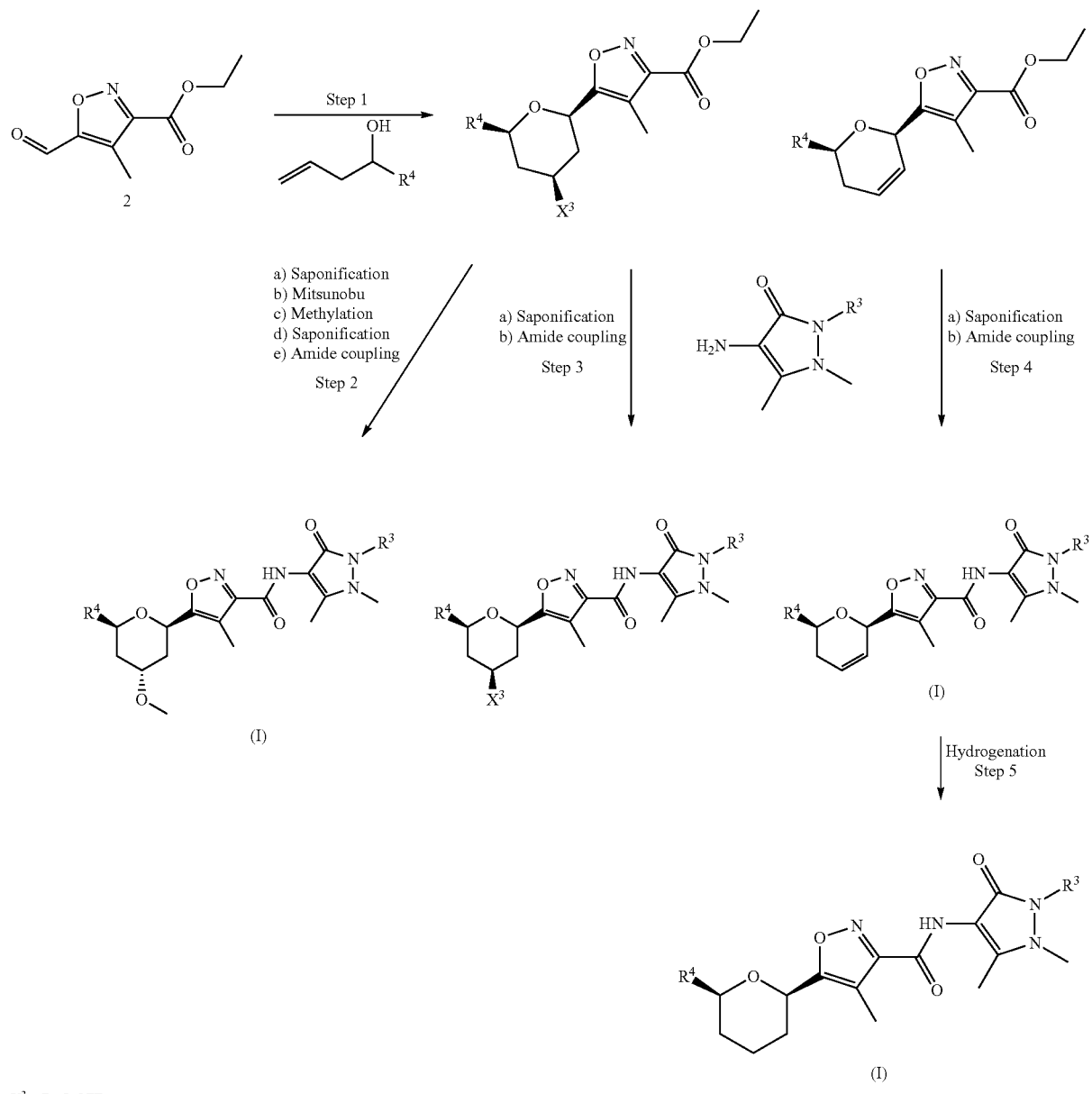

$X^3$ = Br, I, OTFA when $X^3$ is Br or I, the product of step 3 is also a compound of formula (I).

Step 1: A Prins Reaction

Typical conditions: An acid catalyst and a suitable dehydrating agent in a chlorinated solvent.

Preferred conditions: (i) Trifluoroacetic acid and Molecular sieves in DCM; or (ii) $InBr_3$ and Trimethyl silyl bromide in DCM; or (iii) $InOTf_3$ and Trimethyl silyl triflate in DCM.

Step 2a: A Saponification Reaction as Described in Scheme 2, Step 3a

Step 2b: A Mitsunobu Inversion

Typical conditions: A triarylphosphine, dialkylazodicarboxylate and benzoic acid, in a suitable solvent such as THF at r.t.

Preferred conditions: Triphenylphosphine, diisopropylazodicarboxylate, and 2,4-dinitrobenzoic acid, in THF at r.t.

Step 2c: Methylation

Typical conditions: A suitable strong base and an alkylating agent in a suitable solvent Preferred conditions: Sodium Hydride and Methyl Iodide in DMF Step 2d, Step 3a, Step 4a: A Saponification Reaction as Described in Scheme 2, Step 3a Step 2e, 3b and 4b: An Amide Coupling as Described in Scheme 2, Step 3b Step 5: Hydrogenation as Described in Scheme 2, Step 4

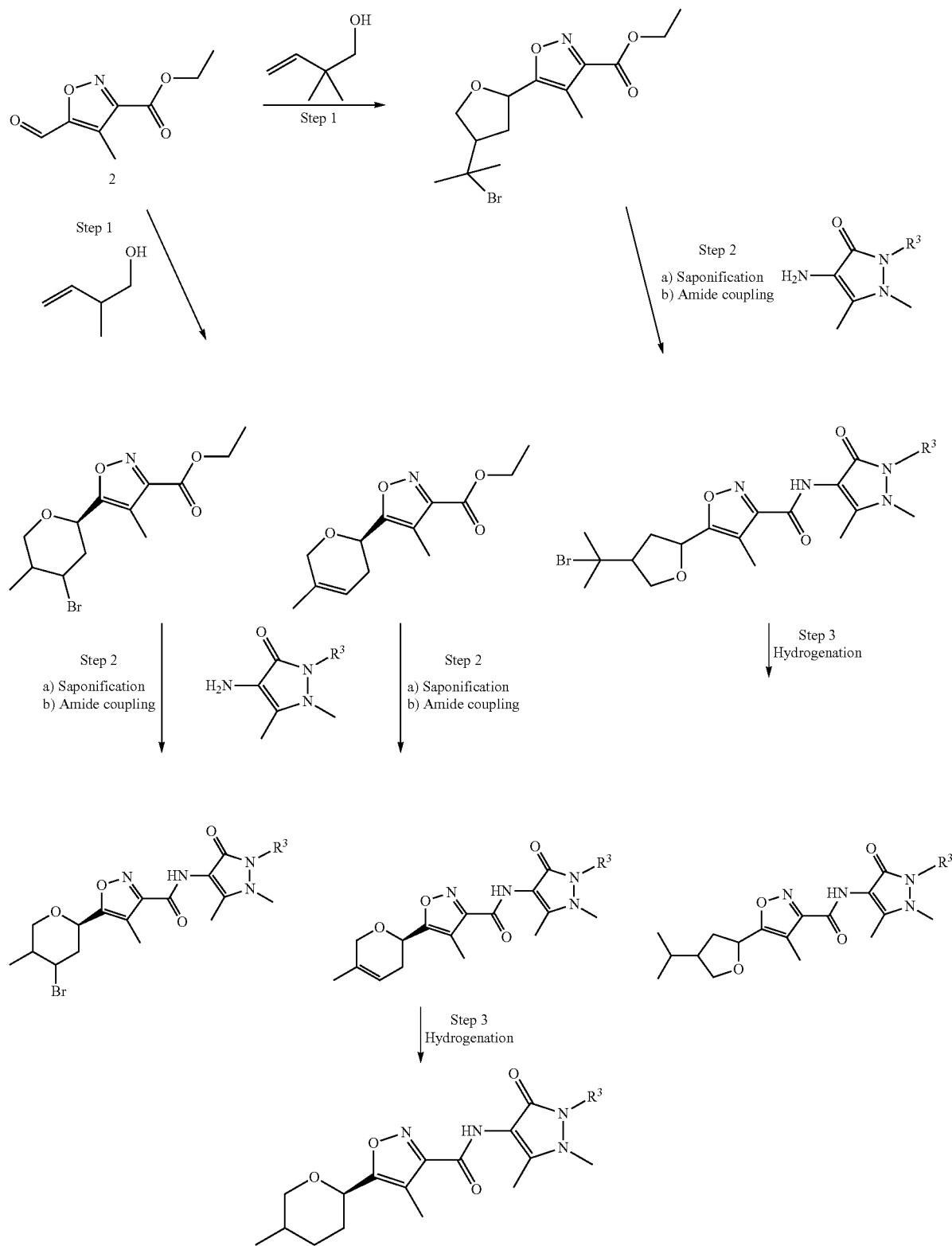
Scheme 4
Step 1: A Prins Reaction as Described in Scheme 3, Step 1
Step 2a: A Saponification Reaction as Described in Scheme 2, Step 3a
Step 2b: An Amide Coupling as Described in Scheme 2, Step 3b
Step 3: Hydrogenation as Described in Scheme 2, Step 4

Scheme 5
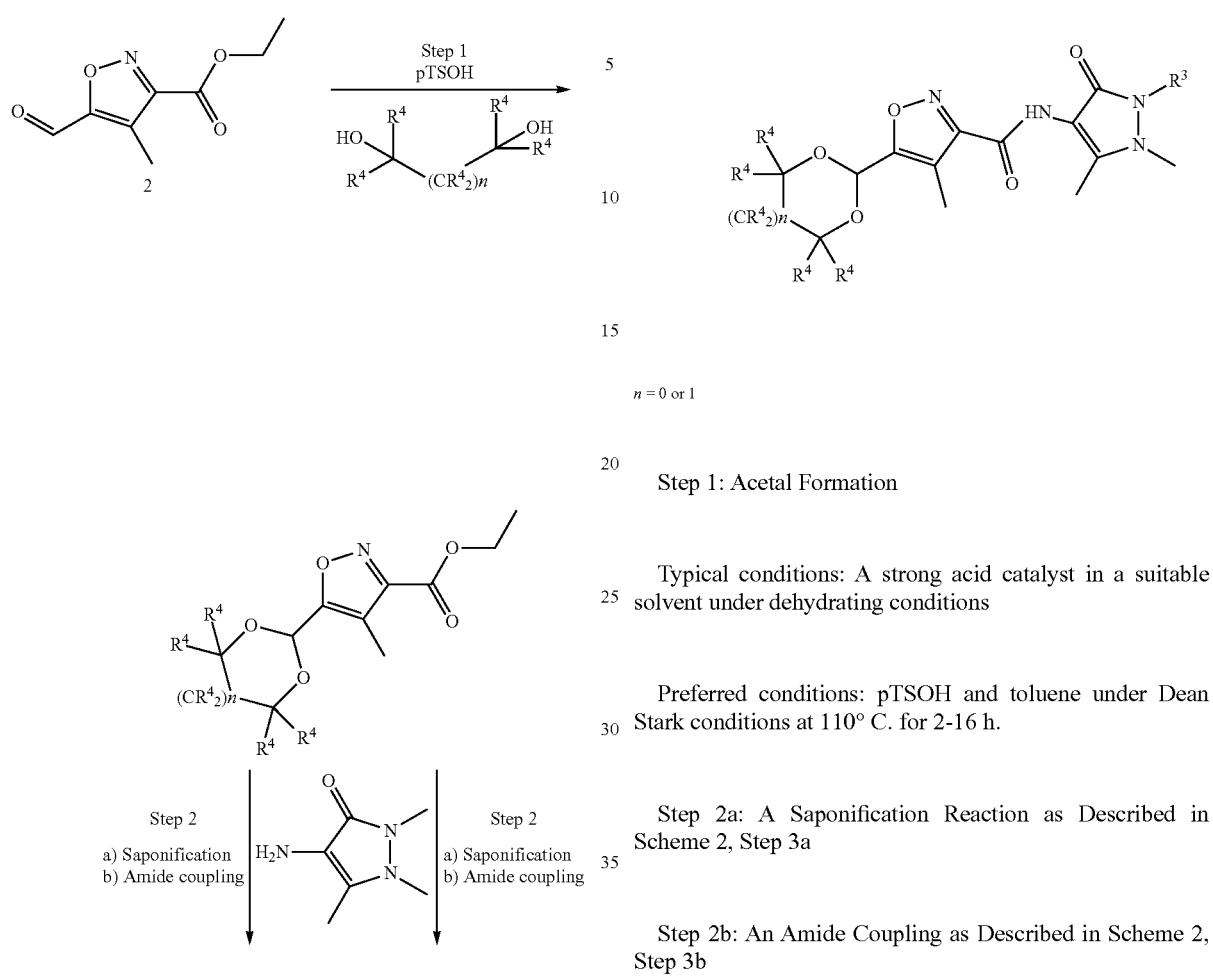
n = 0 or 1
Step 1: Acetal Formation
Typical conditions: A strong acid catalyst in a suitable solvent under dehydrating conditions
Preferred conditions: pTSOH and toluene under Dean Stark conditions at 110° C. for 2-16 h.
Step 2a: A Saponification Reaction as Described in Scheme 2, Step 3a
Step 2b: An Amide Coupling as Described in Scheme 2, Step 3b
Scheme 6
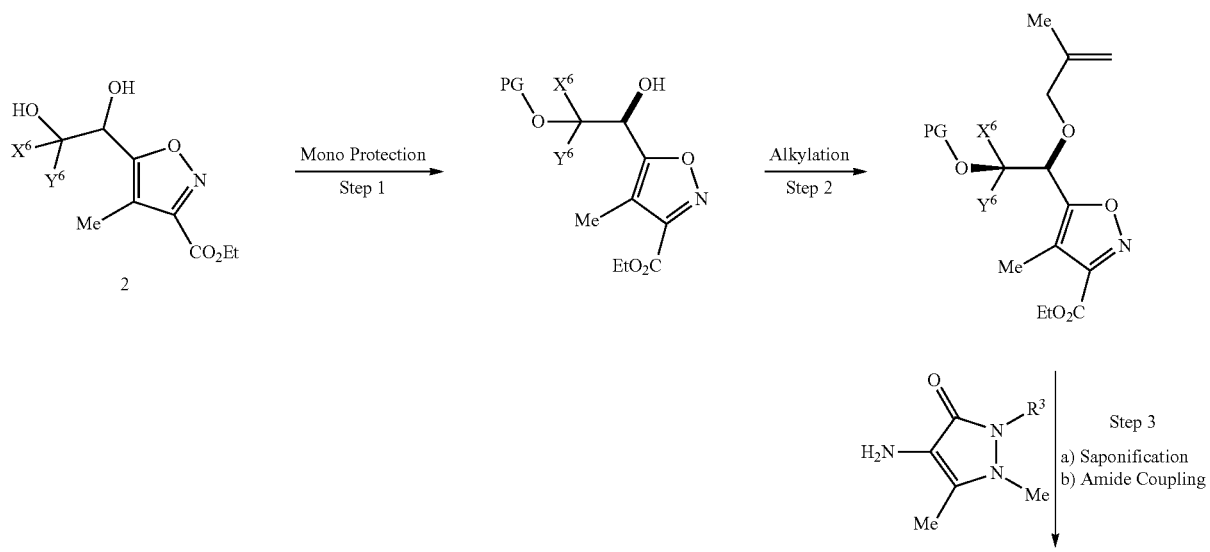

PG is a suitable protecting groups such as $^t$Butyldimethylsilyl $X^6$ and $Y^6$ are each independently H or —$(C_1-C_6)$alkyl.

Step 1: Protection

Typical conditions: A suitable protecting groups, such as a trialkylsilyl chloride, in the presence of a suitable base in a suitable solvent.

Preferred conditions: tButyldimethylsilyl chloride in the presence of triethylamine and DMAP in DMF.

Step 2: An Alkylation Reaction

Typical conditions: An allyl bromide in the presence of a suitable base in a suitable solvent.

Preferred conditions: 3-bromo-2-methylprop-1-ene and sodium Hydride in THF.

Step 3a: A Saponification Reaction as Described in Scheme 2, Step 3a

Step 3b: An Amide Coupling as Described in Scheme 2, Step 3b

Step 4: Deprotection

Typical Conditions: A fluoride source in a suitable solvent

Preferred Conditions: TBAF in THF

Step 5: A Cyclisation Reaction

Typical Conditions: Mercury (II) Trifluorocetate and Mercury (II) Oxide in THF at room temperature followed by addition of triethylborane and sodium borohydride at −78° C.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the invention and intermediates can also be converted into each other according to methods generally known to those skilled in the art.

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. For purposes of the present invention, unless designated otherwise, solvates and hydrates are generally considered compositions. Preferably, pharmaceutically acceptable carriers are sterile. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc. Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds of formula I in free form or in pharmaceutically acceptable salt form, exhibit valuable pharmacological properties, e.g. Smurf-1 modulating properties, e.g. as indicated in vitro and in vivo tests as provided in the next sections, and are therefore indicated for therapy or for use as research chemicals, e.g. as tool compounds.

Compounds of the invention or the pharmaceutically acceptable salts thereof are useful in the treatment of various indications including:

Pulmonary Hypertension, including Pulmonary arterial hypertension (PAH)
 Fibrosis
 Rheumatoid Arthritis
 Fracture healing
 Glaucoma
 hereditary hemorrhagic telangiectasia (HHT)
 proteinuria
 wound healing
 COPD
 asthma Pulmonary Arterial Hypertension (PAH)

Pulmonary arterial hypertension has a multifactoral pathobiology. Vasoconstriction, remodeling of the pulmonary vessel wall and thrombosis contribute to increased pulmonary vascular resistance in PAH (Humbert et al, J. Am. Coll. Cardiol., 2004.). The compounds of the present invention disclosed herein are useful in the treatment of PAH and symptoms thereof. Pulmonary arterial hypertension shall be understood to encompass the following forms of pulmonary hypertension: idiopathic PAH (IPAH); heritable PAH (HPAH); PAH induced by drugs or toxins, PAH associated with other conditions (APAH), such as PAH associated with connective tissue diseases, PAH associated with HIV infection, PAH associated with portal hypertension, PAH associated with congenital heart diseases, PAH associated with schistosomiasis, PAH associated chronic haemolytic anaemia, or persistent pulmonary hypertension of the newborn (Galiè et al, ERJ, 2009; Simonneau et al, JACC, 2009).

Idiopathic PAH refers to PAH of undetermined cause. Heritable PAH refers to PAH for which hereditary transmission is suspected or documented including those harboring mutations in the BMP receptor, BMPR2 or those with mutations in ALK1 or endoglin (with or without hereditary hemorrhagic talangiectasia).

PAH associated with drugs or toxins shall be understood to encompass PAH associated with ingestion of aminorex, a fenfluramine compound (e.g. fenfluramine or dexfenfluramine), certain toxic oils (e.g. rapeseed oil), pyrrolizidine alkaloids (e.g. bush tea), monocrotaline, amphetamines, L-tryptophan, methamphetamines, cocaine, phenylpropanolamine, St John's Wort, chemotherapeutic agents or SSRI's.

PAH associated with connective tissue diseases shall be understood to encompass PAH associated with systemic sclerosis, lung fibrosis, polymyositis, rheumatoid arthritis, Sjogren syndrome or PAH associated with systemic lupus erythematosis.

PAH associated with congenital heart diseases shall be understood to encompass patients with systemic to pulmonary shunts, PAH associated with Eisenmenger syndrome, small ventricular-septal or atrial-septal defects or PAH associated with corrective cardiac surgery.

PAH associated with chronic hemolytic anemia shall be understood to encompass patients with chronic hereditary and acquired anemias including patients with sickle cell disease, thalassemia, hereditary spherocytosis, stomatocytosis and microangiopathic hemolytic anemia.

Symptoms of PAH include dyspnea, angina, syncope and edema (McLaughlin et al., Circulation, 2006, 114:1417-1431). The compounds of the present invention disclosed herein are useful in the treatment of symptoms of PAH.

Pulmonary Hypertension (PH)

Pulmonary hypertension (PH) shall be understood to be associated with the following conditions grouped according to the Dana Point clinical classification (Simonneau, G et al. JACCC, 2009):

Group 1'—PH shall be understood to be associated with patients harboring pulmonary veno-occlusive disease (PVOD) and pulmonary capillary hemangiomatosis (PCH).

Group 2—PH associated with left heart disease include those patients with left-sided ventricular or valvular diseases.

Group 3—PH as a result of lung diseases and/or hypoxia. Lung diseases resulting in PH shall be understood to encompass patients with pulmonary fibrosis, emphysema, combined pulmonary fibrosis and emphysema, bronchiectasis, cystic fibrosis and chronic obstructive lung disease (COPD).

Group 4—PH associated with chronic thromboembolism (CTEPH).

Group 5—PH associated with unclear or multifactoral etiologies. This category of PH patients shall be understood to encompass patients in one of the following groups: 1) chronic myeloproliferative disorders including polycythemia vera, essential thrombocythemia or chronic myeloid leukemia; 2) Systemic disorders including sarcoidosis, conditions resulting in destruction of the pulmonary capillary bed such as fibrosis, extrinsic compression of large pulmonary arteries, patients with Pulmonary Langerhan's cell histocytosis, lymphangioleiomyomatosis, neurofibromatosis type 1 and antineutrophil cytoplasmic antibodies-associated vasculitis; 3) Metabolic disorders including type Ia glycogen storage disease, deficiency of glucose-6-phosphatase, Gaucher disease and thyroid diseases (hypothyroidism and hyperthyroidism); 4) Encompassing patients with tumors that expand into the lumen of the pulmonary artery, occlusion of pulmonary microvasculature by metastatic tumor emboli, mediastinal fibrosis or patients with end-stage renal disease receiving long-term hemodialysis.

Fibrosis

Dysregulation of the TGFβ/BMP signaling pathways have been shown to have a causative role in fibrosis of various organs including kidney, heart, lung, skin, pancreas and liver, as well as in systemic sclerosis and associated pathologies (as reviewed by Leask and Abraham, FASEB, 2004). It has been shown that BMP7 counteracts TGFβ1-induced epithelial-mesenchymal transition (EMT) (Zeisberg, M et al. Nat. Med, 2003) and collagen induction (Izumi, N et al. AJP. Lung, Cell, Mol., Physiol. 2005) both key mechanisms in the development of fibrosis. Direct evidence for a role of Smurf-1 in fibrotic pathologies was demonstrated in the unilateral ureteral obstruction (UUO) mouse model of progressive tubulointerstitial fibrosis of the kidney where enhanced levels of Smurf-1 were present in the diseased kidneys associated with decreased levels of the protective Smurf-1 substrate, Smad7 (Fukasawa, H et al. PNAS, 2004). More recently, a role for Smurf-1 in pulmonary fibrosis was suggested in data generated in pulmonary epithelial cells identifying a crucial role for the Smurf-1 substrate Smad7 in limiting EMT (Shukla, M A, et al. Am. J. Resp. Cell. Mol. Biol. 2009). The compounds of the present invention disclosed herein are useful in the treatment of fibrosis and symptoms thereof. Fibrosis shall be understood to encompass the following: patients with pulmonary fibrosis, idiopathic pulmonary fibrosis, cystic fibrosis, cirrhosis, endomyocardial fibrosis, mediastinal fibrosis, myelofibrosis, retroperitoneal fibrosis, progressive massive fibrosis, nephrogenic systemic fibrosis, Crohn's Disease, keloid, old myocardial infarction, scleroderma (systemic sclerosis), arthrofibrosis or adhesive capsulitis.

Rheumatoid Arthritis

Pro-inflammatory cytokines such as tumor necrosis factor alpha (TNFα) play a key role in the onset and maintenance of chronic inflammatory conditions such as rheumatoid arthritis (RA). A reduction in bone density is commonly associated with RA and Smurf-1 has been shown to play a key role in mediating RA-induced bone loss. It was shown that TNFα triggered proteolytic degradation of the Smurf-1 substrates Smad1 and Runx2 both of which are essential for bone-forming osteoblast activity. Direct evidence in support of this link was demonstrated in smurf-1 KO mice where TNFα failed to impact osteoclast activity in bones from Smurf-1 KO mice but not those of corresponding wild-type mice (Guo, R et al. JBC, 2008). The compounds of the present invention disclosed herein are useful in the treatment of rheumatoid arthritis and symptoms thereof. RA shall be understood to encompass patients with chronic inflammation of the synovium secondary to swelling of synovial cells, excess synovial fluid and formation of fibrous tissue within joints. In addition, RA shall also encompass patients with RA due to a necrotizing granuloma, vasculitis, pyoderma gangrenosum, Sweet's syndrome, erythema nodosum, lobular panniculitis, atrophy of digital skin, palmar erythema or diffuse thinning of the skin. RA also extends to other organs and herein will encompass patients with fibrosis of the lungs, renal amyloidosis, atherosclerosis as a result of RA, pericarditis, endocarditis, left ventricular failure, valvulitis and fibrosis. RA will also encompass patients with ocular conditions of episcleritis and keratoconjunctivitis sicca, hematological disorders of warm autoimmune hemolytic anemia, neutropenia and thrombocytosis, neurological conditions of peripheral neuropathy, mononeuritis multiplex and carpal tunnel syndrome, osteoporosis and lymphoma.

Fracture Healing

The BMP pathway plays a role here and Smurf-1 inhibitors increase BMP signaling. The compounds of the present invention disclosed herein are useful in the treatment of fracture healing. Fracture healing shall be understood to encompass the technique of bone fracture repair whereby an endosteal implant containing pores into which osteoblasts and supporting connective tissue can migrate is surgically implanted at the site of bone fracture. The administration of inhibitors of Smurf-1 following insertion of the above described implant may aid integration of the implant and expedite recovery by enhancing proliferation of mesenchymal stem cells which differentiate into osteoblasts (Zhao, M et al. JBC, 2004).

Glaucoma

Elevated intraocular pressure (IOP) is one of the major risk factor for primary open angle glaucoma (POAG). IOP is maintained in anterior chamber by aqueous humor produced in ciliary body and outflowed through trabecular meshwork region. Increase aqueous humor outflow resistance associated with accumulation of extracellular matrix (ECM) deposition in trabecular meshwork region has been observed in glaucoma patients. This ECM pathology in POAG patients resembles fibrosis induced by TGFb proteins in many non-ocular systems. TGFb2 induced IOP increase was demonstrated in pre-clinical in vivo and ex vivo models. In several small scale clinical studies, the level of TGFb2 protein in aqueous humor has also been reported to be elevated in POAG patients. Modulating the TGFb activity in glaucoma patients could potentially lower IOP and lead to novel glaucoma therapies (Wordinger RJ JOURNAL OF OCULAR PHARMACOLOGY AND THERAPEUTICS Volume 30, Number 2, 2014). In view of the role of Smurf1 in the regulation of TGFb signaling through its substrates BMP9 and SMAD 7 the compounds of the present invention (or their pharmaceutically acceptable salts) described herein would be useful in the treatment of Glaucoma.

Hereditary Hemorrhagic Telangiectasia (HHT)

Hereditary Hemorrhagic Telangiectasia (HHT), also known as Osler-Weber-Rendu Syndrome, is a genetic disorder of the blood vessels affecting from 1:5000 to 1:40,000. A person with HHT has a tendency to form blood vessels that lack normal capillaries between an artery and vein, causing arterial blood under high pressure to flow directly into a vein, which may rupture and bleed. Symptoms of HHT may manifest as mild to severe, with 90-95% of patients experiencing nosebleeds by adulthood, 90-95% developing telangiectasias on the face or hands by middle age, and 40% developing lung arteriovenous malformations (AVM), which can pose significant risk. AVMs may also occur in the brain, liver, and intestine, with varying severity of health implications. HHT can be treated, most often with coagulation therapy, embolization, or surgical removal of affected tissue. HHT mutations cause haploinsufficiency in BMP signaling (Ricard et al. Blood, 2010) resulting in a vessel maturation defect and excessive branching of the vasculature which is in part, attributed to impaired BMP9 signaling (Choi, et al. PlosOne, 2013). Smurf1 down-regulates BMP signaling (Murakami Exp. Biol. Res. 2010 and Cao, et al. Sci. Rep. 2014) and has been reported to be expressed in the endothelial cells (Crose, et al. JBC, 2009 and Human Protein Atlas and GeneCards) and therefore, Smurf1 inhibitors may serve to restore BMP signaling and correct the angiogenesis abnormality. As such the compounds of the present invention (or their pharmaceutically acceptable salts) described herein would be useful in the treatment of HHT.

Proteinuria

Abnormal amounts of protein in the urine are one of the earliest signs of chronic kidney disease which can result from hypertension, diabetes or diseases associated with inflammation in the kidneys. If left untreated, chronic kidney disease may progress to end-stage renal disease and kidney failure. Smurf1 is involved in multiple mechanisms associated with kidney function and proteinuria. The Smurf1 substrate Ras homolog gene family, member A (RhoA), plays a critical role in regulating the migration of kidney podocytes. Synaptopodin enables stress fiber formation within kidney podocytes by blocking the ability of Smurf1 to bind to and ubiquitinate RhoA thus promoting podocyte motility and modulation of sieving properties of the podocyte filtration barrier of the kidney (Asanuma, et al. Nat. Cell Biol. 2006). Additionally, the intracellular antagonist of transforming growth factor (TGF) β, Smad7 plays a key protective role in the kidney. Smurf1 activity has been shown to ubiquitinate and degrade Smad7 leading to tubulointerstitial fibrosis and kidney dysfunction (Fukasawa, et al. PNAS 2004). Together, these reports suggest that a Smurf1 inhibitor may enable podocyte migration and maintenance of the podocyte filtration barrier in addition to blocking propagation of pro-fibrotic signaling with the kidney ultimately providing therapeutic benefit for proteinuria. Accordingly the compounds of the invention (or their pharmaceutically acceptable salts) would be useful in the treatment of proteinuria.

Wound Healing

Chronic non-healing wounds are most common in people over the age of 60 resulting in a significant amount of physical pain and are broadly classified into three groups: venous ulcers, diabetic and pressure ulcers. The precise timing of activity of the transforming growth factor (TGF) β and bone morphogenic protein (BMP) signaling pathways is essential in normal wound healing regulating key pro-healing processes of fibroblast migration and extracellular matrix deposition, inflammatory cell influx, angiogenesis and re-epithelialization (Pakyari, M et al. Adv. Wound Care 2013). Prolonged activation of TGF β may result in delayed wound healing and therapeutic intervention of established non-healing wounds with anti-TGF β antibodies results in improved healing and reduced scar hypertrophy (Lu et al. J. Am. Coll. Surg. 2005). Smurf1 regulates the extent of TGF β and BMP signaling (Murakami Exp. Biol. Res. 2010 and Cao, et al. Sci. Rep. 2014, Wang et al. J. Cell. Mol. Med. 2012) and therefore, it is anticipated that a Smurf1 inhibitor would normalized excessive of TGF β signaling enabling healing of chronic wounds. Accordingly the compounds of the invention (or their pharmaceutically acceptable salts) would be useful in the treatment of chronic non-healing wounds and/or wound healing generally.

COPD and Asthma

Airway remodeling is evident in patients with chronic obstructive pulmonary disease (COPD) or asthma. The predominant features of airway remodeling in asthma are fibrosis, thickening of basement membrane, increased goblet cell numbers and enhanced smooth muscle cell mass with enhanced contractile response which are thought to be induced by chronic inflammation responsible for airway hyper-responsiveness and reversible airway obstruction (Carroll et al. Am. Rev Resp. Dis. 1993, Metcalfe, et al. Physiol. Rev. 1997 and Roche, et al. Lancet 1989). In COPD lung remodeling is characterized by disorganization of the epithelium in the large airways with squamous metaplasia, goblet cell hyperplasia and mucus hypersecretion, and small airway remodeling with expansion of smooth muscle, fibrosis and alveolar destruction in the development of emphysema ultimately resulting in restriction of airflow (De, Decramer, et al. Lancet, 2012, Pain et al. Eur. Respir. Rev. 2014 and Chung, Proc. Am. Thorac. Soc. 2005). In both diseases, there is evidence of down-regulated BMP signaling (Kariyawasam, et al. Am. J Resp. Crit. Care Med. 2008) and elevated TGF β (Mak. Et al. Respir. Med. 2009 and Chakir et al. J. All. Clin. Immunol. 2003) linked to pro-remodelling mechanism such as fibroblast-mesenchymal transition (Araya, et al. J. Clin. Invest. 2007), extracellular matrix deposition (Baarsma, et al. Am. J. Physiol. Lung Cell Mol. Physiol. 2011) and inflammation (Chakir et al. J. All. Clin. Immunol. 2003). Smurf1 inhibitors may normalize TGF β signaling in critical pro-remodeling cells such as smooth muscle and fibroblasts and block progression of remodeling resulting in therapeutic benefit to COPD or asthma patients. Accordingly, the compounds of the invention (or their pharmaceutically acceptable salts) would be useful in the treatment of COPD and/or asthma.

Thus, as a further embodiment, the present invention provides the use of a compound of formula (I) or a pharmaceutically acceptable salt thereof in therapy. In a further embodiment, the therapy is selected from a disease which may be treated by inhibition of Smurf-1. In another embodiment, the disease is selected from the afore-mentioned list, suitably Pulmonary Hypertension, including Pulmonary arterial hypertension (PAH), Fibrosis, Rheumatoid Arthritis, and Fracture healing; more suitably Pulmonary arterial hypertension (PAH). In a yet further embodiment, the present invention provides the use of a compound of formula I or a pharmaceutically acceptable salt thereof, in the treatment of a disease selected from glaucoma, hereditary hemorrhagic telangiectasia (HHT), proteinuria, wound healing, COPD and asthma.

Thus, as a further embodiment, the present invention provides a compound of formula (I) or a pharmaceutically acceptable salt thereof, for use in therapy. In a further embodiment, the therapy is selected from a disease which may be treated by inhibition of Smurf-1. In another embodiment, the disease is selected from the afore-mentioned list, suitably Pulmonary Hypertension, including Pulmonary arterial hypertension (PAH), Fibrosis, Rheumatoid Arthritis, and Fracture healing; more suitably Pulmonary arterial hypertension (PAH). In another embodiment, the disease is selected from glaucoma, hereditary hemorrhagic telangiectasia (HHT), proteinuria, wound healing, COPD and asthma.

In another embodiment, the invention provides a method of treating a disease which is treated by inhibition of Smurf-1 comprising administration of a therapeutically acceptable amount of a compound of formula (I) or a pharmaceutically acceptable salt thereof. In a further embodiment, the disease is selected from the afore-mentioned list, suitably Pulmonary Hypertension, including Pulmonary arterial hypertension (PAH), Fibrosis, Rheumatoid Arthritis, and Fracture healing;
more suitably Pulmonary arterial hypertension (PAH).

In yet another embodiment, the invention provides a method of treating a disease via the inhibition of Smurf-1, said method comprising administration of a therapeutically acceptable amount of a compound of formula (I) or a pharmaceutically acceptable salt thereof, wherein the disease is selected from glaucoma, hereditary hemorrhagic telangiectasia (HHT), proteinuria, wound healing, COPD and asthma.

Thus, as a further embodiment, the present invention provides the use of a compound of formula (I) or a pharmaceutically acceptable salt thereof for the manufacture of a medicament. In a further embodiment, the medicament is for treatment of a disease which may be treated inhibition of Smurf-1. In another embodiment, the disease is selected from the afore-mentioned list, suitably Pulmonary Hypertension, including Pulmonary arterial hypertension (PAH), Fibrosis, Rheumatoid Arthritis, and Fracture healing;
more suitably Pulmonary arterial hypertension (PAH).

In yet another embodiment, the medicament is for treatment of a disease that is selected from glaucoma, hereditary hemorrhagic telangiectasia (HHT), proteinuria, wound healing, COPD and asthma.

In one embodiment of the present invention, there is provided N-(2-Cyclohexyl-1,5-dimethyl-3-oxo-2,3-dihydro-1H-pyrazol-4-yl)-4-methyl-5-((2R,3S)-3,5,5-trimethyl-1,4-dioxan-2-yl)isoxazole-3-carboxamide or a pharmaceutically acceptable salt or co-crystal thereof for use in the treatment of Pulmonary Hypertension, including Pulmonary arterial hypertension (PAH), Fibrosis, Rheumatoid Arthritis, and Fracture healing;
more suitably Pulmonary arterial hypertension (PAH).

In another embodiment of the present invention, there is provided N-(2-Cyclohexyl-1,5-dimethyl-3-oxo-2,3-dihydro-1H-pyrazol-4-yl)-4-methyl-5-((2R,3S)-3,5,5-trimethyl-1,4-dioxan-2-yl)isoxazole-3-carboxamide or a pharmaceutically acceptable salt thereof for use in the treatment of glaucoma, hereditary hemorrhagic telangiectasia (HHT), proteinuria, wound healing, COPD and asthma.

In another embodiment of the present invention, there is provided N-(2-Cyclohexyl-1,5-dimethyl-3-oxo-2,3-dihydro-1H-pyrazol-4-yl)-5-(5,5-dimethyl-1,3-dioxan-2-yl)-4-methylisoxazole-3-carboxamide or a pharmaceutically acceptable salt or co-crystal thereof for use in the treatment of Pulmonary Hypertension, including Pulmonary arterial hypertension (PAH), Fibrosis, Rheumatoid Arthritis, and Fracture healing;
more suitably Pulmonary arterial hypertension (PAH).

In yet another embodiment of the present invention, there is provided N-(2-Cyclohexyl-1,5-dimethyl-3-oxo-2,3-dihydro-1H-pyrazol-4-yl)-5-(5,5-dimethyl-1,3-dioxan-2-yl)-4-methylisoxazole-3-carboxamide or a pharmaceutically acceptable salt thereof for use in the treatment of glaucoma, hereditary hemorrhagic telangiectasia (HHT), proteinuria, wound healing, COPD and asthma.

In another embodiment of the present invention, there is provided N-(2-Cyclohexyl-1,5-dimethyl-3-oxo-2,3-dihydro-1H-pyrazol-4-yl)-5-(4,4-dimethylcyclohex-1-en-1-yl)-4-methylisoxazole-3-carboxamide or a pharmaceutically acceptable salt or co-crystal thereof for use in the treatment of Pulmonary Hypertension, including Pulmonary arterial hypertension (PAH), Fibrosis, Rheumatoid Arthritis, and Fracture healing;
more suitably Pulmonary arterial hypertension (PAH).

In still another embodiment of the present invention, there is provided N-(2-Cyclohexyl-1,5-dimethyl-3-oxo-2,3-dihydro-1H-pyrazol-4-yl)-5-(4,4-dimethylcyclohex-1-en-1-yl)-4-methylisoxazole-3-carboxamide or a pharmaceutically acceptable salt thereof for use in the treatment of glaucoma, hereditary hemorrhagic telangiectasia (HHT), proteinuria, wound healing, COPD and asthma.

In another embodiment of the present invention, there is provided [N-(2-Cyclohexyl-1,5-dimethyl-3-oxo-2,3-dihydro-1H-pyrazol-4-yl)-4-methyl-5-(1-oxaspiro[4.5]dec-7-en-8-yl)isoxazole-3-carboxamide] or a pharmaceutically acceptable salt or co-crystal thereof for use in the treatment of Pulmonary Hypertension, including Pulmonary arterial hypertension (PAH), Fibrosis, Rheumatoid Arthritis, and Fracture healing;
more suitably Pulmonary arterial hypertension (PAH).

In another embodiment of the present invention, there is provided [N-(2-Cyclohexyl-1,5-dimethyl-3-oxo-2,3-dihydro-1H-pyrazol-4-yl)-4-methyl-5-(1-oxaspiro[4.5]dec-7-en-8-yl)isoxazole-3-carboxamide] or a pharmaceutically acceptable salt thereof for use in the treatment of glaucoma, hereditary hemorrhagic telangiectasia (HHT), proteinuria, wound healing, COPD and asthma.

In another embodiment of the present invention, there is provided N-(2-Cyclohexyl-1,5-dimethyl-3-oxo-2,3-dihydro-1H-pyrazol-4-yl)-4-methyl-5-(1,4-dioxaspiro[4.5]decan-8-yl)isoxazole-3-carboxamide or a pharmaceutically acceptable salt or co-crystal thereof for use in the treatment of Pulmonary Hypertension, including Pulmonary arterial hypertension (PAH), Fibrosis, Rheumatoid Arthritis, and Fracture healing;
more suitably Pulmonary arterial hypertension (PAH).

In a further embodiment of the present invention, there is provided N-(2-Cyclohexyl-1,5-dimethyl-3-oxo-2,3-dihydro-1H-pyrazol-4-yl)-4-methyl-5-(1,4-dioxaspiro[4.5]decan-8-yl)isoxazole-3-carboxamide or a pharmaceutically acceptable salt thereof for use in the treatment of glaucoma, hereditary hemorrhagic telangiectasia (HHT), proteinuria, wound healing, COPD and asthma.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the following in vitro & in vivo methods.

Pharmaceutical Assay

Compounds of the invention and their pharmaceutically acceptable salts, hereinafter referred to alternatively as "agents of the invention", are useful as pharmaceuticals. In particular, the compounds are selective Smurf-1 inhibitors, and may be tested in the following assays.

To determine the HECT E3 ligase selectivity of the compounds, a panel of biochemical HECT E3 ligase autoubiquitinylation assays was employed (Smurf-1, Smurf-2, WWP1, WWP2, ITCH, Nedd4, Nedd4L and E6AP). The conjugation of ubiquitin to a protein substrate is a multistep process. In an initial ATP-requiring step, a thioester bond is formed between the carboxyl terminus of ubiquitin and an internal cystein residue of the ubiquitin-activating enzyme (E1). Activated ubiquitin is then transferred to a specific cystein residue of an ubiquitin-conjugating enzyme (E2). E2s donate ubiquitin to a HECT E3 ligase (E3) from which it is transferred to the substrate protein. HECT E3 ligases can auto-ubiquitinylate. This event is detected in the TR-FRET (Time-Resolved Fluorescence Resonance Energy Transfer) assay used in this panel. The reaction mix contains E1, E2, tagged-E3, biotin-conjugated ubiquitin, the compound and ATP in a suitable buffer and is incubated for 45 minutes to allow auto-ubiquitinylation of the E3 ligase. To measure the extent of ubiquitinylated E3 ligase by TR-FRET, the donor fluorophore Europium cryptate (Eu3+ cryptate), conjugated to streptavidin which subsequently binds to biotinylated ubiquitin, and the modified allophycocyanin XL665 (HTRF® primary acceptor fluorophore) coupled to a tag-specific antibody (HA, His or GST), which recognizes the respective E3 ligase fusion proteins, are added after the reaction is complete. When these two fluorophores are brought together by a bimolecular interaction (in this case ubiquitinylation of the E3 ligase), a portion of the energy captured by the Cryptate during excitation is released through fluorescence emission at 620 nm, while the remaining energy is transferred to XL665. This energy is then released by XL665 as specific fluorescence at 665 nm. Light at 665 nm is emitted only through FRET with Europium. Because Europium Cryptate is present in the assay, light at 620 nm is detected even when the bimolecular interaction does not bring XL665 within close proximity.

Autoubiquitinylation of Smurf-1 in cells leads to the proteasomal degradation of Smurf-1. Therefore, inhibition of the Smurf-1 catalytic domain abolishes Smurf-1 autoubiquitinylation and degradation, leading to accumulation of inhibited Smurf-1 protein in the cell.

Cellular activity of compounds at the Smurf-1 HECT domain is assessed by measuring the accumulation of Smurf-1 protein in HEK293 cells stably expressing Prolabel-tagged Smurf-1 under the control of a tetracycline-inducible promoter, using the DiscoverX PathHunter ProLabel Detection Kit. This technology measures the amount of Prolabel-tagged Smurf-1 in an enzyme complementation assay of the cell lysate. In this approach, a small 4 kDa complementing fragment of beta-galactosidase, called ProLabel, is expressed as an N-terminal fusion with human Smurf-1. This tag is the enzyme donor (ED) and enables detection of target protein levels after complementation with the larger portion of beta-galactosidase, termed EA for enzyme acceptor, to form functional beta-galactosidase enzyme. EA is exogenously added to the cell lysates. The enzyme activity is measured using a chemiluminescent substrate and is proportional to the amount of reconstituted enzyme and hence Smurf-1 levels.

Test and reference compounds are prepared at 180× [final] in 90% DMSO, and diluted 1:3 in 90% DMSO.

For the biochemical assay panel, 50 nl of the test compounds, reference compounds and buffer/DMSO control are transferred to the respective wells of a 384-well white GREINER "SMALL VOLUME" PS plate. The assay panel is run at room temperature on a Biomek FX liquid handling workstation. To the assay plates containing 50 nl compound or control solutions in 90% DMSO, 4.5 ul of E3 ligase solution were added per well, followed by 4.5 ul of the pre-incubated E1/E2/Ub mix or the pre-diluted ubiquitin (LOW control). Plates are shaken vigorously after each addition. In this assay the compound concentrations range from 3 nM to 10 uM in an 8-point dose-response curve.

After 45 min of incubation the ubiquitinylation reactions were stopped by adding 4.5 ul 2 mM NEM, immediately followed by 4.5 ul of a detection solution including the XL665-labeled antibody and the streptavidin-coupled europium to give a total volume of 18 ul. After an incubation time of 45 min in the dark, the plates are transferred into the Pherastar fluorescence reader to measure the TR-FRET signal.

For the cellular assay 250 nl of the test compounds, reference compounds and buffer/DMSO control are then transferred to the respective wells of a sterile 120 ul 384-well white GREINER PS, CELLSTAR, uClear tissue culture plate. To distribute the compound solution evenly in the medium before adding the cells, 10 ul of cell culture medium are added to each well of the compound containing plate using the MULTIDROP 384 dispenser and shaken vigorously. Cells are detached from the flask after a short incubation with trypsin-EDTA, counted and diluted to a concentration of $1.5 \times 10^6$ cells/ml in culture medium. The expression of Smurf-1 is induced by adding doxycyline to a final concentration of 0.2 ug/ml. 10 ul of the cell suspension are added to each well of the compound-containing plates by using the MULTIDROP 384 dispenser. The plates are incubated over night at 37° C., 5% $CO_2$. In this assay the compound concentrations range from 6.75 nM to 22.5 uM in an 8-point dose-response curve.

After overnight incubation with the compounds the levels of Smurf-1 are determined using the PathHunter Prolabel detection kit from DiscoverX. First 10 ul of a lysis/CL detection working solution are added manually using a multi-channel step-pipettor, followed by the addition of 5 ul enzyme acceptor EA. The plates are mixed on a plate shaker and incubated for 2-3 hours at room-temperature before measuring the chemiluminescent signal in the PherStar plate reader.

Compounds of the Examples, herein below, have Smurf-1 $IC_{50}$ values in the data measurements described above as shown in Table A.

TABLE A

| Example | Smurf-1/IC50 nM |
| --- | --- |
| 1 | 2.8 |
| 1.1 | 2.1 |
| 1.2 | 14 |
| 1.3 | 1.8 |
| 1.4 | 3.2 |
| 1.5 | 6.0 |
| 1.6 | 8.0 |
| 1.7 | 33 |
| 2 | 2.5 |
| 2.1 | 64 |
| 2.2 | 0.9 |
| 3 | 6.0 |
| 4 | 100 |
| 5 | 310 |
| 6 | 5.7 |
| 6.1 | 23 |
| 7 | 19 |
| 8 | 46 |
| 9 | 58 |
| 10 | 50 |
| 11 | 420 |
| 12 | 100 |
| 13 | 640 |
| 13a | 290 |
| 13b | 730 |
| 14 | 2500 |
| 15a | 290 |
| 15b | 630 |
| 16 | 37 |
| 17 | 980 |
| 18 | 91 |
| 19 | 1800 |
| 20 | 180 |
| 21.1 | 630 |
| 21.2 | 490 |
| 22 | 570 |
| 22a | 420 |
| 22b | 5100 |
| 22c | 1.4 |
| 23 | 160 |
| 24 | 340 |
| 24a | 350 |
| 24b | 250 |
| 25a | 160 |
| 25b | 75 |
| 25c | 840 |
| 25d | 74 |
| 26 | 580 |

The compound of the present invention may be administered either simultaneously with, or before or after, one or more other therapeutic agent. The compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the invention.

In one embodiment, the invention provides a product comprising a compound of formula (I) or a pharmaceutically acceptable salt thereof and at least one other therapeutic agent as a combined preparation for simultaneous, separate or sequential use in therapy. In one embodiment, the therapy is the treatment of a disease or condition mediated by Smurf-1. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) or a pharmaceutically acceptable salt thereof and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of formula (I) or a pharmaceutically acceptable salt thereof. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) or a pharmaceutically acceptable salt thereof for treating a disease or condition mediated by Smurf-1, wherein the medicament is prepared for administration with another therapeutic agent. The invention also provides the use of another therapeutic agent for treating a disease or condition mediated by Smurf-1, wherein the medicament is administered with a compound of formula (I) or a pharmaceutically acceptable salt thereof.

The invention also provides a compound of formula (I) or a pharmaceutically acceptable salt thereof for use in a method of treating a disease or condition mediated by Smurf-1, wherein the compound of formula (I) or a pharmaceutically acceptable salt thereof is prepared for administration with another therapeutic agent. The invention also provides another therapeutic agent for use in a method of treating a disease or condition mediated by Smurf-1, wherein the other therapeutic agent is prepared for administration with a compound of formula (I) or a pharmaceutically acceptable salt thereof. The invention also provides a compound of formula (I) for use in a method of treating a disease or condition mediated by Smurf-1, wherein the compound of formula (I) or a pharmaceutically acceptable salt thereof is administered with another therapeutic agent. The invention also provides another therapeutic agent for use in a method of treating a disease or condition mediated by Smurf-1, wherein the other therapeutic agent is administered with a compound of formula (I) or a pharmaceutically acceptable salt thereof.

The invention also provides the use of a compound of formula (I) or a pharmaceutically acceptable salt thereof for treating a disease or condition mediated by Smurf-1, wherein the patient has previously (e.g. within 24 hours) been treated with another therapeutic agent. The invention also provides the use of another therapeutic agent for treating a disease or condition mediated by Smurf-1, wherein the patient has previously (e.g. within 24 hours) been treated with a compound of formula (I) or a pharmaceutically acceptable salt thereof.

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art. Further, the compounds of the present invention can be produced by organic synthesis methods known to one of ordinary skill in the art as shown in the following examples.

General Conditions:

Mass spectra were acquired on LC-MS, SFC-MS, or GC-MS systems using electrospray, chemical and electron impact ionization methods from a range of instruments of the following configurations: Agilent 1100 HPLC systems with an Agilent 6110 Mass Spectrometer [M+H]+ refers to protonated molecular ion of the chemical species.

NMR spectra were run on Bruker AVANCE 400 MHz or 500 MHz NMR spectrometers using ICON-NMR, under TopSpin program control. Spectra were measured at 298K, unless indicated otherwise, and were referenced relative to the solvent resonance.

Instrumentation

MS Methods: Using Agilent 1100 HPLC systems with an Agilent 6110 Mass Spectrometer LowpH v002
 Column Phenomenex Gemini C18 50×4.6 mm, 3.0 μm
 Column Temperature 50° C.
 Eluents A: $H_2O$, B: methanol, both containing 0.1% TFA
 Flow Rate 1.0 ml/min
 Gradient 5% to 95% B in 2.0 min, 0.2 min 95% B 2minLC v003
 Column Waters BEH C18 50×2.1 mm, 1.7 μm
 Column Temperature 50° C.
 Eluents A: $H_2O$, B: acetonitrile, both containing 0.1% TFA
 Flow Rate 0.8 ml/min
 Gradient 0.20 min 5% B; 5% to 95% B in 1.30 min, 0.25 min 95% B 8minLowpHv01:
 Column: Waters Acquity CSH 1.7 μm, 2.1×100 mm
 Temperature: 50° C.
 Mobile Phase: A: Water+0.1% Formic Acid B: Acetonitrile+0.1% Formic Acid
 Flow rate: 0.7 mL/min
 Gradient: 0.0 min 2% B, 0.3-6.5 min 2-98% B, 6.5-7.5 min 98% B, 7.5-8.0 min 5-98% B 2minLowpH:
 Column: Waters Acquity CSH 1.7 μm, 2.1×50 mm
 Temperature: 50° C.
 Mobile Phase: A: Water+0.1% Formic Acid B: Acetonitrile+0.1% Formic Acid
 Flow rate: 1.0 mL/min
 Gradient: 0.0 min 5% B, 0.2-1.3 min 5-98% B, 1.3-1.55-1.6 min 98-5% B 2minLowpHv01:
 Column: Waters Acquity CSH 1.7 μm, 2.1×50 mm
 Temperature: 50° C.
 Mobile Phase: A: Water+0.1% Formic Acid B: Acetonitrile+0.1% Formic Acid
 Flow rate: 1.0 mL/min
 Gradient: 0.0 min 5% B, 0.2-1.55 min 5-98% B, 1.55-1.75 min 98% B, 1.75-1.8 min 98-5% B 2minLowpHv03:
 Column: Waters Acquity CSH 1.7 μm, 2.1×50 mm
 Temperature: 50° C.
 Mobile Phase: A: Water+0.1% Formic Acid B: Acetonitrile+0.1% Formic Acid
 Flow rate: 1.0 mL/min
 Gradient: 0.0 min 5% B, 0.2-1.8 min 5-98% B, 1.8-2.1 min 98% B, 2.1-2.3 min 98% B 2minHighpHv03:
 Column: Waters Acquity CSH 1.7 μm, 2.1×50 mm
 Temperature: 50° C.
 Mobile Phase: A: Water+0.1% Ammonia B: Acetonitrile+0.1% Ammonia
 Flow rate: 1.0 mL/min
 Gradient: 0.0 min 5% B, 0.2-1.8 min 5-98% B, 1.8-2.1 min 98% B, 2.1-2.3 min 98-5% B 10minLowpHv01:
 Column: Waters Acquity CSH 1.7 μm, 2.1×100 mm
 Temperature: 50° C.
 Mobile Phase: A: Water+0.1% Formic Acid B: Acetonitrile+0.1% Formic Acid
 Flow rate: 0.7 mL/min
 Gradient: 0.0 min 2% B, 0.5-8.0 min 2-98% B, 8.0-9.0 min 98% B, 9.0-9.1 min 98-2% B LCMS (SRPb)
 Column: Acquity HSS T3 2.1×50 mm, 1.8 micron
 Column Temperature: 60° C.
 Eluents: A: H2O (0.05% formic acid, 3.75 mM ammonium acetate)
 B: acetonitrile (0.05% formic acid)
 Flow Rate: 1.0 ml/min
 Gradient 5% to 98% in 1.4 min Abbreviations aq aqueous
br broad
d doublet
dd doublet of doublets
DBU 1,8-Diazabicycloundec-7-ene
DCM dichloromethane
DIBAL-H diisobutylaluminum hydride
DIPEA diethylisopropylamine
DME Dimethoxyethane
DMF N,N-dimethylformamide
DMSO dimethylsulfoxide
° C. degrees Celsius
EDCl 1-Ethyl-3-(3-dimethylaminopropyl)carbodiimide
$Et_2O$ diethylether
EtOAc ethyl acetate
EtOH ethanol
$Et_3N$ triethylamine HATU (1-[Bis(dimethylamino)methylene]-1H-1,2,3-triazolo[4,5-b]pyridinium 3-oxide hexafluorophosphate HCl hydrochloric acid hr (s) hour(s)

$H_2SO_4$ sulfuric acid $K_2CO_3$ Potassium Carbonate

KHMDS Potassium bis(trimethylsilyl)amide KOAc potassium acetate

LCMS liquid chromatography and mass spectrometry

LDA lithium diisopropylamide

M molar $MgSO_4$ magnesium sulfate

MeCN acetonitrile

MeOH methanol

MS mass spectrometry

Mult(s) multiplet(s)

mg milligram min minutes ml milliliter mmol millimol m/z mass to charge ratio $NaBH_4$ sodium borohydride NaH sodium hydride $NaHCO_3$ sodium hydrogen carbonate NaOH sodium hydroxide $Na_2SO_4$ sodium sulfate n-BuLi butyllithium $NH_4Cl$ ammonium chloride NMP N-methylpyrrolidone NMR nuclear magnetic resonance $PdCl_2(PPh_3)_2$ Palladium(bis triphenylphosphine)dichloride $PdCl_2$(dppf) 1,1'-Bis(diphenylphosphino)ferrocene-palladium(II)dichloride $PdCl_2$(dppf)-$CH_2Cl_2$ 1,1'-Bis(diphenylphosphino)ferrocene-palladium(II)dichloride dichloromethane complex $Pd(Ph_3P)_4$ Tetrakis(triphenylphosphine)palladium(0)

ppm parts per million pTsOH p-Toluenesulfonic acid q quartet rac racemic

Rt retention time s singlet t triplet

TBAI tetrabutylammonium iodide

TBAF tetrabutylammonium fluoride

TBME methyl tert-butyl ether

TFA trifluoroacetic acid

THF tetrahydrofuran

TMSCl trimethylsilyl chloride

TMSOTf trimethylsilyl triflate

UV ultra-violet

Preparation of Final Compounds

Example 1

[N-(2-Cyclohexyl-1,5-dimethyl-3-oxo-2,3-dihydro-1H-pyrazol-4-yl)-5-(4-isopropylcyclohex-1-en-1-yl)-4-methylisoxazole-3-carboxamide]

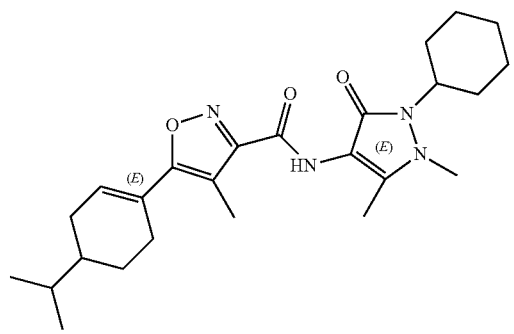 [SMILES: Cc1c(C(=O)Nc2c(C)n(C)n(C3CCCCC3)c2=O)noc1C1=CCC(C(C)C)CC1]

Step 1: [4-Isopropylcyclohex-1-en-1-yl trifluoromethanesulfonate]

A solution of 4-isopropylcyclohexanone (1 g, 7.13 mmol) in dry THF (3 mL) under nitrogen and cooled to −70° C. was treated dropwise with 2M LDA (in THF/heptane/ethylbenzene) (4.28 mL, 8.56 mmol). After addition was complete the mixture was allowed to stir at −70° C. for 1.5 hours. To the mixture was added a solution of 1,1,1-trifluoro-N-(pyridin-2-yl)-N-((trifluoromethyl)sulfonyl)methanesulfonamide (2.81 g, 7.84 mmol) in dry THF (2 mL). The reaction was maintained at −70° C., stirred for 3 hrs and quenched carefully with water and left to stand overnight. The resulting mixture was extracted with diethyl ether and the combined organic extracts were washed with 10% NaOH (aq), dried over $MgSO_4$ and filtered. The solvent was removed under reduced pressure to afford crude material. The crude material was adsorbed onto silica and purification by chromatography eluting with 100% iso-hexane afforded the title compound;

$^1$H NMR (400 MHz, $CDCl_3$) δ 5.76 (1H, t), 2.45-2.30 (2H, mults), 2.22 (1H, br d), 1.99-1.90 (2H, mults), 1.61-1.52 (1H, mult), 1.48-1.36 (2H, mults), 0.93 (6H, dd).

Step 2: [2-(4-Isopropylcyclohex-1-en-1-yl)-4,4,5,5-tetramethyl-1,3,2-dioxaborolane]

A stirred solution of [4-isopropylcyclohex-1-en-1-yl trifluoromethanesulfonate] (1.75 g, 6.43 mmol) in dioxane (30 mL) was treated with bispinacolatodiboron (1.714 g, 6.75 mmol), potassium acetate (1.892 g, 19.28 mmol) and $PdCl_2$(dppf).$CH_2Cl_2$ adduct (0.157 g, 0.193 mmol) and the mixture was stirred at 80° C. for 6 hrs. The resulting mixture was diluted with EtOAc and washed with water. The organic layer was dried over $MgSO_4$, filtered and concentrated under reduced pressure to afford crude material. The crude material was adsorbed onto silica and purification by chromatography eluting with 0-30% EtOAc in iso-hexane afforded the title compound.

Step 3: [Ethyl 5-(4-isopropylcyclohex-1-en-1-yl)-4-methylisoxazole-3-carboxylate]

To a 2-5 mL microwave vial was added [2-(4-isopropylcyclohex-1-en-1-yl)-4,4,5,5-tetramethyl-1,3,2-dioxaborolane] (282 mg, 1.127 mmol), ethyl 5-bromo-4-methylisoxazole-3-carboxylate (Intermediate A) (264 mg, 1.127 mmol), $PdCl_2$ (dppf) (82 mg, 0.113 mmol), potassium carbonate (467 mg, 3.38 mmol), MeCN (2 mL) and water (0.667 mL). The vial was evacuated with nitrogen, sealed and placed in the microwave at 80° C. for 1 hr. The resulting mixture was diluted with EtOAc and water and the layers were separated. The organics were dried over $MgSO_4$, filtered and concentrated under reduced pressure to give a brown oil, crude. The crude material was adsorbed onto silica and purification by chromatography eluting with 0-10% EtOAc in iso-hexane afforded the title compound;
LC-MS: Rt=1.73 mins; MS m/z [M+H]+278.5; Method 2minLowpHv03

Step 4: [5-(4-Isopropylcyclohex-1-en-1-yl)-4-methylisoxazole-3-carboxylic acid]

To a solution of [ethyl 5-(4-isopropylcyclohex-1-en-1-yl)-4-methylisoxazole-3-carboxylate] (92 mg, 0.332 mmol) in THF (5 mL) and MeOH (3 mL) was added 2M sodium hydroxide (aq) (0.166 mL, 0.332 mmol) and the mixture was stirred at room temperature for 2 hrs. The resulting mixture was concentrated under reduced pressure and diluted with water. The aqueous layer was washed with EtOAc, acidified with 2M HCl (aq) and extracted with EtOAc. The organic extracts were dried over $MgSO_4$, filtered and concentrated under reduced pressure to afford the title compound;
LC-MS: Rt=1.70 mins; MS m/z [M+H]+250.2; Method 2minLowpHv03

Step 5: [N-(2-Cyclohexyl-1,5-dimethyl-3-oxo-2,3-dihydro-1H-pyrazol-4-yl)-5-(4-isopropylcyclohex-1-en-1-yl)-4-methylisoxazole-3-carboxamide]

To a solution of [5-(4-isopropylcyclohex-1-en-1-yl)-4-methylisoxazole-3-carboxylic acid] (42 mg, 0.168 mmol) in dry DCM (3 mL) under nitrogen was added DMF (0.026 mL, 0.337 mmol) followed by oxalyl chloride (0.016 mL, 0.185 mmol) and the mixture was stirred at room temperature for 30 mins. 4-Amino-2-cyclohexyl-1,5-dimethyl-1H-pyrazol-3(2H)-one (Intermediate D) (38.8 mg, 0.185 mmol) was added followed by triethylamine (0.070 mL, 0.505 mmol) and the mixture was stirred for 30 mins. Water was added and the mixture was stirred vigorously before passing through a phase separating cartridge. The organic eluent was collected and concentrated under reduced pressure to give an orange oil. The crude material was dissolved in DMSO (0.9 mL) and purified using mass-directed automated reverse phase chromatography over a 9.5 minute gradient of 50-98% MeCN in water (0.1% formic acid). The product fraction was concentrated under reduced pressure. The remaining aqueous was treated with a saturated aqueous solution of sodium hydrogen carbonate and extracted with DCM, passing the organic extracts through a phase separating cartridge. The solvent was removed under a stream of air and dried under reduced pressure to afford the title compound;
LC-MS: Rt=4.98 mins; MS m/z [M+H]+441.4; Method 8minLowpHv01
$^1$H NMR (400 MHz, $CDCl_3$) δ 8.04 (1H, br s), 6.33 (1H, s), 4.06 (1H, tt), 3.26 (3H, s), 2.62 (1H, br d), 2.48-2.35 (2H, mults), 2.31 (3H, s), 2.22 (3H, s), 2.05-1.86 (8H, mults), 1.71 (1H, br d), 1.60-1.52 (1H, mults), 1.43-1.17 (5H, mults), 0.96 (3H, d), 0.94 (3H, d).

Examples 1.1 to 1.2 were prepared by a similar method to that of Example 1 by replacing 4-isopropylcyclohexanone (Step 1) with the appropriate ketone derivative (either commercially available or preparations described hereinafter).

Example 1.1

A diastereomeric mixture of N-(2-Cyclohexyl-1,5-dimethyl-3-oxo-2,3-dihydro-1H-pyrazol-4-yl)-5-(6-ethyl-4-methylcyclohex-1-en-1-yl)-4-methylisoxazole-3-carboxamide

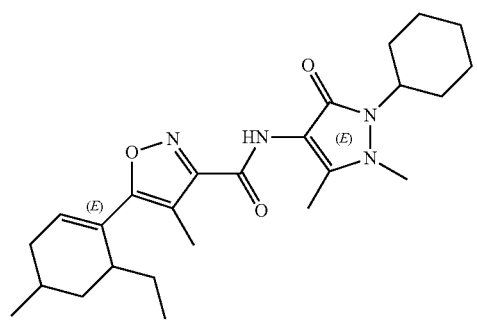 [SMILES: CCC1CC(C)CC=C1c1onc(C(=O)Nc2c(C)n(C)n(C3CCCCC3)c2=O)c1C]

LC-MS: Rt=4.90 mins; MS m/z [M+H]+441.1; Method 8minLowpHv01

Example 1.2

N-(2-Cyclohexyl-1,5-dimethyl-3-oxo-2,3-dihydro-1H-pyrazol-4-yl)-5-(6,6-dimethylcyclohex-1-en-1-yl)-4-methylisoxazole-3-carboxamide

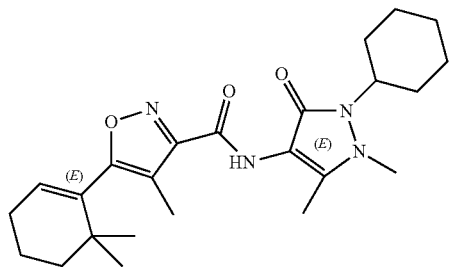 [SMILES: Cc1c(C(=O)Nc2c(C)n(C)n(C3CCCCC3)c2=O)noc1C1=CCCCC1(C)C]

LC-MS: Rt=4.60 mins; MS m/z [M+H]+427.7; Method 8minLowpHv01

Examples 1.3 to 1.7 were prepared by a similar method to that of Example 1 by replacing 2-(4-isopropylcyclohex-1-en-1-yl)-4,4,5,5-tetramethyl-1,3,2-dioxaborolane (Step 3) with the appropriate boronic acid or dioxaborolane derivative (either commercially available or preparations described hereinafter).

Example 1.3

[N-(2-Cyclohexyl-1,5-dimethyl-3-oxo-2,3-dihydro-1H-pyrazol-4-yl)-5-(4-ethylcyclohex-1-en-1-yl)-4-methylisoxazole-3-carboxamide]

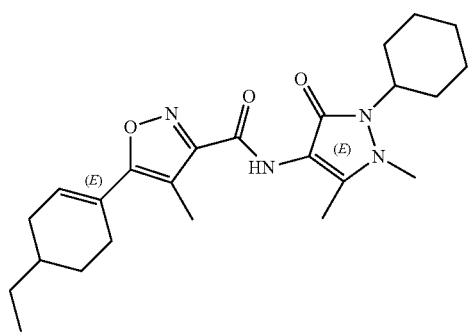 [SMILES: CCC1CC=C(c2onc(C(=O)Nc3c(C)n(C)n(C4CCCCC4)c3=O)c2C)CC1]

LC-MS: Rt=4.77 mins; MS m/z [M+H]+427.6; Method 8minLowpHv01

Example 1.4

[5-(4-(tert-Butyl)cyclohex-1-en-1-yl)-N-(2-cyclohexyl-1,5-dimethyl-3-oxo-2,3-dihydro-1H-pyrazol-4-yl)-4-methylisoxazole-3-carboxamide]

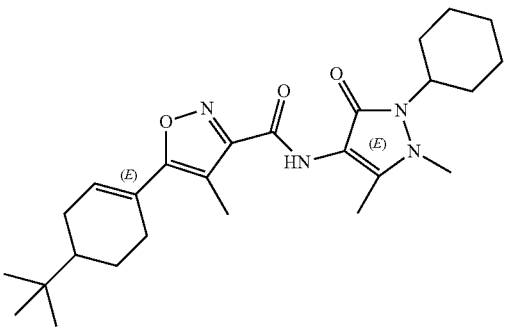 [SMILES: Cc1c(C(=O)Nc2c(C)n(C)n(C3CCCCC3)c2=O)noc1C1=CCC(C(C)(C)C)CC1]

LC-MS: Rt=5.16 mins; MS m/z [M+H]+455.4; Method 8minLowpHv01

Example 1.5

[N-(2-Cyclohexyl-1,5-dimethyl-3-oxo-2,3-dihydro-1H-pyrazol-4-yl)-4-methyl-5-(4-methylcyclohex-1-en-1-yl)isoxazole-3-carboxamide]

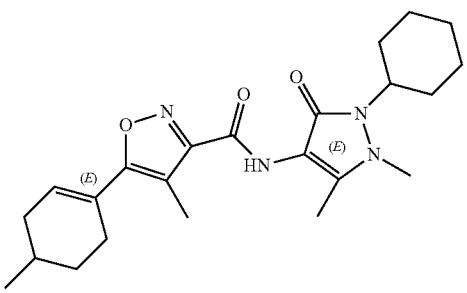 [SMILES: Cc1c(C(=O)Nc2c(C)n(C)n(C3CCCCC3)c2=O)noc1C1=CCC(C)CC1]

LC-MS: Rt=4.47 mins; MS m/z [M+H]+414.5; Method 8minLowpHv01

Example 1.6

5-(Cyclohept-1-en-1-yl)-N-(2-cyclohexyl-1,5-dimethyl-3-oxo-2,3-dihydro-1H-pyrazol-4-yl)-4-methyl-isoxazole-3-carboxamide

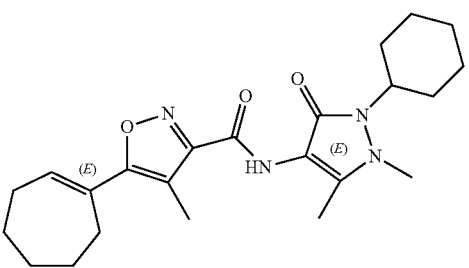 [SMILES: Cc1c(C(=O)Nc2c(C)n(C)n(C3CCCCC3)c2=O)noc1C1=CCCCCC1]

Example 1.7

[N-(2-Cyclohexyl-1,5-dimethyl-3-oxo-2,3-dihydro-1H-pyrazol-4-yl)-4-methyl-5-(4-(trifluoromethyl)cyclohex-1-en-1-yl)isoxazole-3-carboxamide]

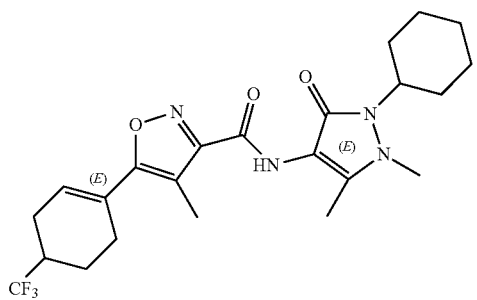 [SMILES: Cc1c(C(=O)Nc2c(C)n(C)n(C3CCCCC3)c2=O)noc1C1=CCC(C(F)(F)F)CC1]

LC-MS: Rt=1.36 mins; MS m/z [M+H]+467.4; Method 2minLowpHv03

Example 2

N-(2-Cyclohexyl-1,5-dimethyl-3-oxo-2,3-dihydro-1H-pyrazol-4-yl)-4-methyl-5-(spiro[4.5]dec-7-en-8-yl)isoxazole-3-carboxamide

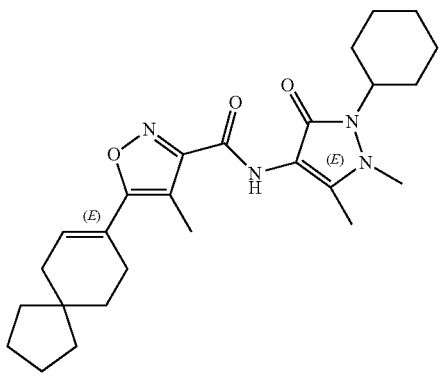 [SMILES: Cc1c(C(=O)Nc2c(C)n(C)n(C3CCCCC3)c2=O)noc1C1=CCC2(CCCC2)CC1]

Step 1: Spiro[4.5]dec-6-en-8-one

To a solution of cyclopentanecarbaldehyde (Aldrich) (0.82 g, 8.36 mmol) in dry toluene (10 mL), methyl vinyl ketone (Alfa Aesar) (0.684 mL, 8.36 mmol) was added followed by a catalytic amount of concentrated $H_2SO_4$ (0.045 mL, 0.836 mmol). The mixture was heated at 45° C. for 1.5 hours, then refluxed for 1 hour using a Dean-Stark trap. The reaction mixture was cooled to room temperature and further methyl vinyl ketone (Alfa Aesar) (0.684 mL, 8.36 mmol) was added. The reaction mixture was heated at reflux for 1 hour, allowed to cool to room temperature and treated with an aqueous 1M $NaHCO_3$ (30 mL) solution. The aqueous was extracted with toluene and the combined organic extracts were washed with brine, dried over $MgSO_4$, filtered and concentrated under reduced pressure. The crude material was adsorbed onto silica and purification by chromatography eluting with 0-20% EtOAc in iso-hexane afforded the title compound;

$^1$H NMR (400 MHz, $CDCl_3$) δ 6.74 (1H, d), 5.86 (1H, d), 2.45 (2H, t), 1.92 (2H, t), 1.80-1.71 (4H, br mults), 1.71-1.61 (4H, br mults).

Step 2: Spiro[4.5]decan-8-one

A solution of spiro[4.5]dec-6-en-8-one (442 mg, 2.94 mmol) in ethanol (15 mL) was flushed with nitrogen and treated with 10% Pd—C, 50% wet (Alfa Aesar, 38303) (313 mg, 2.94 mmol). The reaction mixture was stirred for 16 hours under an atmosphere of hydrogen and filtered through Celite®, rinsing with ethanol. The filtrate was concentrated under reduced pressure to afford the title compound;

$^1$H NMR (400 MHz, $CDCl_3$) δ 2.31-2.25 (4H, t), 1.72-1.66 (4H, t), 1.65-1.60 (4H, br mults), 1.53-1.47 (4H, br mults).

Step 3: Spiro[4.5]dec-7-en-8-yl trifluoromethanesulfonate 1.6M n-BuLi in hexane (1.900 mL, 3.04 mmol) was added to a stirred solution of diisopropylamine (0.454 mL, 3.19 mmol) in dry THF (20 mL) under nitrogen at −78° C. The solution was allowed to warm to 0° C. for 20 minutes before re-cooling to −78° C. A solution of spiro[4.5]decan-8-one (0.440 g, 2.89 mmol) in dry THF (5 mL) was added over 5 minutes and the solution was stirred at −78° C. for 50 minutes before adding a solution of 2-[N,N-Bis(trifluoromethylsulfonyl)amino]pyridine (Alfa Aesar) (1.141 g, 3.19 mmol) in dry THF (5 mL). The mixture was stirred and allowed to warm to room temperature overnight. The resulting mixture was quenched with saturated aqueous $NaHCO_3$ (4 mL). The aqueous portion was extracted with TBME (×2) and the combined organic extracts were washed with 10% aqueous NaOH, brine, dried over $MgSO_4$, filtered and concentrated under reduced pressure. The crude material was adsorbed onto silica and purification by chromatography eluting with 0-30% EtOAc in iso-hexane afforded the title compound.

Step 4: 4,4,5,5-Tetramethyl-2-(spiro[4.5]dec-7-en-8-yl)-1,3,2-dioxaborolane

To a stirred solution of spiro[4.5]dec-7-en-8-yl trifluoromethanesulfonate (635 mg, 2.234 mmoL) in dry 1,4-dioxane (15 mL), bis(pinacolato)diboron (Alfa Aesar) (567 mg, 2.234 mmol) was added followed by potassium acetate (Acros) (438 mg, 4.47 mmoL) and $PdCl_2(dppf).CH_2Cl_2$ adduct (Alfa Aesar) (54.7 mg, 0.067 mmoL). The reaction mixture was flushed with nitrogen and heated to 80° C. for 16 hours. The reaction mixture was cooled to room temperature and filtered through Celite®, rinsing with TBME. The filtrate was concentrated under reduced pressure and the residue partitioned between EtOAc (50 mL) and water (50 mL). The organic phase was washed with brine (30 mL), dried over $MgSO_4$, filtered and concentrated under reduced pressure. The crude material was adsorbed onto silica and purification by chromatography eluting with 0-30% EtOAc in iso-hexane afforded the title compound.

Step 5: Ethyl 4-methyl-5-(spiro[4.5]dec-7-en-8-yl)isoxazole-3-carboxylate

To a 2-5 mL microwave vial containing a solution of 4,4,5,5-tetramethyl-2-(spiro[4.5]dec-7-en-8-yl)-1,3,2-dioxaborolane (168 mg, 0.641 mmol) in MeCN (2 mL), ethyl 5-bromo-4-methylisoxazole-3-carboxylate (Intermediate A)

(150 mg, 0.641 mmol) was added followed by K₂CO₃ (266 mg, 1.923 mmol), PdCl₂(dppf).CH₂Cl₂ adduct (Alfa Aesar) (52.3 mg, 0.064 mmol) and water (1 mL). The vial was flushed with nitrogen, sealed and treated in the microwave (Biotage Smith Initiator) at 90° C. for 1 hour. The reaction mixture was partitioned between water (20 mL) and EtOAc (20 mL) and the organic phase was washed with brine (20 mL), dried over MgSO₄, filtered and concentrated under reduced pressure to give an orange oil. The crude material was adsorbed onto silica and purification by chromatography eluting with 0-30% EtOAc in iso-hexane afforded the title compound;

LC-MS: Rt=1.75 mins; MS m/z [M+H]+290.4; Method 2minLowpHv03

Step 6: 4-Methyl-5-(spiro[4.5]dec-7-en-8-yl)isoxazole-3-carboxylic acid

To a stirred solution of ethyl 4-methyl-5-(spiro[4.5]dec-7-en-8-yl)isoxazole-3-carboxylate (180 mg, 0.622 mmol) in ethanol (10 mL), 2M NaOH (aq) (0.311 mL, 0.622 mmol) was added and the reaction mixture was stirred at room temperature. The resulting mixture was diluted with water (30 mL) and acidified to pH 5-6 by the addition of 2M HCl (aq). The aqueous was extracted with EtOAc (2×20 mL) and the combined organic extracts were washed with brine (20 mL), dried over MgSO₄, filtered and concentrated under reduced pressure to afford the title compound;

LC-MS: Rt=1.61 mins; MS m/z [M+H]+262.3; Method 2minLowpHv03

Step 7: N-(2-Cyclohexyl-1,5-dimethyl-3-oxo-2,3-dihydro-1H-pyrazol-4-yl)-4-methyl-5-(spiro[4.5]dec-7-en-8-yl)isoxazole-3-carboxamide To a stirred solution of 4-methyl-5-(spiro[4.5]dec-7-en-8-yl)isoxazole-3-carboxylic acid (95 mg, 0.364 mmol) in dry NMP (3 ml), HATU (152 mg, 0.400 mmol) was added followed by 4-amino-2-cyclohexyl-1,5-dimethyl-1H-pyrazol-3(2H)-one (Intermediate D) (84 mg, 0.400 mmol) and triethylamine (0.111 mL, 0.800 mmol) and this was stirred at room temperature for 16 hours. The reaction mixture was partitioned between EtOAc (30 mL) and 1M NaOH (aq) (30 mL) and the organic phase was washed with water (30 mL), brine (30 mL), dried over MgSO₄, filtered and concentrated under reduced pressure to give an orange oil. The crude material was dissolved in DMSO and purified using UV-directed automated reverse phase chromatography over a 9.5 minute gradient of 50-98% MeCN in water (0.1% formic acid). The product fraction was added to EtOAc (50 mL) and washed with a saturated aqueous NaHCO₃ solution (50 mL). The organic extracts were dried over MgSO₄, filtered and concentrated under reduced pressure to afford the title compound;

LC-MS: Rt=1.59 mins; MS m/z [M+H]+453.7; Method 2minLowpHv03

¹H NMR (400 MHz, CDCl₃) δ 8.21 (1H, br s), 6.19 (1H, mult), 4.00 (1H, tt), 3.25 (3H, s), 2.46-2.40 (2H, br mults), 2.23 (3H, s), 2.14 (3H, s), 2.10-2.05 (2H, mults), 1.99-1.88 (2H, mults), 1.84-1.74 (4H, br mults), 1.66-1.53 (7H, br mults), 1.41-1.35 (4H, br mults), 1.34-1.23 (2H, br mults), 1.21-1.10 (1H, br mult).

Example 2.1

[N-(2-Cyclohexyl-1,5-dimethyl-3-oxo-2,3-dihydro-1H-pyrazol-4-yl)-4-methyl-5-(1-oxaspiro[4.5]dec-7-en-8-yl)isoxazole-3-carboxamide]

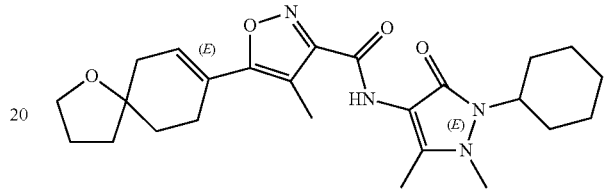

The title compound was prepared by a method similar to that of Example 2 by replacing spiro[4.5]decan-8-one (step 3) with [1-oxaspiro[4.5]decan-8-one] (Fluorochem);

LC-MS: Rt=1.10 mins; MS m/z [M+H]+455.5; Method 2minLowpHv01

Example 2.2

N-(2-Cyclohexyl-1,5-dimethyl-3-oxo-2,3-dihydro-1H-pyrazol-4-yl)-5-(4,4-dimethylcyclohex-1-en-1-yl)-4-methylisoxazole-3-carboxamide

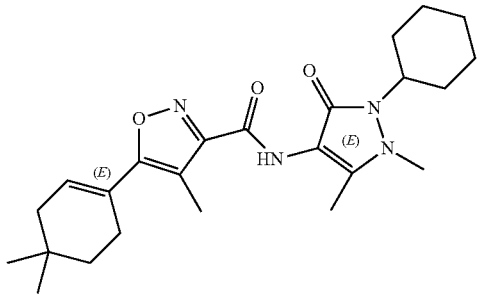 [SMILES: Cc1c(C(=O)Nc2c(C)n(C)n(C3CCCCC3)c2=O)noc1C1=CCC(C)(C)CC1]

The title compound was prepared by a method similar to that of Example 2 by replacing 4,4,5,5-tetramethyl-2-(spiro[4.5]dec-7-en-8-yl)-1,3,2-dioxaborolane (Step 5) with 4,4-dimethylcyclohexen-1-yl boronic acid, pinacol ester (Combi Blocks);

LC-MS: Rt=5.52 mins; MS m/z 427.6 [M+H]+; Method 10minLowpHv01

Example 3

N-(2-Cyclohexyl-1,5-dimethyl-3-oxo-2,3-dihydro-1H-pyrazol-4-yl)-5-(4,4-dimethylcyclopent-1-en-1-yl)-4-methylisoxazole-3-carboxamide

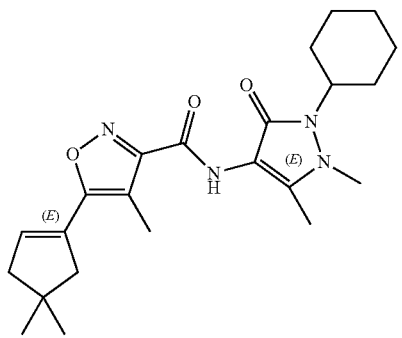 [SMILES: Cc1c(C(=O)Nc2c(C)n(C)n(C3CCCCC3)c2=O)noc1C1=CCC(C)(C)C1]

Step 1: 4,4-Dimethylcyclopent-1-en-1-yl trifluoromethanesulfonate

To a stirred solution of 4,4-dimethylcyclopent-2-enone (Atlantic) (0.500 g, 4.54 mmol) in dry THF (25 mL) under nitrogen at −78° C., 1M L-Selectride in THF (4.539 mL, 4.54 mmol) was added. The reaction mixture was stirred at −78° C. for 1 hour and treated with a solution of 1,1,1-trifluoro-N-(pyridin-2-yl)-N-((trifluoromethyl)sulfonyl)methanesulfonamide (Alfa Aesar) (1.626 g, 4.54 mmol) in dry THF (5 mL). The mixture was stirred and allowed to warm to room temperature overnight. The resulting mixture was partitioned between hexane (60 mL) and water (50 mL), the phases separated and the aqueous phase was extracted with hexane (50 mL). The combined organic extracts were washed with 10% aqueous NaOH (40 mL), brine (40 mL), dried over MgSO$_4$, filtered and concentrated under reduced pressure to give a pale yellow oil. The crude material was adsorbed onto silica and purification by chromatography eluting with 100% iso-hexane afforded the title compound;

$^1$H NMR (400 MHz, CDCl$_3$) δ 5.54 (1H, mult), 2.42-2.39 (2H, mult), 2.23-2.20 (2H, mult), 1.17 (3H, s), 1.17 (3H, s).

Step 2: 2-(4,4-Dimethylcyclopent-1-en-1-yl)-4,4,5,5-tetramethyl-1,3,2-dioxaborolane To a stirred solution of 4,4-dimethylcyclopent-1-en-1-yl trifluoromethanesulfonate (367 mg, 1.503 mmol) in dry 1,4-dioxane (10 mL) was added bis(pinacolato)diboron (Alfa Aesar) (382 mg, 1.503 mmol) followed by potassium acetate (Acros) (295 mg, 3.01 mmol) and PdCl$_2$(dppf).CH$_2$Cl$_2$ adduct (Alfa Aesar) (36.8 mg, 0.045 mmol). The reaction mixture was heated at 80° C. and stirred for 16 hours. The resulting mixture was cooled to room temperature and filtered through Celite®, washing with TBME (100 mL). The organic filtrate was washed with water (50 mL), brine (30 mL), dried over MgSO$_4$, filtered and concentrated under reduced pressure to give a brown oil. The crude material was adsorbed onto silica and purification by chromatography eluting with 100% iso-hexane afforded the title compound;

$^1$H NMR (400 MHz, CDCl$_3$) δ 6.34-6.31 (1H, mult), 2.21-2.18 (2H, mult), 2.17-2.14 (2H, mult), 1.20 (12H, s) 0.99 (6H, s).

Step 3: Ethyl 5-(4,4-dimethylcyclopent-1-en-1-yl)-4-methylisoxazole-3-carboxylate To a 2-5 mL microwave vial containing a solution of 2-(4,4-dimethylcyclopent-1-en-1-yl)-4,4,5,5-tetramethyl-1,3,2-dioxaborolane (214 mg, 0.966 mmol) in acetonitrile (2 mL), ethyl 5-bromo-4-methylisoxazole-3-carboxylate (Intermediate A) (226 mg, 0.966 mmol) was added followed by K$_2$CO$_3$ (400 mg, 2.90 mmol), PdCl$_2$(dppf).CH$_2$Cl$_2$ adduct (Alfa Aesar) (79 mg, 0.097 mmol) and water (1 mL). The vial was flushed with nitrogen, sealed and heated in the microwave (Biotage Smith Initiator) at 90° C. for 1 hour. The resulting mixture was filtered through Celite®, washing with EtOAc (50 mL). The filtrate was washed with water (50 mL), brine (50 mL), dried over MgSO$_4$, filtered and concentrated under reduced pressure to give a brown oil. The crude material was adsorbed onto silica and purification by chromatography eluting with 100% iso-hexane afforded the title compound;

LC-MS: Rt=1.64 mins; MS m/z [M+H]+250.9/251.5; Method 2minLowpHv03

Step 4: 5-(4,4-Dimethylcyclopent-1-en-1-yl)-4-methylisoxazole-3-carboxylic acid To a stirred solution of ethyl 5-(4,4-dimethylcyclopent-1-en-1-yl)-4-methylisoxazole-3-carboxylate (243 mg, 0.975 mmol) in ethanol (5 mL), 2M NaOH (aq) (0.975 mL, 1.949 mmol) was added and the solution was stirred at room temperature. Upon completion the reaction mixture was diluted with water (30 mL) and acidified to pH 5-6 by the addition of 2M HCl (aq). The aqueous phase was extracted with EtOAc (2×20 mL) and the combined organic extracts were washed with brine (20 mL), dried over MgSO$_4$ and filtered. The solvent was removed under reduced pressure to afford the title compound;

LC-MS: Rt=1.46 mins; MS m/z [M+H]+222.5; Method 2minLowpHv03.

Step 5: N-(2-Cyclohexyl-1,5-dimethyl-3-oxo-2,3-dihydro-1H-pyrazol-4-yl)-5-(4,4-dimethylcyclopent-1-en-1-yl)-4-methylisoxazole-3-carboxamide To a stirred solution of 5-(4,4-dimethylcyclopent-1-en-1-yl)-4-methylisoxazole-3-carboxylic acid (105 mg, 0.475 mmol) in dry NMP (3 mL), HATU (198 mg, 0.522 mmol) was added followed by 4-amino-2-cyclohexyl-1,5-dimethyl-1H-pyrazol-3(2H)-one (Intermediate D) (109 mg, 0.522 mmol) and triethylamine (0.146 mL, 1.044 mmol). The mixture was stirred at room temperature overnight. The resulting mixture was partitioned between EtOAc (20 mL) and 1M NaOH (aq) (20 mL) and the organic phase was washed with water (20 mL), brine (20 mL), dried over MgSO$_4$, filtered and concentrated under reduced pressure. The crude material was adsorbed onto silica and purification by chromatography eluting with 0-60% EtOAc in iso-hexane afforded crude material. The crude material was dissolved in DMSO and purified using mass-directed automated reverse phase chromatography over a 9.5 minute gradient of 40-80% MeCN in water (0.1% formic acid). The product fraction was added to EtOAc (50 mL) and washed with a saturated aqueous NaHCO$_3$ solution (50 mL). The organic extracts were dried over MgSO$_4$, filtered and concentrated under reduced pressure to afford the title compound;

LC-MS: Rt=1.40 mins; MS m/z [M+H]+413.1/414.6; Method 2minLowpHv03

$^1$H NMR (400 MHz, CDCl$_3$) δ 8.09 (1H, br s), 6.27 (1H, br t), 4.06 (1H, tt), 3.27 (3H, s), 2.66 (2H, mult), 2.40 (2H, mult), 2.34 (3H, s), 2.22 (3H, s), 2.06-1.95 (2H, br mults), 1.92-1.83 (4H, br mults), 1.75-1.68 (1H, br mult), 1.44-1.31 (2H, br mults), 1.30-1.23 (1H, br mult), 1.19 (6H, s).

Example 4

[N-(2-Cyclohexyl-1,5-dimethyl-3-oxo-2,3-dihydro-1H-pyrazol-4-yl)-4-methyl-5-(2-oxaspiro[4.5]dec-7-en-8-yl)isoxazole-3-carboxamide]

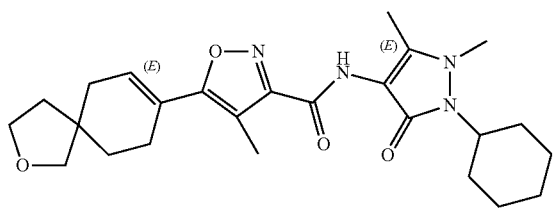

Step 1: Ethyl 1,4-dioxaspiro[4.5]decane-8-carboxylate

A mixture of ethyl 4-oxocyclohexanecarboxylate (11.7 g, 68.7 mmol), ethylene glycol (5.75 mL, 103 mmol) and p-TsOH (0.620 g, 3.26 mmol) in toluene (60 mL) was stirred at reflux using a Dean-Stark trap to collect water over 4 hrs. The resulting mixture was cooled to room temperature, quenched with a saturated aqueous NaHCO$_3$ solution (30 mL) and diluted with EtOAc (100 mL). The organic layer was washed with brine (30 mL), dried over anhydrous sodium sulfate and filtered. The solvent was removed under reduced pressure to afford a yellow oil. The crude material was adsorbed onto silica and purification by chromatography eluting with 0-100% EtOAc in iso-hexane afforded the title compound;

$^1$H NMR (400 MHz, CDCl$_3$) δ 4.14 (2H, q), 3.96 (4H, s), 2.38-2.31 (1H, br mult), 1.99-1.91 (2H, br mults), 1.87-1.76 (4H, br mults), 1.61-1.53 (2H, br mults), 1.26 (3H, t).

Step 2: Ethyl 8-(2-(benzyloxy)ethyl)-1,4-dioxaspiro[4.5]decane-8-carboxylate (8-Allyl-1,4-dioxaspiro[4.5]decan-8-yl)methanol (6 g, 28.0 mmol) in dry THF (100 mL) was added to a pre-cooled solution of KHMDS (1M in THF) (36.4 mL, 36.4 mmol) in THF (100 mL) at −78° C. under nitrogen. The resulting mixture was stirred at this temperature for 2 hrs and a solution of ((2-bromoethoxy)methyl)benzene (5.31 mL, 33.6 mmol) in THF (100 mL) was added.

The reaction mixture was allowed to warm to room temperature and stirred at room temperature overnight. The resulting mixture was quenched with saturated aqueous ammonium chloride solution and EtOAc was added. The organic extracts were dried over MgSO$_4$, filtered and the solvent removed under reduced pressure. The crude material was adsorbed onto silica and purification by chromatography eluting with 0-40% EtOAc in iso-hexane afforded crude material. The crude material was again adsorbed onto silica and purification by chromatography eluting with 0-20% EtOAc in iso-hexane afforded the title compound;

$^1$H NMR (400 MHz, DMSO-d6) δ 7.36-7.31 (2H, mults), 7.30-7.26 (3H, mults), 4.39 (2H, s), 4.01 (2H, q), 3.84 (4H, s), 3.40 (2H, t), 2.05-1.98 (2H, br mults), 1.78 (2H, t), 1.61-1.54 (2H, br mults), 1.49-1.41 (4H, br mults), 1.12 (3H, t).

Step 3: [1,4,10-Trioxadispiro[4.2.4.2]tetradecan-9-one]

[Ethyl 8-(2-(benzyloxy)ethyl)-1,4-dioxaspiro[4.5]decane-8-carboxylate] (1.6 g, 4.59 mmol) in ethanol (5 mL) was degassed thoroughly refilling with nitrogen. Pd—C (0.147 g, 1.378 mmol) was added and the mixture was stirred under an atmosphere of hydrogen. Upon completion the reaction mixture was filtered through a Celite® cartridge, eluting with EtOH. The filtrate was collected and the solvent removed under reduced pressure to afford the title compound;

$^1$H NMR (400 MHz, CDCl$_3$) δ 4.29 (2H, t), 3.97 (4H, mult), 2.19 (2H, t), 2.08-1.99 (2H, br mults), 1.97-1.89 (2H, br mults), 1.71-1.56 (4H, br mults).

Step 5: [1,4,10-Trioxadispiro[4.2.4.2]tetradecan-9-ol]

1,4,10-Trioxadispiro[4.2.4.2]tetradecan-9-one (880 mg, 4.15 mmol) in toluene (30 mL), under nitrogen, was cooled to −78° C. and treated with 1M DIBAL-H (1M in toluene) (4.56 mL, 4.56 mmol). The reaction mixture was stirred at −78° C. for 2 hours. The resulting mixture was treated with 10% aqueous acetic acid solution (18 mL)/ice 60 g) and stirred for 5 mins with chloroform (150 mL). The aqueous was separated and extracted with chloroform (×3) and the combined organic extracts were dried over MgSO$_4$ and filtered. The solvent was removed under reduced pressure to afford the title compound;

$^1$H NMR (400 MHz, CDCl$_3$) δ 5.13 (1H, s), 4.11 (1H, mult), 3.97 (4H, mult), 3.93 (1H, mult), 2.12 (1H, s), 1.95-1.77 (3H, br mults), 1.76-1.60 (6H, br mults), 1.58-1.49 (1H, br mults).

Step 6: [1,4,10-Trioxadispiro[4.2.4.2]tetradecane]

To a stirred solution of triethylsilane (1.965 mL, 12.30 mmol) in DCM (40 mL), under nitrogen, at −78° C. was successively added trifluoroacetic acid (0.948 mL, 12.30 mmol) and [1,4,10-trioxadispiro[4.2.4.2]tetradecan-9-ol] (0.878 g, 4.1 mmol) in DCM (40 mL) at −78° C. The resulting mixture was slowly warmed to 0° C. and stirred for 2 hours. Saturated aqueous NaHCO$_3$ solution was added and the mixture was extracted with EtOAc. The combined organic extracts were dried over MgSO$_4$, filtered and the solvent removed under reduced pressure to afford the title compound.

Step 7: [2-Oxaspiro[4.5]decan-8-one]

A stirred solution of 1,4,10-rioxadispiro[4.2.4.2]tetradecane (813 mg, 4.1 mmol) in acetone (28 mL) at room temperature was treated with a 10% aqueous HCl solution (12.46 mL, 41.0 mmol). The reaction mixture was stirred at room temperature for 1 hour. The resulting mixture was diluted with brine (40 mL) and extracted with EtOAc (3×30 mL). The combined organic extracts were washed with saturated aqueous NaHCO$_3$ (2×30 mL) and brine (1×30 mL), dried over MgSO$_4$ and filtered. The solvent was removed under reduced pressure. The crude material was adsorbed onto silica and purification by chromatography eluting with 0-100% EtOAc in iso-hexane afforded the title compound;

¹H NMR (400 MHz, CDCl₃) δ 3.96 (2H, t), 3.70 (2H, s), 2.45-2.36 (4H, br mults), 1.95-1.89 (6H, mults).

Step 8: [2-Oxaspiro[4.5]dec-7-en-8-yl trifluoromethanesulfonate]

A solution of diisopropylamine (0.407 mL, 2.85 mmol) in THF (25 mL), under nitrogen, was cooled to −78° C. and treated with n-BuLi (1.0 M in hexanes) (1.702 mL, 2.72 mmol). The reaction mixture was warmed to 0° C. over 30 mins and cooled to −78° C. before adding 2-oxaspiro[4.5]decan-8-one (400 mg, 2.59 mmol) in THF (25 mL). After 1.5 hours at −78° C. the reaction mixture was treated with 1,1,1-trifluoro-N-(pyridin-2-yl)-N-((trifluoromethyl)sulfonyl)methanesulfonamide (1208 mg, 3.37 mmol) in THF (10 mL) and allowed to warm to room temperature overnight. Saturated aqueous NaHCO₃ solution was added followed by dilution with EtOAc. The organic layer was dried over MgSO₄, filtered and the solvent removed under reduced pressure. The crude material was adsorbed onto silica and purification by chromatography eluting with 0-25% EtOAc in iso-hexane afforded the title compound;
¹H NMR (400 MHz, CDCl₃) δ 5.77 (1H, t), 3.92 (2H, t), 3.56 (2H, mult), 2.46-2.29 (2H, br mult), 2.25-2.22 (2H, br mult), 1.83-1.76 (4H, br mults).

Step 9: [4,4,5,5-Tetramethyl-2-(2-oxaspiro[4.5]dec-7-en-8-yl)-1,3,2-dioxaborolane]

[2-Oxaspiro[4.5]dec-7-en-8-yl trifluoromethanesulfonate] (270 mg, 0.943 mmol) and 4,4,4',4',5,5,5',5'-octamethyl-2,2'-bi(1,3,2-dioxaborolane) (251 mg, 0.990 mmol) in dioxane (5 mL) were treated with potassium acetate (185 mg, 1.886 mmol) and the mixture was degassed thoroughly refilling with nitrogen. PdCl₂(dppf).CH₂Cl₂ adduct (23.11 mg, 0.028 mmol) was added and the mixture was heated to 80° C. for 16 hours. The crude reaction mixture was adsorbed onto silica and purification by chromatography eluting with 0-15% EtOAc in iso-hexane afforded the title compound;
¹H NMR (400 MHz, CDCl₃) δ 6.54 (1H, mult), 3.88 (2H, t), 3.52 (2H, mult), 2.24-2.18 (2H, br mults), 2.15-2.12 (2H, br mults), 1.76-1.68 (2H, br mults), 1.62-1.57 (2H, br mults), 1.28 (12H, s).

Step 10: [Ethyl 4-methyl-5-(2-oxaspiro[4.5]dec-7-en-8-yl)isoxazole-3-carboxylate]

[4,4,5,5-tetramethyl-2-(2-oxaspiro[4.5]dec-7-en-8-yl)-1,3,2-dioxaborolane] (0.172 g, 0.651 mmol), ethyl 5-bromo-4-methylisoxazole-3-carboxylate (Intermediate A) (0.183 g, 0.781 mmol) and Cs₂CO₃ (0.849 g, 2.60 mmol) were combined in DME (3 mL) and water (1.250 mL). PdCl₂(dppf).CH₂Cl₂ adduct (0.016 g, 0.020 mmol) was added and the mixture was degassed thoroughly refilling with nitrogen. The mixture was stirred in the microwave at 90° C. for 1 hour. The biphasic reaction mixture was separated and the organic phase was adsorbed onto silica. Purification by chromatography eluting with a gradient of EtOAc in iso-hexane afforded the title compound;
¹H NMR (400 MHz, CDCl₃) δ 6.27 (1H, mult), 4.42 (2H, q), 3.91 (2H, t), 3.56 (2H, mult), 2.56-2.51 (2H, br mults), 2.31-2.27 (2H, br mults), 2.28 (3H, s), 1.83-1.72 (4H, br mults), 1.41 (3H, t).

Step 11: [4-Methyl-5-(2-oxaspiro[4.5]dec-7-en-8-yl)isoxazole-3-carboxylic acid]

[Ethyl 4-methyl-5-(2-oxaspiro[4.5]dec-7-en-8-yl)isoxazole-3-carboxylate] (170 mg, 0.584 mmol) in MeOH (3.60 mL) and THF (6 mL) was treated at room temperature with 2M NaOH (aq) (0.584 mL, 1.167 mmol). The resulting mixture was stirred at room temperature and treated with 2M HCl (aq) (0.2 mL) and EtOAc. The combined organic layers were dried over MgSO₄ and filtered and the solvent was removed under reduced pressure to afford the title compound;
LC-MS: Rt=0.61 mins; MS m/z [M+H]+264.4; Method 2minHighpHv03

Step 12: [N-(2-Cyclohexyl-1,5-dimethyl-3-oxo-2,3-dihydro-1H-pyrazol-4-yl)-4-methyl-5-(2-oxaspiro[4.5]dec-7-en-8-yl)isoxazole-3-carboxamide]

A solution of [4-methyl-5-(2-oxaspiro[4.5]dec-7-en-8-yl)isoxazole-3-carboxylic acid] (40 mg, 0.152 mmol) in DMF (3 mL) was treated with 4-amino-2-cyclohexyl-1,5-dimethyl-1H-pyrazol-3(2H)-one (Intermediate D) (38.2 mg, 0.182 mmol), DIPEA (0.106 mL, 0.608 mmol) and HATU (75 mg, 0.198 mmol). The resulting mixture was stirred at room temperature for 16 hours. Water was added to the mixture and the aqueous was extracted with EtOAc (×2). The combined organic extracts were washed with 0.5M lithium chloride (aq), dried over MgSO₄, filtered and the solvent removed under reduced pressure. The crude material was adsorbed onto silica and purification by chromatography eluting with 0-5% MeOH in EtOAc afforded the title compound;
LC-MS: Rt=1.19 mins; MS m/z [M+H]+455.5; Method 2minLowpHv03
¹H NMR (400 MHz, CDCl₃) δ 8.31 (1H, s), 6.23 (1H, mult), 4.01 (1H, tt), 3.88 (2H, t), 3.53 (2H, s), 3.26 (3H, s), 2.51-2.44 (2H, br mults), 2.28-2.25 (2H, mults), 2.23 (3H, s), 2.14 (3H, s), 1.98-1.87 (2H, br mults), 1.81-1.70 (8H, mults), 1.65-1.58 (1H, br mult), 1.38-1.33 (1H, br mult), 1.31-1.25 (1H, br mult), 1.18-1.05 (1H br mult).

Example 5

[N-(2-Cyclohexyl-1,5-dimethyl-3-oxo-2,3-dihydro-1H-pyrazol-4-yl)-5-(4-isopropoxycyclohex-1-en-1-yl)-4-methylisoxazole-3-carboxamide]

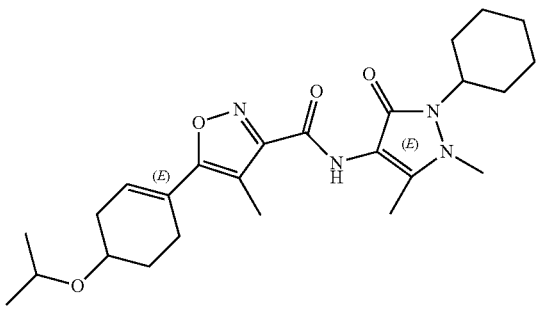 [SMILES: Cc1c(C(=O)Nc2c(C)n(C)n(C3CCCCC3)c2=O)noc1C1=CCC(OC(C)C)CC1]

Step 1: 1,4-Dioxaspiro[4.5]decan-8-ol

To a stirred solution of 1,4-cyclohexadione monoethylene acetal (Aldrich) (2 g, 12.81 mmol) in dry MeOH (30 mL) at 0° C., NaBH₄ (0.727 g, 19.21 mmol) was added in portionwise, keeping the temperature below 5° C. The reaction mixture was stirred at 0° C. for 15 minutes and at room temperature for 2 hours. The resulting mixture was concentrated under reduced pressure to afford the title compound;

$^1$H NMR (400 MHz, CDCl$_3$) δ 3.96 (4H, s), 3.86-3.78 (1H, br mult), 1.94-1.79 (4H, br mults), 1.73-1.76 (4H, br mults), 1.43 (1H, br s).

Step 2: 8-Isopropoxy-1,4-dioxaspiro[4.5]decane

To a stirred solution of 1,4-dioxaspiro[4.5]decan-8-ol (0.5 g, 3.16 mmol) in 2-iodopropane (5.37 g, 31.6 mmol), silver (I) oxide (1.392 g, 6.01 mmol) was added and the reaction mixture was stirred at room temperature. Upon completion the resulting suspension was diluted with EtOAc and the suspension filtered under reduced pressure. The filtrate was concentrated under reduced pressure to give a pale yellow oil. The crude material was adsorbed onto silica and purification by chromatography eluting with 0-30% EtOAc in iso-hexane to afforded the title compound;
$^1$H NMR (400 MHz, DMSO-d6) δ 3.84 (4H, s), 3.63 (1H, mult), 3.44 (1H, mult), 1.72-1.62 (4H, br mults), 1.53-1.42 (4H, br mults), 1.06 (3H, s), 1.05 (3H, s).

Step 3: 4-Isopropoxycyclohexanone

To a stirred solution of 8-isopropoxy-1,4-dioxaspiro[4.5]decane (0.464 g, 2.317 mmol) in THF (2 mL) and water (2 mL), p-TsOH (0.080 g, 0.463 mmol) was added. The mixture was heated to 100° C. overnight. The resulting mixture was allowed to cool to room temperature and partitioned between EtOAc (30 mL) and water (30 mL). The organic phase was washed with brine (30 mL), dried over MgSO$_4$ and filtered. The solvent was removed under reduced pressure to afford the title compound;
$^1$H NMR (400 MHz, DMSO-d6) δ 3.78 (1H, mult), 3.73 (1H, mult), 2.40-2.31 (2H, br mults), 2.27-2.18 (2H, br mults), 1.96-1.87 (2H, br mults), 1.85-1.75 (2H, br mults), 1.12 (3H, s), 1.11 (3H, s).

Step 4: [4-Isopropoxycyclohex-1-en-1-yl trifluoromethanesulfonate]

1.6M nBuLi in hexane (Aldrich) (1.285 mL, 2.057 mmol) was added to a solution of diisopropylamine (Acros) (0.307 mL, 2.155 mmol) in dry THF (30 mL) under nitrogen at –78° C. The solution was allowed to warm to 0° C. for 30 minutes before re-cooling to –78° C. A solution of 4-isopropoxycyclohexanone (306 mg, 1.959 mmol) in dry THF (5 mL) was added over 5 minutes and the mixture was stirred at –78° C. for 1 hour before adding a solution of 2-[N,N-bis(trifluoromethylsulfonyl)amino]pyridine (Alfa Aesar) (772 mg, 2.155 mmol) in dry THF (5 mL). The mixture was stirred and allowed to warm to room temperature overnight. The resulting mixture was quenched with a saturated aqueous NaHCO$_3$ solution (30 mL) and the aqueous was extracted with TBME (2×20 mL). The combined organic extracts were washed with 10% aqueous NaOH (30 mL), brine (30 mL), dried over MgSO$_4$, filtered and concentrated under reduced pressure. The crude material was adsorbed onto silica and purification by chromatography eluting with 0-10% EtOAc in iso-hexane afforded the title compound;
$^1$H NMR (400 MHz, DMSO-d6) δ 5.76 (1H, mult), 3.72-3.63 (2H, mults), 2.44-2.30 (3H, br mults), 2.14-2.06 (1H, mult), 1.86-1.73 (2H, br mults), 1.09-1.04 (6H, mults).

Step 5: [2-(4-Isopropoxycyclohex-1-en-1-yl)-4,4,5,5-tetramethyl-1,3,2-dioxaborolane]

To a stirred solution of [4-isopropoxycyclohex-1-en-1-yl trifluoromethanesulfonate] (459 mg, 1.592 mmol) in dry dioxane (15 mL), bis(pinacolato)diboron (Alfa Aesar) (404 mg, 1.592 mmol) was added followed by potassium acetate (Acros) (313 mg, 3.18 mmol) and PdCl$_2$(dppf).CH$_2$Cl$_2$ adduct (Alfa Aesar) (39.0 mg, 0.048 mmol). The flask was flushed with nitrogen and heated to 80° C. overnight. The resulting mixture was cooled to room temperature and filtered through Celite®, washing with TBME. The organic filtrate was concentrated under reduced pressure and the residue partitioned between EtOAc (50 mL) and water (50 mL). The organic phase was washed with brine (30 mL), dried over MgSO$_4$, filtered and concentrated under reduced pressure. The crude material was adsorbed onto silica and purification by chromatography eluting with 0-30% EtOAc in iso-hexane afforded the title compound.

Step 6: [Ethyl 5-(4-isopropoxycyclohex-1-en-1-yl)-4-methylisoxazole-3-carboxylate]

To a 2-5 mL microwave vial containing a solution of [2-(4-isopropoxycyclohex-1-en-1-yl)-4,4,5,5-tetramethyl-1,3,2-dioxaborolane] (375 mg, 1.410 mmol) in acetonitrile (2 mL), ethyl 5-bromo-4-methylisoxazole-3-carboxylate (Intermediate A) (330 mg, 1.410 mmol) was added followed by K$_2$CO$_3$ (585 mg, 4.23 mmol), PdCl$_2$(dppf).CH$_2$Cl$_2$ adduct (11.51 mg, 0.014 mmol) and water (2 mL). The vial was flushed with nitrogen and treated in the microwave (Biotage Smith Initiator) at 80° C. for 90 minutes. The reaction mixture was partitioned between water (30 mL) and EtOAc (30 mL). The organic phase was washed with brine (30 mL), dried over MgSO$_4$, filtered through a Celite® pad and the filtrate was concentrated under reduced pressure. The crude material was adsorbed onto silica and purification by chromatography eluting with 0-60% EtOAc in iso-hexane afforded the title compound;
LC-MS: Rt=1.33 minutes; MS m/z [M+H]+294.4; Method 2minLowpHv01

Step 7: [5-(4-Isopropoxycyclohex-1-en-1-yl)-4-methylisoxazole-3-carboxylic acid]

To a stirred solution of [ethyl 5-(4-isopropoxycyclohex-1-en-1-yl)-4-methylisoxazole-3-carboxylate] (393 mg, 1.340 mmol) in THF (3 mL) and Ethanol (3 mL), 2M NaOH (aq) (4.179 ml, 8.36 mmol) was added. The reaction mixture was stirred at room temperature. Upon completion the resulting mixture was poured into water (20 mL) and the pH adjusted to pH 6 with the addition of 1M HCl (aq). The aqueous was extracted with EtOAc (30 mL) and the organic extracts were washed with brine (20 mL), dried over MgSO$_4$ and filtered. The solvent was removed under reduced pressure to afford the title compound;
LC-MS: Rt=1.13 minutes; MS m/z [M+H]+266.1; Method 2minLowpHv01

Step 8: [N-(2-Cyclohexyl-1,5-dimethyl-3-oxo-2,3-dihydro-1H-pyrazol-4-yl)-5-(4-isopropoxycyclohex-1-en-1-yl)-4-methylisoxazole-3-carboxamide]

To a stirred solution of 5-(4-isopropoxycyclohex-1-en-1-yl)-4-methylisoxazole-3-carboxylic acid (174 mg, 0.656 mmol) in dry NMP (3 mL), HATU (274 mg, 0.721 mmol) was added followed by 4-amino-2-cyclohexyl-1,5-dimethyl-1H-pyrazol-3(2H)-one (Intermediate D) (151 mg, 0.721 mmol) and triethylamine (0.201 mL, 1.443 mmol). The mixture was stirred at room temperature overnight. The resulting mixture was partitioned between EtOAc (20 mL) and 1M NaOH (aq) (20 mL) and the organic phase was washed with water (30 mL), brine (30 mL), dried over MgSO₄, filtered and concentrated under reduced pressure. The crude material was dissolved in DMSO and purified using a UV-directed reverse phase chromatography with a gradient of 40-80% MeCN in water (0.1% formic acid) over 9.5 minutes. The product fraction was added to EtOAc (50 mL) and washed with a saturated aqueous NaHCO₃ solution (50 mL). The organic phase was dried over MgSO₄, filtered and concentrated under reduced pressure to afford the title compound;

LC-MS: Rt=1.19 minutes; MS m/z [M+H]+457.3; Method 2minLowpHv01

¹H NMR (400 MHz, DMSO-d6) δ 9.47 (1H, s), 6.27 (1H, mult), 3.91 (1H, mult), 3.75 (1H, mult), 3.75-3.67 (1H, br mult), 3.22 (3H, s), 2.58-2.40 (4H, br mults), 2.19 (3H, s), 2.19-2.09 (1H, br mults), 2.06-2.01 (4H, mults), 1.99 (1H, mult), 1.96-1.86 (1H, br mult), 1.82-1.74 (2H, br mults), 1.72-1.58 (4H, br mults), 1.38-1.24 (2H, br mults), 1.11-1.07 (6H, mults).

Example 6

N-(2-Cyclohexyl-1,5-dimethyl-3-oxo-2,3-dihydro-1H-pyrazol-4-yl)-5-(4,4-dimethylcyclohexyl)-4-methylisoxazole-3-carboxamide

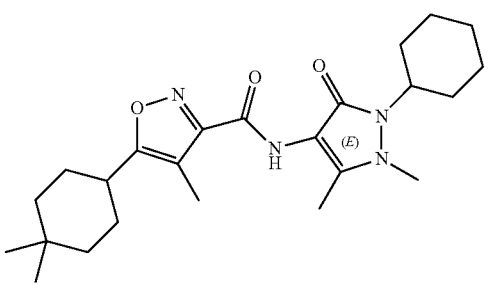 [SMILES: Cc1c(C(=O)Nc2c(C)n(C)n(C3CCCCC3)c2=O)noc1C1CCC(C)(C)CC1]

A solution of N-(2-cyclohexyl-1,5-dimethyl-3-oxo-2,3-dihydro-1H-pyrazol-4-yl)-5-(4,4-dimethylcyclohex-1-en-1-yl)-4-methylisoxazole-3-carboxamide (Example 2.2) (40 mg, 0.094 mmol) in ethanol (20 mL) was flushed with nitrogen and treated with 10% Pd—C, 50% wet (Alfa Aesar, 38303) (14.97 mg, 0.141 mmol). The reaction mixture was stirred at room temperature under an atmosphere of hydrogen for 3 hours. The resulting mixture was filtered through Celite®, washing with ethanol followed by DCM. The filtrate was concentrated under reduced pressure and the residue was passed through a 500 mg silica-TMT cartridge, eluting with ethanol:ether (1:1). The filtrate was collected and the solvent removed under reduced pressure to afford the title compound;

LC-MS; Rt=1.33 minutes; MS m/z [M+H]+429.5; Method 2minLowpHv01

¹H NMR (400 MHz, DMSO-d6) δ 9.40 (1H, s), 3.92 (1H, tt), 3.21 (3H, s), 2.84 (1H, mult), 2.07 (3H, s), 2.02 (3H, s), 2.03-1.95 (2H, mults), 1.82-1.58 (9H, mults), 1.50-1.43 (2H, mults), 1.37-1.22 (5H, mults), 0.97 (3H, s), 0.95 (3H, s).

Example 6.1

[N-(2-Cyclohexyl-1,5-dimethyl-3-oxo-2,3-dihydro-1H-pyrazol-4-yl)-5-(3,3-dimethylcyclopentyl)-4-methylisoxazole-3-carboxamide]

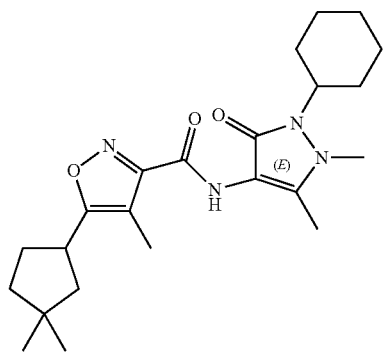 [SMILES: Cc1c(C(=O)Nc2c(C)n(C)n(C3CCCCC3)c2=O)noc1C1CCC(C)(C)C1]

The title compound was prepared by a method similar to that of Example 6 by replacing N-(2-cyclohexyl-1,5-dimethyl-3-oxo-2,3-dihydro-1H-pyrazol-4-yl)-5-(4,4-dimethylcyclohex-1-en-1-yl)-4-methylisoxazole-3-carboxamide (Example 2.2) (Step 1) with N-(2-cyclohexyl-1,5-dimethyl-3-oxo-2,3-dihydro-1H-pyrazol-4-yl)-5-(4,4-dimethylcyclopent-1-en-1-yl)-4-methylisoxazole-3-carboxamide (Example 3).

LC-MS: Rt=1.46 mins; MS m/z [M+H]+415.1/416.4; Method 2minLowpHv03

Example 7

N-(2-Cyclohexyl-1,5-dimethyl-3-oxo-2,3-dihydro-1H-pyrazol-4-yl)-5-(3,3-dimethyl butyl)-4-methylisoxazole-3-carboxamide

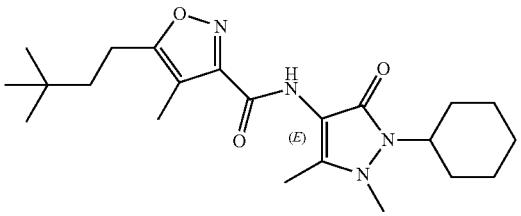 [SMILES: Cc1c(C(=O)Nc2c(C)n(C)n(C3CCCCC3)c2=O)noc1CCC(C)(C)C]

Step 1: Ethyl 5-(3,3-dimethylbut-1-yn-1-yl)-4-methylisoxazole-3-carboxylate

Ethyl 5-bromo-4-methylisoxazole-3-carboxylate (Intermediate A) (100 mg, 0.427 mmol) and 3,3-dimethylbut-1-yne (0.058 mL, 0.470 mmol) in acetonitrile (3 mL) were degassed thoroughly refilling with nitrogen. Dicyclohexylamine (0.085 mL, 0.427 mmol), CuI (2.85 mg, 0.015 mmol) and PdCl₂(PPh₃)₂ (7.50 mg, 10.68 mmol) were added. The mixture was stirred in the microwave at 100° C. for 45 mins. The resulting mixture was adsorbed onto silica and purification by chromatography eluting with 0-10% EtOAc in iso-hexane afforded the title compound;

LC-MS: Rt=1.53 mins; MS m/z [M+H]+236.4; Method 2minLowpHv03

Step 2: 5-(3,3-Dimethylbut-1-yn-1-yl)-4-methylisoxazole-3-carboxylic acid

Ethyl 5-(3,3-dimethylbut-1-yn-1-yl)-4-methylisoxazole-3-carboxylate (101 mg, 0.429 mmol) in THF (3 mL) and MeOH (1.800 mL) was treated at room temperature with 2M NaOH (aq) (0.429 mL, 0.859 mmol) for 1 hour. 2M HCl (aq) (0.6 mL) and water were added and the aqueous was extracted with EtOAc. The combined organic extracts were dried over MgSO$_4$ and filtered. The solvent was removed under reduced pressure to afford the title compound;

$^1$H NMR (400 MHz, DMSO-d6) δ 14.07 (1H, br s), 2.14 (3H, s), 1.33 (9H, s).

Step 3: N-(2-Cyclohexyl-1,5-dimethyl-3-oxo-2,3-dihydro-1H-pyrazol-4-yl)-5-(3,3-dimethylbut-1-yn-1-yl)-4-methylisoxazole-3-carboxamide 5-(3,3-Dimethylbut-1-yn-1-yl)-4-methylisoxazole-3-carboxylic acid (85 mg, 0.410 mmol) and 4-amino-2-cyclohexyl-1,5-dimethyl-1H-pyrazol-3(2H)-one (Intermediate D) (86 mg, 0.410 mmol) in DMF (2 mL) were treated with DIPEA (0.287 mL, 1.641 mmol) and HATU (172 mg, 0.451 mmol) at room temperature and stirred for 16 hours. The resulting mixture was diluted with water and extracted with EtOAc. The combined organic extracts were washed with a 0.5 M Lithium Chloride (aq) solution, dried over MgSO$_4$, filtered and the solvent removed under reduced pressure. The crude material was adsorbed onto silica and purification by chromatography eluting with 0-100% EtOAc in iso-hexane afforded the title compound;

LC-MS: Rt=1.42 mins; MS m/z [M+H]+399.7; Method 2minLowpHv03

Step 4: N-(2-Cyclohexyl-1,5-dimethyl-3-oxo-2,3-dihydro-1H-pyrazol-4-yl)-5-(3,3-dimethylbutyl)-4-methylisoxazole-3-carboxamide N-(2-Cyclohexyl-1,5-dimethyl-3-oxo-2,3-dihydro-1H-pyrazol-4-yl)-5-(3,3-dimethylbut-1-yn-1-yl)-4-methylisoxazole-3-carboxamide (30 mg, 0.075 mmol) in ethanol (5 mL) was degassed thoroughly refilling with nitrogen and Pd—C (16.02 mg, 7.53 µmol) was added. The mixture was stirred under an atmosphere of hydrogen. Upon completion the reaction mixture was filtered through Celite® and the solvent was removed under reduced pressure. The crude material was adsorbed onto silica and purification by chromatography eluting with 0-100% EtOAc in iso-hexane afforded the title compound;

LC-MS: Rt=1.37 mins; MS m/z [M+H]+403.1/404.4; Method 2minLowpHv03

$^1$H NMR (400 MHz, CDCl$_3$) δ 7.97 (1H, br s), 4.04 (1H, tt), 3.24 (3H, s), 2.72-2.66 (2H, mult), 2.19 (3H, s), 2.16 (3H, s), 2.04-1.92 (2H, br mults), 1.90-1.81 (4H, br mults), 1.70 (1H, br mult), 1.60-1.54 (2H, mult), 1.43-1.29 (2H, br mults), 1.27-1.18 (1H, br mult), 0.96 (9H, s).

Example 8

(Z)—N-(2-Cyclohexyl-1,5-dimethyl-3-oxo-2,3-dihydro-1H-pyrazol-4-yl)-5-(3,3-dimethylbut-1-en-1-yl)-4-methylisoxazole-3-carboxamide

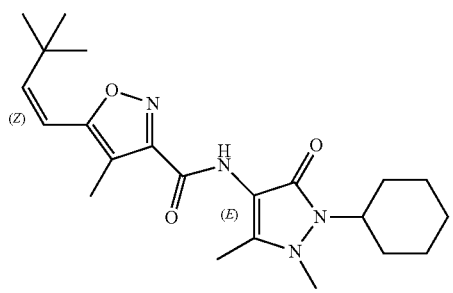 [SMILES: Cc1c(C(=O)Nc2c(C)n(C)n(C3CCCCC3)c2=O)noc1/C=C\C(C)(C)C]

Step 1: (Z)—N-(2-Cyclohexyl-1,5-dimethyl-3-oxo-2,3-dihydro-1H-pyrazol-4-yl)-5-(3,3-dimethylbut-1-en-1-yl)-4-methylisoxazole-3-carboxamide N-(2-Cyclohexyl-1,5-dimethyl-3-oxo-2,3-dihydro-1H-pyrazol-4-yl)-5-(3,3-dimethylbut-1-yn-1-yl)-4-methylisoxazole-3-carboxamide (Example 7, Step 3)) (30 mg, 0.075 mmol) in EtOAc (3 mL) was treated with 2,2'-(ethane-1,2-diylbis(sulfanediyl))diethanol (13.72 mg, 0.075 mmol) and Pd-5% Barium sulphate (16.02 mg, 7.53 µmol). The mixture was degassed, thoroughly refilling with nitrogen and the mixture was stirred under an atmosphere of hydrogen at room temperature overnight. Further Pd-5% Barium sulphate (16.02 mg, 7.53 µmol) was added and the reaction mixture was stirred at room temperature under an atmosphere of hydrogen for 16 hours. The resulting mixture was filtered through Celite® eluting with EtOAc and the solvent was removed under reduced pressure. The crude material was adsorbed onto silica and purification by chromatography eluting with 0-100% EtOAc in iso-hexane afforded the title compound;

LC-MS: Rt=1.35 mins; MS m/z [M+H]+401.2; Method 2minLowpHv03

$^1$H NMR (400 MHz, CDCl$_3$) δ 7.94 (1H, br s), 6.00 (1H, d, J=12.9 Hz), 5.91 (1H, d, J=12.9 Hz), 4.01-3.92 (1H, tt), 3.16 (3H, s), 2.13 (3H, s), 2.09 (3H, s), 1.96-1.84 (2H, br mults), 1.82-1.74 (4H, br mults), 1.62 (1H, br mult), 1.34-1.23 (2H, mult), 1.19-1.10 (1H, br mult), 1.05 (9H, s).

Example 9

(E)-N-(2-Cyclohexyl-1,5-dimethyl-3-oxo-2,3-dihydro-1H-pyrazol-4-yl)-5-(3,3-dimethylbut-1-en-1-yl)-4-methylisoxazole-3-carboxamide

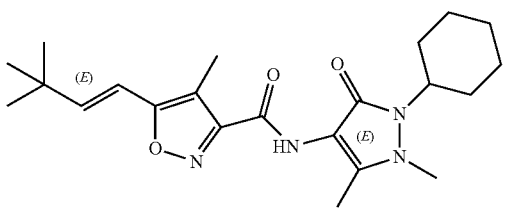 [SMILES: Cc1c(C(=O)Nc2c(C)n(C)n(C3CCCCC3)c2=O)noc1/C=C/C(C)(C)C]

Step 1:
(E)-Tributyl(3,3-dimethylbut-1-en-1-yl)stannane

Tributyltin hydride (1.637 mL, 6.09 mmol) was added dropwise to a solution of 3,3-dimethylbut-1-yne (500 mg, 6.09 mmol) and Pd(Ph$_3$P)$_4$ (70 mg, 0.06 mmol) in THF (4 mL) at 0° C. in the dark. After 30 minutes of stirring the reaction mixture was warmed to room temperature and was stirred for 16 hours. The solvent was removed under reduced pressure. The crude material was adsorbed onto silica and purification by chromatography eluting with 100% iso-hexane afforded the title compound.

Step 2: (E)-Ethyl 5-(3,3-dimethylbut-1-en-1-yl)-4-methylisoxazole-3-carboxylate (E)-Tributyl(3,3-dimethylbut-1-en-1-yl)stannane (1194 mg, 0.8 mmol) and ethyl 5-bromo-4-methylisoxazole-3-carboxylate (Intermediate A) (187 mg, 0.8 mmol) were dissolved in dioxane (6 mL) and the mixture was degassed thoroughly, refilling with nitrogen. Pd(Ph$_3$P)$_4$ (92 mg, 0.080 mmol) was added and the mixture was stirred at 100° C. for 16 hours. The crude reaction mixture was adsorbed onto silica and purification by chromatography eluting with 0-10% EtOAc in iso-hexane afforded the title compound;
$^1$H NMR (400 MHz, CDCl$_3$) δ 6.64 (1H, d, J=17 Hz), 6.19 (1H, d, J=17 Hz), 2.23 (3H, s), 1.45 (3H, t), 1.16 (9H, s).

Step 3: (E)-5-(3,3-Dimethylbut-1-en-1-yl)-4-methylisoxazole-3-carboxylic acid (E)-Ethyl 5-(3,3-imethylbut-1-en-1-yl)-4-methylisoxazole-3-carboxylate (160 mg, 0.674 mmol) in THF (3 mL) and MeOH (1.8 mL) was treated with 2M NaOH (aq) (1.349 mL, 2.70 mmol) and stirred at room temperature for 2 hours. The resulting mixture was treated with 2M HCl (aq) and extracted with ethyl acetate (×3). The combined organic extracts were dried over MgSO$_4$ and filtered. The solvent was removed under reduced pressure to afford the title compound.

Step 4: (E)-N-(2-Cyclohexyl-1,5-dimethyl-3-oxo-2,3-dihydro-1H-pyrazol-4-yl)-5-(3,3-dimethylbut-1-en-1-yl)-4-methylisoxazole-3-carboxamide (E)-5-(3,3-Dimethylbut-1-en-1-yl)-4-methylisoxazole-3-carboxylic acid (102 mg, 0.487 mmol) and 4-amino-2-cyclohexyl-1,5-dimethyl-1H-pyrazol-3(2H)-one (Intermediate D) (112 mg, 0.536 mmol) in DMF (2 mL) were treated with DIPEA (0.341 mL, 1.950 mmol) and HATU (222 mg, 0.585 mmol). The reaction mixture was stirred at room temperature for 2 hours. The resulting mixture was treated with water and extracted with EtOAc. The combined organic extracts were washed with 0.5 M LiCl (aq), dried over MgSO$_4$, filtered and the solvent was removed under reduced pressure. The crude material was adsorbed onto silica and purification by chromatography eluting with 0-100% EtOAc in iso-hexane afforded the title compound;
LC-MS: Rt=1.41 mins; MS m/z [M+H]+401.0/402.5; Method 2minLowpHv03
$^1$H NMR (400 MHz, MeOD) δ 6.64 (1H, d, J=17 Hz), 6.33 (1H, d, J=17 Hz), 4.16 (1H, tt), 3.36 (3H, s), 2.22 (3H, s), 2.20-2.09 (2H, br mults), 2.17 (3H, s), 1.95-1.82 (4H, br mults), 1.76-1.69 (1H, br mult), 1.50-1.38 (2H, br mults), 1.35-1.25 (1H, br mult), 1.18 (9H, s).

Example 10

5-Cyclohexyl-N-(2-cyclohexyl-1,5-dimethyl-3-oxo-2,3-dihydro-1H-pyrazol-4-yl)-4-methylisoxazole-3-carboxamide

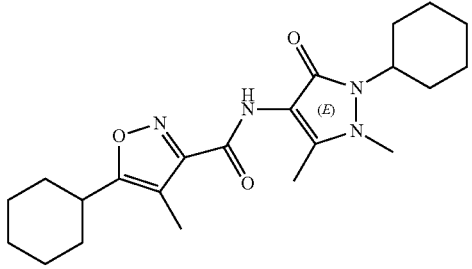 [SMILES: Cc1c(C(=O)Nc2c(C)n(C)n(C3CCCCC3)c2=O)noc1C1CCCCC1]

Step 1: 5-Bromo-4-methylisoxazole-3-carboxylic acid

To a solution of ethyl 5-bromo-4-methylisoxazole-3-carboxylate (Intermediate A) (8.65 g, 37.0 mmol) in MeOH (100 mL) was added 2M NaOH (aq) (18.48 mL, 37.0 mmol). The reaction mixture was stirred at room temperature for 10 minutes and the resulting mixture was acidified using 1M HCl (aq) and concentrated under reduced pressure to remove MeOH. The aqueous was diluted with water and extracted with EtOAc (×3) and the combined organic extracts were dried over MgSO$_4$ and filtered. The solvent was removed under reduced pressure to afford the title compound;
LC-MS: Rt=0.82 mins; MS m/z [M+H]+206.0; Method 2minLowpH Step 2: 5-Bromo-N-(2-cyclohexyl-1,5-dimethyl-3-oxo-2,3-dihydro-1H-pyrazol-4-yl)-4-methylisoxazole-3-carboxamide A solution of DMF (5.33 mL, 68.8 mmol) in DCM (200 mL) was cooled to 0° C. and treated with oxalyl chloride (3.31 ml, 37.9 mmol). 5-bromo-4-methylisoxazole-3-carboxylic acid (7.09 g, 34.4 mmol) was added and stirred under ice cooling for 10 mins. 4-Amino-2-cyclohexyl-1,5-dimethyl-1H-pyrazol-3(2H)-one (Intermediate D) (7.92 g, 37.9 mmol) and triethylamine (14.39 ml, 103 mmol) were added at 0° C.

and the mixture stirred at this temperature for 30 mins. The resulting mixture was diluted with DCM and washed with a saturated NaHCO₃ (aq) solution. The organic layer was dried over MgSO₄, filtered and the solvent removed under reduced pressure. The crude material was adsorbed onto silica and purification by chromatography eluting with 100% TBME afforded the title compound;

LC-MS: Rt=0.93 mins; MS m/z [M+H]+397.2/400.2; Method 2minLowpH

Step 3: 5-Cyclohexyl-N-(2-cyclohexyl-1,5-dimethyl-3-oxo-2,3-dihydro-1H-pyrazol-4-yl)-4-methylisoxazole-3-carboxamide To 5-bromo-N-(2-cyclohexyl-1,5-dimethyl-3-oxo-2,3-dihydro-1H-pyrazol-4-yl)-4-methylisoxazole-3-carboxamide (75 mg, 0.189 mmol) was added cyclohexylzinc(II) bromide (0.5M in THF) (1133 μL, 0.566 mmol) and bis(tri-t-butylphosphine)palladium(0) (9.65 mg, 0.019 mmol) and the mixture was stirred at 100° C. in the microwave for 30 minutes. The resulting mixture was diluted with EtOAc and filtered and the solvent was removed under reduced pressure. The crude material was adsorbed onto silica and purification by chromatography eluting with 0-100% EtOAc in iso-hexane afforded the title compound;

LC-MS: Rt=1.12 mins; MS m/z [M+H]+401.0/402.4; Method 2minLowpH $^1$H NMR (400 MHz, DMSO-d6) δ 9.40 (1H, s), 3.90 (1H, m), 3.20 (3H, s), 2.90 (1H, m), 2.05 (3H, s), 2.00 (3H, s), 2.80-1.00 (20H, m).

Example 11

N-(2-Cyclohexyl-1,5-dimethyl-3-oxo-2,3-dihydro-1H-pyrazol-4-yl)-4-methyl-5-(1,4-dioxaspiro[4.5]decan-8-yl)isoxazole-3-carboxamide

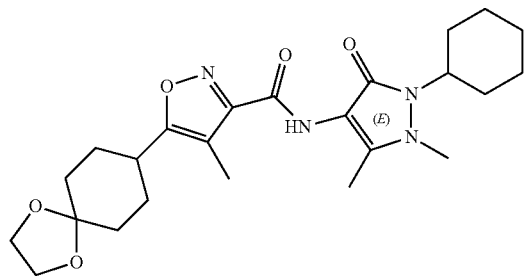 [SMILES: Cc1c(C(=O)Nc2c(C)n(C)n(C3CCCCC3)c2=O)noc1C1CCC2(CC1)OCCO2]

Step 1: 1,4-Dioxaspiro[4.5]dec-7-en-8-yl trifluoromethanesulfonate

A stirred solution of 1,4-cyclohexadione monoethylene acetal (Aldrich) (2 g, 12.81 mmol) in dry THF (30 mL) under nitrogen was cooled to −70° C. and 0.6M LDA (in heptane/THF/ethylbenzene) (25.6 mL, 15.37 mmol) was added dropwise keeping the temperature below −65° C. The reaction mixture was stirred for 20 mins at −70° C. before treating dropwise with a solution of 2-[N,N-bis(trifluoromethylsulfonyl)amino]pyridine (Alfa Aesar) (5.05 g, 14.09 mmol) in dry THF (10 mL) over 30 minutes, ensuring the temperature did not exceed −65° C. The reaction mixture was stirred at −70° C. for 1 hour before allowing to warm to room temperature gradually and was stirred overnight. The resulting mixture was quenched with saturated aqueous NaHCO₃ (100 mL) and extracted with TBME (2×150 mL). The combined organic extracts were washed with 10% NaOH (aq) (100 mL), brine (100 mL), dried over MgSO₄, filtered and the solvent was removed under reduced pressure. The crude material was adsorbed onto silica and purification by chromatography eluting with 0-10% EtOAc in iso-hexane afforded the title compound;

$^1$H NMR (400 MHz, DMSO-d6) δ 5.80 (1H, mult), 3.91 (4H, mult), 2.51-2.49 (2H, mult), 2.49-2.43 (2H, br mults), 2.37-2.34 (2H, br mults), 1.86-1.81 (2H, mults).

Step 2: 4,4,5,5-Tetramethyl-2-(1,4-dioxaspiro[4.5]dec-7-en-8-yl)-1,3,2-dioxaborolane To a stirred solution of 1,4-dioxaspiro[4.5]dec-7-en-8-yl trifluoromethanesulfonate (1.19 g, 4.13 mmol) in dry dioxane (15 mL), bis(pinacolato)diboron (Alfa Aesar) (1.048 g, 4.13 mmol) was added followed by potassium acetate (Acros) (0.810 g, 8.26 mmol) and PdCl₂(dppf).CH₂Cl₂ adduct (Alfa Aesar) (0.101 g, 0.124 mmol). The reaction mixture was flushed with nitrogen and stirred at 80° C. overnight. The resulting mixture was cooled to room temperature and filtered through Celite®, washing with TBME. The organic filtrate was concentrated under reduced pressure and partitioned between EtOAc (50 mL) and water (50 mL). The organic phase was washed with brine (30 mL), dried over MgSO₄, filtered and concentrated under reduced pressure. The crude material was adsorbed onto silica and purification by chromatography eluting with 0-30% EtOAc in iso-hexane afforded the title compound.

Step 3: Ethyl 4-methyl-5-(1,4-dioxaspiro[4.5]dec-7-en-8-yl)isoxazole-3-carboxylate To a 2-5 mL microwave vial containing a solution of 4,4,5,5-tetramethyl-2-(1,4-dioxaspiro[4.5]dec-7-en-8-yl)-1,3,2-dioxaborolane (586 mg, 2.200 mmol) in acetonitrile (2 mL) was added ethyl 5-bromo-4-methylisoxazole-3-carboxylate (Intermediate D) (515 mg, 2.200 mmol) followed by K₂CO₃ (912 mg, 6.60 mmol), PdCl₂(dppf).CH₂Cl₂ adduct (17.97 mg, 0.022 mmol), and water (0.667 mL). The vial was flushed with nitrogen and stirred in the microwave (Biotage Smith Initiator) at 80° C. for 1 hour and 100° C. for 30 minutes. The resulting mixture was partitioned between water (30 mL) and EtOAc (30 mL). The organic phase was washed with brine (30 mL), dried over MgSO₄, filtered and concentrated under reduced pressure to give an orange oil. The crude material was adsorbed onto silica and purification by chromatography eluting with 0-40% EtOAc in iso-hexane afforded the title compound;

$^1$H NMR (400 MHz, DMSO-d6) δ 6.26 (1H, mult), 4.37 (2H, q), 3.93 (4H, s), 2.62-2.56 (2H, br mults), 2.47-2.43 (2H, mults), 2.23 (3H, s), 1.82 (2H, mult), 1.23 (3H, t).

Step 4: Ethyl 4-methyl-5-(1,4-dioxaspiro[4.5]decan-8-yl)isoxazole-3-carboxylate

A solution of ethyl 4-methyl-5-(1,4-dioxaspiro[4.5]dec-7-en-8-yl)isoxazole-3-carboxylate (556 mg, 1.896 mmol) in ethanol (20 mL) was flushed with nitrogen and then treated with 10% Pd—C, 50% wet (Alfa Aesar, 38303) (303 mg, 2.84 mmol). The reaction mixture was stirred under an atmosphere of hydrogen at room temperature overnight. The resulting mixture was filtered through Celite®, washing with ethanol and DCM. The filtrate was concentrated under reduced pressure and the residue was passed through a 500 mg silica-TMT cartridge, eluting with ethanol:ether (1:1). The solvent was removed under reduced pressure to afford the title compound;

LC-MS: Rt=1.11 mins; MS m/z [M+H]+296.2; Method 2minLowpHv01

Step 5: 4-Methyl-5-(1,4-dioxaspiro[4.5]decan-8-yl)isoxazole-3-carboxylic acid To a stirred solution of ethyl 4-methyl-5-(1,4-dioxaspiro[4.5]decan-8-yl)isoxazole-3-carboxylate (558 mg, 1.889 mmol) in THF (5 mL), 2M NaOH (aq) (4.179 ml, 8.36 mmol) was added and the reaction mixture was stirred at room temperature for 15 minutes. The resulting mixture was poured into water (20 mL) and the pH adjusted to pH 5-6 by the addition of 1M HCl. The aqueous was extracted with EtOAc (30 mL) and the combined organic extracts were washed with brine (20 mL), dried over MgSO$_4$ and filtered. The solvent was removed under reduced pressure to afford the title compound;

LC-MS: Rt=0.89 minutes; MS m/z [M+H]+268.2; Method 2minLowpHv01

Step 6: N-(2-Cyclohexyl-1,5-dimethyl-3-oxo-2,3-dihydro-1H-pyrazol-4-yl)-4-methyl-5-(1,4-dioxaspiro[4.5]decan-8-yl)isoxazole-3-carboxamide To a stirred solution of 4-methyl-5-(1,4-dioxaspiro[4.5]decan-8-yl)isoxazole-3-carboxylic acid (239 mg, 0.894 mmol) in dry NMP (3 mL), HATU (374 mg, 0.984 mmol) was added followed by 4-amino-2-cyclohexyl-1,5-dimethyl-1H-pyrazol-3(2H)-one (Intermediate D) (206 mg, 0.984 mmol) and triethylamine (0.274 mL, 1.967 mmol). The mixture was stirred at room temperature for 16 hours. The resulting mixture was partitioned between EtOAc (20 mL) and 1M NaOH (20 mL). The organic phase was washed with water (30 mL), brine (30 mL), dried over MgSO$_4$, filtered and concentrated under reduced pressure. The crude material was adsorbed onto silica and purification by chromatography eluting with 0-2% MeOH in DCM afforded crude material. Isolated material was dissolved in DMSO (2 mL) and triturated with water (30 mL). The resulting suspension was filtered under reduced pressure and the solid was washed with water (20 mL) and allowed to dry under vacuum to afford the title compound;

LC-MS: Rt=0.96 minutes; MS m/z [M+H]+459.5: Method 2minLowpHv01

$^1$H NMR (400 MHz, DMSO-d6) δ 9.41 (1H, s), 3.96-3.86 (5H, mults), 3.21 (3H, s), 3.02 (1H, mult), 2.07 (3H, s), 2.05-1.92 (2H, br mults), 2.02 (3H, s), 1.84-1.72 (8H, br mults), 1.70-1.57 (5H, br mults), 1.38-1.23 (2H, br mults), 1.22-1.11 (1H, br mult).

Example 12

A mixture of 5-((2S,4S,6R)-6-(tert-butyl)-4-methoxytetrahydro-2H-pyran-2-yl)-N-(2-cyclohexyl-1,5-dimethyl-3-oxo-2,3-dihydro-1H-pyrazol-4-yl)-4-methylisoxazole-3-carboxamide and 5-((2R,4R,6S)-6-(tert-butyl)-4-methoxytetrahydro-2H-pyran-2-yl)-N-(2-cyclohexyl-1,5-dimethyl-3-oxo-2,3-dihydro-1H-pyrazol-4-yl)-4-methylisoxazole-3-carboxamide

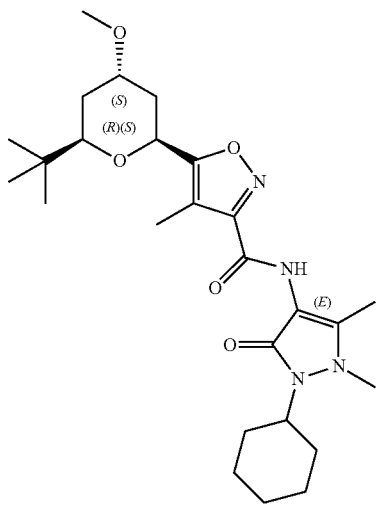

and

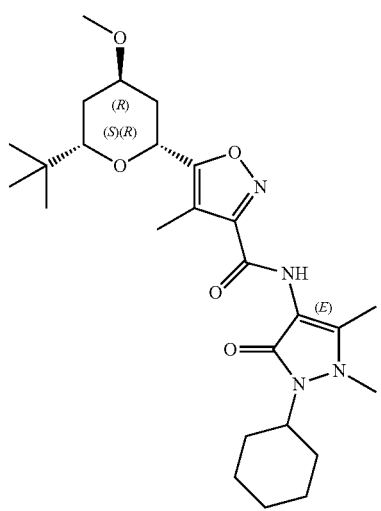

Step 1: Ethyl 5-(1-hydroxybut-3-en-1-yl)-4-methyl-isoxazole-3-carboxylate

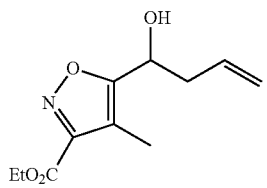 [SMILES: C=CCC(O)c1onc(C(=O)OCC)c1C]

To a solution of ethyl 5-formyl-4-methylisoxazole-3-carboxylate (Intermediate C) (350 mg, 1.911 mmol) in DCM (19 mL) was added allyltrimethylsilane (276 μl, 1.911 mmol) and the mixture was cooled to −78° C. A solution of boron trifluoride etherate (278 μl, 2.198 mmol) in DCM (5 mL) was cooled to −78° C. and added to the reaction mixture over 5 min. The reaction mixture was stirred for 15 mins and triethylamine (266 μl, 1.911 mmol) was added. The reaction mixture was maintained at −78° C. for 15 minutes and allowed to warm to room temperature. The resulting mixture was quenched by the addition of a saturated aqueous NaHCO$_3$ solution (10 mL) and extracted with DCM (2×10 mL). The combined organic extracts were passed through a phase separating cartridge and the solvent removed under reduced pressure. The crude material was adsorbed onto silica and purification by chromatography eluting with 0-40% EtOAc in iso-hexane afforded the title compound;

LC-MS: Rt=1.06 mins; MS m/z [M+H]+225.8/226.4; Method 2minLowpHv03

Step 2

2a: A racemic mixture of ethyl 5-((2S,4S,6R)-6-(tert-butyl)-4-methoxytetrahydro-2H-pyran-2-yl)-4-methylisoxazole-3-carboxylate and ethyl 5-((2R,4R,6S)-6-(tert-butyl)-4-methoxytetrahydro-2H-pyran-2-yl)-4-methylisoxazole-3-carboxylate

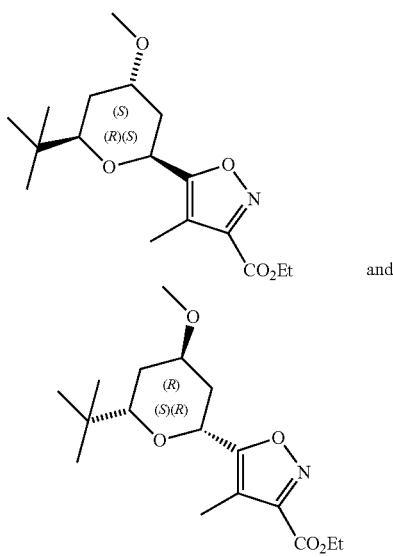

and 2b: A racemic mixture of ethyl 5-((2S,4R,6S)-6-(tert-butyl)-4-methoxytetrahydro-2H-pyran-2-yl)-4-methylisoxazole-3-carboxylate and ethyl 5-((2R,4S,6R)-6-(tert-butyl)-4-methoxytetrahydro-2H-pyran-2-yl)-4-methylisoxazole-3-carboxylate

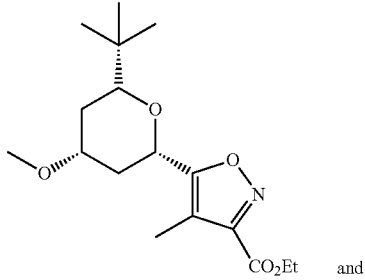

and

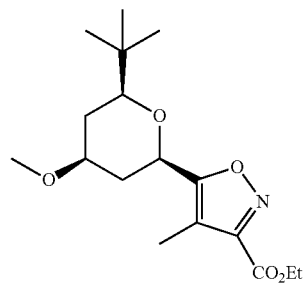

To a solution of ethyl 5-(1-hydroxybut-3-en-1-yl)-4-methylisoxazole-3-carboxylate (140 mg, 0.622 mmol) in DCM (6.2 mL) was added pivalaldehyde (67.5 μl, 0.622 mmol). TMSOTf (112 μl, 0.622 mmol) was added dropwise and the reaction mixture was stirred for 1 hour at room temperature. MeOH (2 mL) was added and the resulting mixture was partitioned between water (5 mL) and DCM, layers separated and the aqueous extracted with DCM (2×5 mL). The combined organic extracts were dried over Na$_2$SO$_4$, filtered and the solvent removed under reduced pressure. The crude material was adsorbed onto silica and purification by chromatography eluting with 0-50% EtOAc in iso-hexane afforded the title compounds;

2a: A racemic mixture of ethyl 5-((2S,4S,6R)-6-(tert-butyl)-4-methoxytetrahydro-2H-pyran-2-yl)-4-methylisoxazole-3-carboxylate and ethyl 5-((2R,4R,6S)-6-(tert-butyl)-4-methoxytetrahydro-2H-pyran-2-yl)-4-methylisoxazole-3-carboxylate LC-MS: Rt=1.64 mins; MS m/z [M+H]+326.6;

Method 2minLowpHv03

2b: A racemic mixture of ethyl 5-((2S,4R,6S)-6-(tert-butyl)-4-methoxytetrahydro-2H-pyran-2-yl)-4-methylisoxazole-3-carboxylate and ethyl 5-((2R,4S,6R)-6-(tert-butyl)-

4-methoxytetrahydro-2H-pyran-2-yl)-4-methylisoxazole-3-carboxylate LC-MS: Rt=1.54 mins; MS m/z [M+H]+326.6; Method 2minLowpHv03

Step 3: A racemic mixture of 5-((2S,4S,6R)-6-(tert-butyl)-4-methoxytetrahydro-2H-pyran-2-yl)-4-methylisoxazole-3-carboxylic acid and 5-((2R,4R,6S)-6-(tert-butyl)-4-methoxytetrahydro-2H-pyran-2-yl)-4-methylisoxazole-3-carboxylic acid

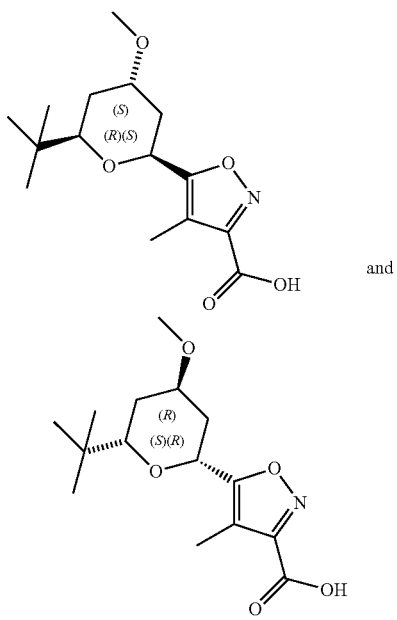

and

To a solution of a racemic mixture of 2a: ethyl 5-((2S,4S,6R)-6-(tert-butyl)-4-methoxytetrahydro-2H-pyran-2-yl)-4-methylisoxazole-3-carboxylate and ethyl 5-((2R,4R,6S)-6-(tert-butyl)-4-methoxytetrahydro-2H-pyran-2-yl)-4-methylisoxazole-3-carboxylate (9 mg, 0.028 mmol) in MeOH (0.45 mL) and THF (0.75 mL), 2M NaOH (aq) (59.9 µl, 0.120 mmol) was added. The reaction mixture was stirred at room temperature for 2 hours. The resulting mixture was concentrated under reduced pressure to give a residue which was diluted with 2M NaOH (aq) (5 mL) and washed with DCM (5 mL). The aqueous layer was acidified with 2 M HCl (aq) (8 mL) and extracted with DCM (3×5 mL). The combined organic extracts were passed through a phase separating cartridge and the solvent was removed under reduced pressure to afford a racemic mixture of 5-((2S,4S,6R)-6-(tert-butyl)-4-methoxytetrahydro-2H-pyran-2-yl)-4-methylisoxazole-3-carboxylic acid and 5-((2R,4R,6S)-6-(tert-butyl)-4-methoxytetrahydro-2H-pyran-2-yl)-4-methylisoxazole-3-carboxylic acid;

LC-MS: Rt=1.44 mins; MS m/z [M+H]+298.5; Method 2minLowpHv03

Step 4: Racemic mixture of 5-((2S,4S,6R)-6-(tert-butyl)-4-methoxytetrahydro-2H-pyran-2-yl)-N-(2-cyclohexyl-1,5-dimethyl-3-oxo-2,3-dihydro-1H-pyrazol-4-yl)-4-methylisoxazole-3-carboxamide and 5-((2R,4R,6S)-6-(tert-butyl)-4-methoxytetrahydro-2H-pyran-2-yl)-N-(2-cyclohexyl-1,5-dimethyl-3-oxo-2,3-dihydro-1H-pyrazol-4-yl)-4-methylisoxazole-3-carboxamide To a solution of a racemic mixture of 5-((2S,4S,6R)-6-(tert-butyl)-4-methoxytetrahydro-2H-pyran-2-yl)-4-methyl-isoxazole-3-carboxylic acid and 5-((2R,4R,6S)-6-(tert-butyl)-4-methoxytetrahydro-2H-pyran-2-yl)-4-methylisoxazole-3-carboxylic acid (9 mg, 0.030 mmol) in NMP (0.3 mL), HATU (12.66 mg, 0.033 mmol) was added, followed by 4-amino-2-cyclohexyl-1,5-dimethyl-1H-pyrazol-3(2H)-one (Intermediate D) (6.33 mg, 0.030 mmol) and Et₃N (8.39 µl, 0.061 mmol). The reaction mixture was stirred at room temperature overnight. The resulting mixture was partitioned between EtOAc (10 mL) and a saturated aqueous NaHCO₃ solution (10 mL). The organic layer was washed with brine (10 mL), dried over MgSO₄, filtered and the solvent removed under reduced pressure. The crude material was adsorbed onto silica and purification by chromatography eluting with 0-10% MeOH in DCM afforded the title compound;

LC-MS: Rt=4.57 mins; MS m/z [M+H]+489.3; Method 8minLowpHv01

¹H NMR (400 MHz, CDCl₃) δ 8.06 (1H, br s), 4.98 (1H, dd), 4.06 (1H, tt), 3.82 (1H, mult), 3.50 (1H, dd), 3.40 (3H, s), 3.26 (3H, s), 2.28 (3H, s), 2.21 (3H, s), 2.14-2.07 (1H, mults), 2.05-1.82 (8H, br mults), 1.71 (1H, br mult), 1.51 (1H, mult), 1.43-1.29 (2H, br mults), 1.29-1.17 (1H, br mult), 0.92 (9H, s).

Example 13

A mixture of 5-((2S,4R,6R)-6-(tert-butyl)-4-methoxytetrahydro-2H-pyran-2-yl)-N-(2-cyclohexyl-1,5-dimethyl-3-oxo-2,3-dihydro-1H-pyrazol-4-yl)-4-methylisoxazole-3-carboxamide and 5-((2R,4S,6S)-6-(tert-butyl)-4-methoxytetrahydro-2H-pyran-2-yl)-N-(2-cyclohexyl-1,5-dimethyl-3-oxo-2,3-dihydro-1H-pyrazol-4-yl)-4-methylisoxazole-3-carboxamide

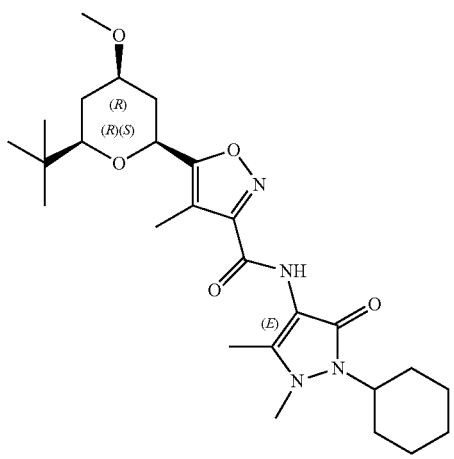

and

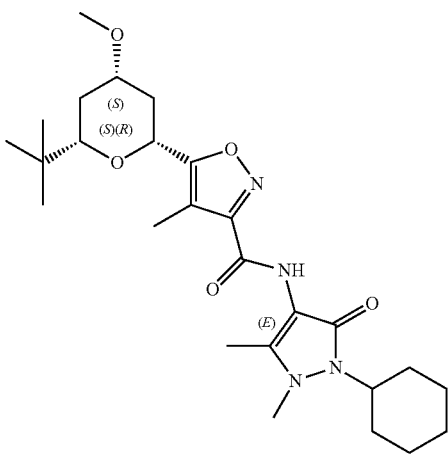

Example 13 was prepared by a similar method to that of Example 12 by replacing 2a with 2b in step 3;

LC-MS: Rt=4.40 mins; MS m/z [M+H]+489.4; Method 8minLowpHv01

Example 13a 5-((2S,4R,6R)-6-(tert-Butyl)-4-methoxytetrahydro-2H-pyran-2-yl)-N-(2-cyclohexyl-1,5-dimethyl-3-oxo-2,3-dihydro-1H-pyrazol-4-yl)-4-methylisoxazole-3-carboxamide or 5-((2R,4S,6S)-6-(tert-butyl)-4-methoxytetrahydro-2H-pyran-2-yl)-N-(2-cyclohexyl-1,5-dimethyl-3-oxo-2,3-dihydro-1H-pyrazol-4-yl)-4-methylisoxazole-3-carboxamide and Example 13b: 5-((2S,4R,6R)-6-(tert-Butyl)-4-methoxytetrahydro-2H-pyran-2-yl)-N-(2-cyclohexyl-1,5-dimethyl-3-oxo-2,3-dihydro-1H-pyrazol-4-yl)-4-methylisoxazole-3-carboxamide or 5-((2R,4S,6S)-6-(tert-butyl)-4-methoxytetrahydro-2H-pyran-2-yl)-N-(2-cyclohexyl-1,5-dimethyl-3-oxo-2,3-dihydro-1H-pyrazol-4-yl)-4-methylisoxazole-3-carboxamide

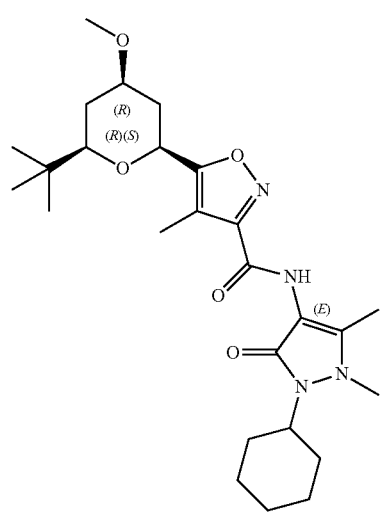

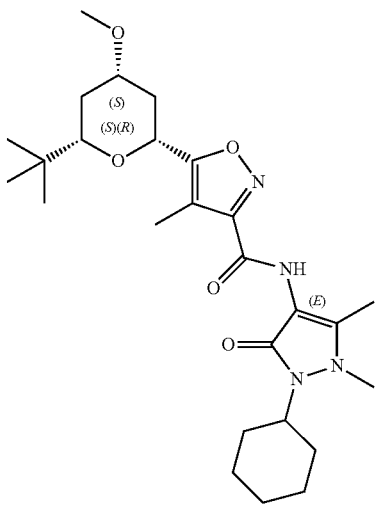

Chiral separation of Example 13 using Supercritical Fluid Chromatography afforded the individual enantiomers:

Method Details:

Column: Chiralcel OD-H 250×10 mm, 5 um @35 deg C.

Mobile phase: 35% Isopropanol+0.1% v/v DEA/65% $CO_2$

Flow: 10 ml/min

Detection: UV @220 nm

Instrument: Berger Minigram SFC1

Example 13a 5-((2S,4R,6R)-6-(tert-butyl)-4-methoxytetrahydro-2H-pyran-2-yl)-N-(2-cyclohexyl-1,5-dimethyl-3-oxo-2,3-dihydro-1H-pyrazol-4-yl)-4-methylisoxazole-3-carboxamide or 5-((2R,4S,6S)-6-(tert-butyl)-4-methoxytetrahydro-2H-pyran-2-yl)-N-(2-cyclohexyl-1,5-dimethyl-3-oxo-2,3-dihydro-1H-pyrazol-4-yl)-4-methylisoxazole-3-carboxamide SFC Retention Time=4.86 mins LCMS: Rt 1.42 mins MS m/z [M+H]+489.5; Method 2minLowpHv03

Example 13b 5-((2S,4R,6R)-6-(tert-butyl)-4-methoxytetrahydro-2H-pyran-2-yl)-N-(2-cyclohexyl-1,5-dimethyl-3-oxo-2,3-dihydro-1H-pyrazol-4-yl)-4-methylisoxazole-3-carboxamide or 5-((2R,4S,6S)-6-(tert-butyl)-4-methoxytetrahydro-2H-pyran-2-yl)-N-(2-cyclohexyl-1,5-dimethyl-3-oxo-2,3-dihydro-1H-pyrazol-4-yl)-4-methylisoxazole-3-carboxamide SFC Retention Time=2.85 mins LCMS: Rt 1.42 mins MS m/z [M+H]+489.5; Method 2minLowpHv03

Example 14

A diastereomeric mixture of 5-((2R,4R,6S)-6-(tert-butyl)-4-methoxytetrahydro-2H-pyran-2-yl)-N-(2-cyclobutyl-1,5-dimethyl-3-oxo-2,3-dihydro-1H-pyrazol-4-yl)-4-methylisoxazole-3-carboxamide and 5-((2S,4S,6R)-6-(tert-butyl)-4-methoxytetrahydro-2H-pyran-2-yl)-N-(2-cyclobutyl-1,5-dimethyl-3-oxo-2,3-dihydro-1H-pyrazol-4-yl)-4-methylisoxazole-3-carboxamide

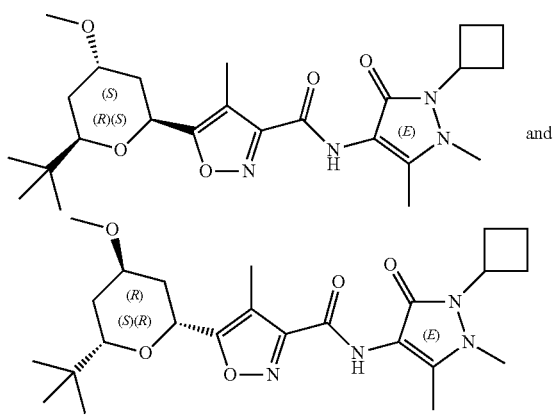

Step 1: A mixture of ethyl 5-((2R,4S,6S)-6-(tert-butyl)-4-(2,2,2-trifluoroacetoxy)tetrahydro-2H-pyran-2-yl)-4-methylisoxazole-3-carboxylate and ethyl 5-((2S,4R,6R)-6-(tert-butyl)-4-(2,2,2-trifluoroacetoxy)tetrahydro-2H-pyran-2-yl)-4-methylisoxazole-3-carboxylate Ethyl 5-formyl-4-methylisoxazole-3-carboxylate (100 mg, 0.546 mmol) and 2,2-dimethylhex-5-en-3-ol (Intermediate F) (70.0 mg, 0.546 mmol) were combined in DCM (12 mL) and treated with oven-dried molecular sieves (100 mg, 0.546 mmol) and TFA (3.15 mL, 40.9 mmol). The reaction mixture was stirred at room temperature for 2 hours. Pivaldehyde (0.059 mL, 0.546 mmol) was added and the reaction mixture was stirred at room temperature overnight. The resulting mixture was quenched with a saturated aqueous NaHCO₃ solution and extracted with DCM (×3). The combined organic extracts were dried over MgSO₄ and filtered. The solvent was removed under reduced pressure to afford the title compound.

Step 2: A mixture of ethyl 5-((2R,4S,6S)-6-(tert-butyl)-4-hydroxytetrahydro-2H-pyran-2-yl)-4-methylisoxazole-3-carboxylate and ethyl 5-((2S,4R,6R)-6-(tert-butyl)-4-hydroxytetrahydro-2H-pyran-2-yl)-4-methylisoxazole-3-carboxylate Sodium (45.7 mg, 1.988 mmol) was dissolved in ethanol and the resulting solution was added at room temperature to a mixture of ethyl 5-((2R,4S,6S)-6-(tert-butyl)-4-(2,2,2-trifluoroacetoxy)tetrahydro-2H-pyran-2-yl)-4-methylisoxazole-3-carboxylate and ethyl 5-((2S,4R,6R)-6-(tert-butyl)-4-(2,2,2-trifluoroacetoxy)tetrahydro-2H-pyran-2-yl)-4-methylisoxazole-3-carboxylate (270 mg, 0.663 mmol) in EtOH (5 mL). The reaction mixture was stirred at room temperature for 2 hrs. 0.1M HCl (aq)(50 mL) was added and the aqueous was separated and extracted with EtOAc (×3). The combined organic extracts were dried over MgSO₄, filtered and the solvent removed under reduced pressure. The crude material was adsorbed onto silica and purification by chromatography eluting with 0-100% EtOAc in iso-hexane afforded the title compound.

Step 4: A mixture of ethyl 5-((2R,6S)-6-(tert-butyl)-4-oxotetrahydro-2H-pyran-2-yl)-4-methylisoxazole-3-carboxylate and ethyl 5-((2S,6R)-6-(tert-butyl)-4-oxotetrahydro-2H-pyran-2-yl)-4-methylisoxazole-3-carboxylate A mixture of ethyl 5-((2R,4S,6S)-6-(tert-butyl)-4-hydroxytetrahydro-2H-pyran-2-yl)-4-methylisoxazole-3-carboxylate and ethyl 5-((2S,4R,6R)-6-(tert-butyl)-4-hydroxytetrahydro-2H-pyran-2-yl)-4-methylisoxazole-3-carboxylate (35 mg, 0.112 mmol) in DCM (20 mL) was treated at room temperature with Dess-Martin reagent (47.7 mg, 0.112 mmol) and stirred for 30 mins. Saturated aqueous sodium metabisulfite solution was added and the mixture was stirred for 15 mins. The resulting layers were separated and the organic layer was washed with a saturated aqueous NaHCO₃ solution. The aqueous portion was extracted with DCM and the combined organic extracts were dried over MgSO₄, filtered and the solvent removed under reduced pressure. The crude material was adsorbed onto silica and purification by chromatography eluting with 0-40% EtOAc in iso-hexane afforded the title compound;

$^1$H NMR (400 MHz, CDCl₃) δ 4.78 (1H, dd), 4.38 (2H, q), 3.34 (1H, dd), 2.83 (1H, mult), 2.62-2.56 (1H, mults), 2.45-2.33 (2H, br mults), 2.21 (3H, s), 1.35 (3H, t), 0.90 (9H, s).

Step 5: A diastereomeric mixture of 5-((2R,4R,6S)-6-(tert-butyl)-4-hydroxytetrahydro-2H-pyran-2-yl)-4-methylisoxazole-3-carboxylic acid compound and 5-((2S,4S,6R)-6-(tert-butyl)-4-hydroxytetrahydro-2H-pyran-2-yl)-4-methylisoxazole-3-carboxylic acid (1:1)

A mixture of ethyl 5-((2R,6S)-6-(tert-butyl)-4-oxotetrahydro-2H-pyran-2-yl)-4-methylisoxazole-3-carboxylate and ethyl 5-((2S,6R)-6-(tert-butyl)-4-oxotetrahydro-2H-pyran-2-yl)-4-methylisoxazole-3-carboxylate (420 mg, 1.358 mmol) in THF (20 mL) was cooled to −78° C. and treated with 1M L-Selectride in THF (1.426 mL, 1.426 mmol) and stirred at −78° C. for 3 hrs. The resulting mixture was quenched with acetic acid and washed with 1M HCl (aq). The aqueous was extracted with EtOAc (×2). All organic layers were combined, dried over MgSO₄, filtered and the solvent removed under reduced pressure. The crude material was adsorbed onto silica and purification by chromatography eluting with 0-50% EtOAc in iso-hexane afforded crude material. The crude material was dissolved in THF, treated with 2M NaOH (aq) and stirred at room temperature for 2 hours. The resulting mixture was acidified using 1M HCl (aq) and extracted with EtOAc. The combined organic extracts were dried over MgSO₄ and filtered and the solvent was removed under reduced pressure to afford the title compound;

LC-MS: Rt=1.10 mins; MS m/z [M+H]+284.3; Method 2minLowpHv03

Step 6: A diastereomeric mixture of methyl 5-((2R, 4R,6S)-6-(tert-butyl)-4-methoxytetrahydro-2H-pyran-2-yl)-4-methylisoxazole-3-carboxylate compound and methyl 5-((2R,4S,6S)-6-(tert-butyl)-4-methoxytetrahydro-2H-pyran-2-yl)-4-methylisoxazole-3-carboxylate (1:1) and methyl 5-((2S,4R,6R)-6-(tert-butyl)-4-methoxytetrahydro-2H-pyran-2-yl)-4-methylisoxazole-3-carboxylate compound and methyl 5-((2S,4S,6R)-6-(tert-butyl)-4-methoxytetrahydro-2H-pyran-2-yl)-4-methylisoxazole-3-carboxylate (1:1)

A diastereomeric mixture of 5-((2R,4R,6S)-6-(tert-butyl)-4-hydroxytetrahydro-2H-pyran-2-yl)-4-methylisoxazole-3-carboxylic acid compound and 5-((2S,4S,6R)-6-(tert-butyl)-4-hydroxytetrahydro-2H-pyran-2-yl)-4-methylisoxazole-3-carboxylic acid (1:1) (31 mg, 0.109 mmol) in DMF (0.5 mL) was added to a solution of sodium hydride (10.94 mg, 0.274 mmol) in DMF (2 mL) at 0° C. The mixture was allowed to warm to room temperature, stirred for 2 hours and iodomethane (0.068 mL, 1.094 mmol) was added. The reaction was stirred at room temperature overnight. The resulting mixture was quenched with 2M HCl (aq) and extracted with EtOAc. The combined organic extracts were washed with 0.5M LiCl (aq), brine, dried over MgSO$_4$, filtered and the solvent removed under reduced pressure. The crude material was adsorbed onto silica and purification by chromatography eluting with 0-30% EtOAc in iso-hexane afforded the title compound.

Step 7: A diastereomeric mixture of 5-((2R,4R,6S)-6-(tert-butyl)-4-methoxytetrahydro-2H-pyran-2-yl)-4-methylisoxazole-3-carboxylic acid and 5-((2S,4S,6R)-6-(tert-butyl)-4-methoxytetrahydro-2H-pyran-2-yl)-4-methylisoxazole-3-carboxylic acid A diastereomeric mixture of methyl 5-((2R,4R,6S)-6-(tert-butyl)-4-methoxytetrahydro-2H-pyran-2-yl)-4-methylisoxazole-3-carboxylate compound and methyl 5-((2R,4S,6S)-6-(tert-butyl)-4-methoxytetrahydro-2H-pyran-2-yl)-4-methylisoxazole-3-carboxylate (1:1) and methyl 5-((2S,4R,6R)-6-(tert-butyl)-4-methoxytetrahydro-2H-pyran-2-yl)-4-methylisoxazole-3-carboxylate compound and methyl 5-((2S,4S,6R)-6-(tert-butyl)-4-methoxytetrahydro-2H-pyran-2-yl)-4-methylisoxazole-3-carboxylate (1:1) (14 mg, 0.045 mmol) in THF (1 mL) and MeOH (0.6 mL) was treated with 2M NaOH (aq) (0.090 mL, 0.180 mmol) at room temperature for 1 hour. The resulting mixture was treated with 2M HCl (aq) (4 mL) and extracted with EtOAc (×2). The combined organic extracts were dried over MgSO$_4$ and filtered. The solvent was removed under reduced pressure to afford the title compound;

Step 8: A diastereomeric mixture of 5-((2R,4R,6S)-6-(tert-butyl)-4-methoxytetrahydro-2H-pyran-2-yl)-4-methylisoxazole-3-carboxylic acid and 5-((2R,4S,6S)-6-(tert-butyl)-4-methoxytetrahydro-2H-pyran-2-yl)-4-methylisoxazole-3-carboxylic acid and 5-((2S,4R,6R)-6-(tert-butyl)-4-methoxytetrahydro-2H-pyran-2-yl)-4-methylisoxazole-3-carboxylic acid and 5-((2S,4S,6R)-6-(tert-butyl)-4-methoxytetrahydro-2H-pyran-2-yl)-4-methylisoxazole-3-carboxylic acid (20 mg, 0.067 mmol) and 4-amino-2-cyclobutyl-1,5-dimethyl-1H-pyrazol-3(2H)-one (Intermediate E) (12.80 mg, 0.071 mmol) in DMF (0.5 mL) were treated with DIPEA (0.047 mL, 0.269 mmol) and HATU (33.2 mg, 0.087 mmol)

The reaction mixture was stirred at room temperature overnight. The resulting mixture was treated with water and extracted with EtOAc (×2). The combined organic extracts were washed with 0.5M Lithium Chloride (aq), brine, dried over MgSO$_4$, filtered and solvent was removed under reduced pressure. The crude material was adsorbed onto silica and purification by chromatography eluting with 0-100% EtOAc in iso-hexane afforded the title compound;

LC-MS: Rt=1.38 mins; MS m/z [M+H]+461.6; Method 2minLowpHv03

$^1$H NMR (400 MHz, CDCl$_3$) δ 8.10 (1H, br s), 4.99 (1H, d), 4.63 (1H, mult), 3.82 (1H, mult), 3.51 (1H, d), 3.41 (3H, s), 3.28 (3H, s), 2.88-2.75 (2H, br mults), 2.41-2.31 (2H, br mults), 2.28 (3H, s), 2.22 (3H, s), 2.14-2.06 (1H, br mult), 1.99-1.83 (3H, br mults), 1.83-1.72 (1H, br mult), 1.52 (1H, mult), 0.92 (9H, s).

Example 15

5-(6-(tert-butyl)tetrahydro-2H-pyran-2-yl)-N-(2-cyclobutyl-1,5-dimethyl-3-oxo-2,3-dihydro-1H-pyrazol-4-yl)-4-methylisoxazole-3-carboxamide

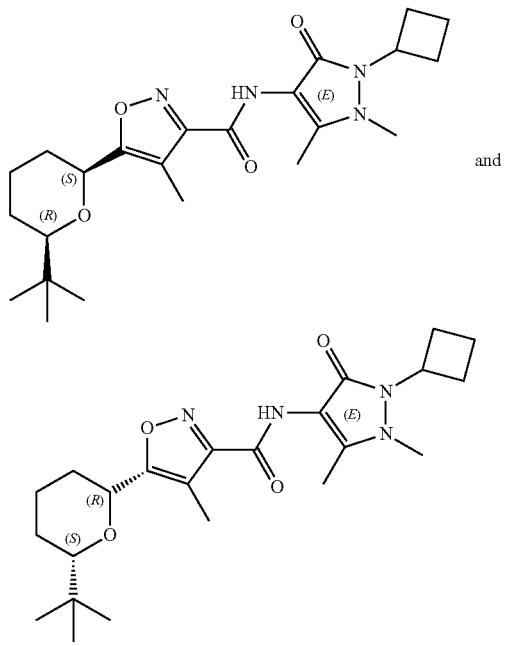

Step 1: A mixture of ethyl 5-((2R,6S)-4-bromo-6-(tert-butyl)tetrahydro-2H-pyran-2-yl)-4-methylisoxazole-3-carboxylate and ethyl 5-((2S,6R)-4-bromo-6-(tert-butyl)tetrahydro-2H-pyran-2-yl)-4-methylisoxazole-3-carboxylate (1:1)

To an ice-cooled flask under nitrogen containing 2,2-dimethylhex-5-en-3-ol (Intermediate F) (400 mg, 3.12 mmol) and indium (III) bromide (55.4 mg, 0.156 mmol) in dry DCM (31 mL) was added bromotrimethylsilane (0.405 ml, 3.12 mmol). The reaction mixture was stirred with ice cooling for 30 mins. To a second flask a solution of ethyl 5-formyl-4-methylisoxazole-3-carboxylate (Intermediate C) (572 mg, 3.12 mmol) in dry DCM (31 mL) under nitrogen was cooled in ice. This was added to the first flask dropwise over 30 mins with ice cooling. The reaction mixture was stirred with ice cooling for 1.5 hr and at room temperature overnight. To the reaction mixture was added pivalaldehyde (0.085 ml, 0.781 mmol) and this was stirred for 2 hours. Further pivalaldehyde (0.085 ml, 0.781 mmol) was added and the reaction mixture was stirred at room temperature overnight. To the resulting mixture was added a saturated aqueous $NaHCO_3$ (aq) solution and the mixture was stirred vigorously for 2 mins. The resulting mixture was passed through a phase separating cartridge and the organic eluent was collected and concentrated under reduced pressure. The crude material was adsorbed onto silica and purification by chromatography eluting with 0-30% EtOAc in iso-hexane afforded the title compounds;

LC-MS; Rt=1.68 mins; MS m/z [M+H]+376.4; Method 2minLowpHv03

Step 2: A mixture of ethyl 5-((2R,6S)-6-(tert-butyl) tetrahydro-2H-pyran-2-yl)-4-methylisoxazole-3-carboxylate and ethyl 5-((2S,6R)-6-(tert-butyl)tetrahydro-2H-pyran-2-yl)-4-methylisoxazole-3-carboxylate (1:1)

To a mixture of ethyl 5-((2R,6S)-4-bromo-6-(tert-butyl) tetrahydro-2H-pyran-2-yl)-4-methylisoxazole-3-carboxylate and ethyl 5-((2S,6R)-4-bromo-6-(tert-butyl)tetrahydro-2H-pyran-2-yl)-4-methylisoxazole-3-carboxylate (1:1) (233 mg, 0.623 mmol) in EtOH (7.1 ml) and EtOAc (0.7 mL) under a flow of nitrogen was added 10% Pd/C (26.5 mg, 0.249 mmol) and the mixture was stirred under an atmosphere of hydrogen at room temperature for 7 hours. Sodium bicarbonate (209 mg, 2.490 mmol) was added and the reaction mixture was stirred under an atmosphere of hydrogen overnight. Further 10% Pd/C (26.5 mg, 0.249 mmol) was added and stirring continued under an atmosphere of hydrogen overnight. The resulting mixture was filtered through a Celite® cartridge, eluting with EtOAc and the organic solvent was removed under reduced pressure. The crude material was adsorbed onto silica and purification by chromatography eluting with 0-50% EtOAc in iso-hexane afforded the title compounds;

LC-MS: Rt=1.72 mins; MS m/z [M+H]+296.3; Method 2minLowpHv03

$^1$H NMR (400 MHz, $CDCl_3$) δ 4.54 (1H, d), 4.66 (2H, q), 3.01 (1H, d), 2.19 (3H, s), 1.94 (1H, mult), 1.83-1.77 (1H, mult), 1.73-1.48 (3H, mults), 1.34 (3H, t), 1.35-1.26 (1H, mults), 0.84 (9H, s).

Step 3: A mixture of 5-((2R,6S)-6-(tert-butyl)tetrahydro-2H-pyran-2-yl)-4-methylisoxazole-3-carboxylic acid and 5-((2S,6R)-6-(tert-butyl)tetrahydro-2H-pyran-2-yl)-4-methylisoxazole-3-carboxylic acid (1:1)

To a stirred solution of ethyl 5-((2R,6S)-6-(tert-butyl)tetrahydro-2H-pyran-2-yl)-4-methylisoxazole-3-carboxylate and ethyl 5-((2S,6R)-6-(tert-butyl)tetrahydro-2H-pyran-2-yl)-4-methylisoxazole-3-carboxylate (1:1)(112 mg, 0.379 mmol) in THF (2 mL) and MeOH (1.2 mL) at room temperature was added 2M NaOH (aq) (0.209 mL, 0.417 mmol). The reaction mixture was stirred at room temperature overnight. The solvent was removed under reduced pressure and the residue diluted with EtOAc and water. The layers were separated and the aqueous layer was washed with EtOAc (×2). The aqueous layer was made acidic by the addition of 2M HCl (aq) and extracted with EtOAc (×3). The combined organic extracts were dried over $MgSO_4$ and filtered. The solvent was removed under reduced pressure to afford the title compounds;

LC-MS; Rt 1.57 mins; MS m/z [M+H]+268.3; Method 2minLowpHv03

Step 4: 5-((2S,6R)-6-(tert-Butyl)tetrahydro-2H-pyran-2-yl)-N-(2-cyclobutyl-1,5-dimethyl-3-oxo-2,3-dihydro-1H-pyrazol-4-yl)-4-methylisoxazole-3-carboxamide and 5-((2R,6S)-6-(tert-butyl)tetrahydro-2H-pyran-2-yl)-N-(2-cyclobutyl-1,5-dimethyl-3-oxo-2,3-dihydro-1H-pyrazol-4-yl)-4-methylisoxazole-3-carboxamide To a solution of a mixture of 5-((2S,6R)-6-(tert-butyl)tetrahydro-2H-pyran-2-yl)-4-methylisoxazole-3-carboxylic acid and 5-((2S,6R)-6-(tert-butyl)tetrahydro-2H-pyran-2-yl)-4-methylisoxazole-3-carboxylic acid (1:1) (40 mg, 0.150 mmol) in dry DCM (3 mL) under nitrogen was added oxalyl chloride (0.014 mL, 0.165 mmol) and DMF (0.023 mL, 0.299 mmol). The reaction mixture was stirred at room temperature for 5 minutes and 4-amino-2-cyclobutyl-1,5-dimethyl-1H-pyrazol-3(2H)-one (Intermediate E) (27.1 mg, 0.150 mmol) and triethylamine (0.063 mL, 0.449 mmol) were added. The reaction mixture was stirred at room temperature for 5 minutes. To the resulting mixture was added water and it was stirred vigorously before passing through a phase separating cartridge. The organics were collected and the solvent removed under reduced pressure. The crude material was then adsorbed onto silica and purification by chromatography eluting with 0-100% EtOAc in iso-hexane afforded the crude material as a mixture of enantiomers.

Chiral separation of the material using Supercritical Fluid Chromatography afforded the individual enantiomers:

Method Details:
Column: Phenomenex LUX C2 250×10 mm column, 5 um @35 deg C.
Mobile phase: 50% Methanol+0.1% v/v DEA/50% $CO_2$
Flow: 10 ml/min
Detection: UV @220 nm
Instrument: Berger Minigram SFC System 2

Example 15a 5-((2S,6R)-6-(tert-Butyl)tetrahydro-2H-pyran-2-yl)-N-(2-cyclobutyl-1,5-dimethyl-3-oxo-2,3-dihydro-1H-pyrazol-4-yl)-4-methylisoxazole-3-carboxamide or 5-((2R,6S)-6-(tert-Butyl)tetrahydro-2H-pyran-2-yl)-N-(2-cyclobutyl-1,5-dimethyl-3-oxo-2,3-dihydro-1H-pyrazol-4-yl)-4-methylisoxazole-3-carboxamide Chiral SFC: Rt=14.26 mins
LC-MS: Rt=4.59 mins; MS m/z [M+H]+431.5; Method 8minLowpHv01
$^1$H NMR (400 MHz, $CDCl_3$) δ 8.28 (1H, br s), 4.69-4.59 (2H, mults), 3.32 (3H, s), 3.10 (1H, d), 2.83 (2H, mults), 2.41-2.34 (2H, mults), 2.29 (3H, s), 2.23 (3H, s), 2.03 (1H, br d), 1.96-1.60 (6H, mults), 1.45-1.33 (1H, mults), 0.93 (9H, s).

Example 15b 5-((2R,6S)-6-(tert-butyl)tetrahydro-2H-pyran-2-yl)-N-(2-cyclobutyl-1,5-dimethyl-3-oxo-2,3-dihydro-1H-pyrazol-4-yl)-4-methylisoxazole-3-carboxamide or 5-((2S,6R)-6-(tert-Butyl)tetrahydro-2H-pyran-2-yl)-N-(2-cyclobutyl-1,5-dimethyl-3-oxo-2,3-dihydro-1H-pyrazol-4-yl)-4-methylisoxazole-3-carboxamide Chiral SFC: Rt=18.40 mins
LC-MS: Rt=4.58 mins; MS m/z [M+H]+431.5; Method 8minLowpHv01

1H NMR (400 MHz, CDCl₃) δ 8.28 (1H, brs), 4.69-4.59 (2H, mults), 3.32 (3H, s), 3.10 (1H, d), 2.83 (2H, mults), 2.41-2.34 (2H, mults), 2.29 (3H, s), 2.23 (3H, s), 2.03 (1H, br d), 1.96-1.60 (6H, mults), 1.45-1.33 (1H, mults), 0.93 (9H, s).

Example 16

5-((2S,6R)-6-(tert-butyl)tetrahydro-2H-pyran-2-yl)-N-(2-cyclohexyl-1,5-dimethyl-3-oxo-2,3-dihydro-1H-pyrazol-4-yl)-4-methylisoxazole-3-carboxamide or 5-((2R,6S)-6-(tert-butyl)tetrahydro-2H-pyran-2-yl)-N-(2-cyclohexyl-1,5-dimethyl-3-oxo-2,3-dihydro-1H-pyrazol-4-yl)-4-methylisoxazole-3-carboxamide

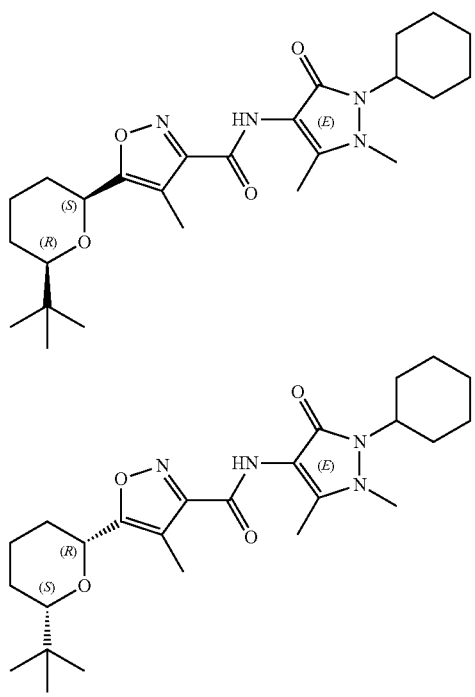

The title compound was prepared by a method similar to that of Example 15 by replacing 4-amino-2-cyclobutyl-1,5-dimethyl-1H-pyrazol-3(2H)-one (Intermediate E) in Step 4 with 4-amino-2-cyclohexyl-1,5-dimethyl-1H-pyrazol-3(2H)-one (Intermediate D). Chiral separation using Supercritical Fluid Chromatography afforded an individual enantiomer:
Method Details:
Column: Chiralpak OD-H 250×10 mm, 5 μm @35 deg C.
Mobile phase: sc-CO₂:Isopropanol+0.1% DEA
Flow: 10 mL/min
Detection: UV @220 nm
Instrument: Berger Minigram SFC1

5-((2S,6R)-6-(tert-butyl)tetrahydro-2H-pyran-2-yl)-N-(2-cyclohexyl-1,5-dimethyl-3-oxo-2,3-dihydro-1H-pyrazol-4-yl)-4-methylisoxazole-3-carboxamide or 5-((2R,6S)-6-(tert-butyl)tetrahydro-2H-pyran-2-yl)-N-(2-cyclohexyl-1,5-dimethyl-3-oxo-2,3-dihydro-1H-pyrazol-4-yl)-4-methylisoxazole-3-carboxamide Chiral SFC Rt=8.19 mins;
LC-MS: Rt=4.87 mins; MS m/z [M+H]+459.5; Method 8minLowpHv01

1H NMR (400 MHz, CDCl₃) δ 7.99 (1H, s), 4.53 (1H, dd), 3.97 (1H, tt), 3.18 (3H, s), 3.01 (1H, dd), 2.20 (3H, s), 2.12 (3H, s), 1.96-1.86 (2H, mults), 1.83-1.74 (4H, mults), 1.72-1.49 (6H, mults), 1.35-1.22 (2H, mults), 1.21-1.11 (2H, mults), 0.84 (9H, s).

Example 17

A mixture of 5-((2R,6S)-6-(tert-butyl)tetrahydro-2H-pyran-2-yl)-N-(2-isopropyl-1,5-dimethyl-3-oxo-2,3-dihydro-1H-pyrazol-4-yl)-4-methylisoxazole-3-carboxamide and 5-((2S,6R)-6-(tert-butyl)tetrahydro-2H-pyran-2-yl)-N-(2-isopropyl-1,5-dimethyl-3-oxo-2,3-dihydro-1H-pyrazol-4-yl)-4-methylisoxazole-3-carboxamide

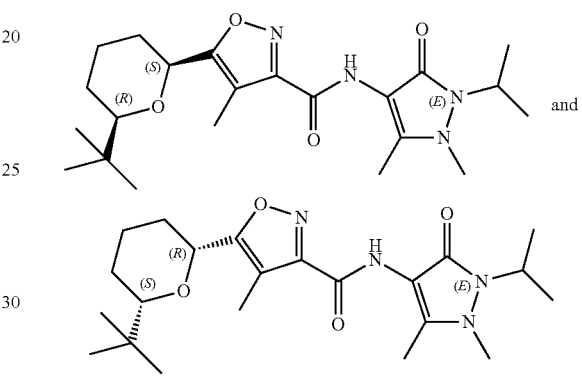

Step 1: A mixture of ethyl 5-((2R,6S)-6-(tert-butyl)-4-iodotetrahydro-2H-pyran-2-yl)-4-methylisoxazole-3-carboxylate and ethyl 5-((2S,6R)-6-(tert-butyl)-4-iodotetrahydro-2H-pyran-2-yl)-4-methylisoxazole-3-carboxylate (1:1)

To a stirred solution of ethyl 5-formyl-4-methylisoxazole-3-carboxylate (1 g, 5.46 mmol), 2,2-dimethylhex-5-en-3-ol (Intermediate F) (0.700 g, 5.46 mmol) and sodium iodide (0.818 g, 5.46 mmol) in dry MeCN (20 mL) under nitrogen at room temperature was added TMSCl (0.698 mL, 5.46 mmol) dropwise over 10 seconds. The reaction mixture was stirred at room temperature overnight. To the resulting mixture was added pivalaldehyde (0.593 mL, 5.46 mmol) and the reaction mixture was stirred for 3 hours. The resulting mixture was diluted with EtOAc and washed with a 10% sodium thiosulfate (aq) solution (×1) and water (×1). The organic layer was dried over MgSO₄, filtered and the solvent removed under reduced pressure. The crude material was then adsorbed onto silica and purification by chromatography eluting with 0-50% EtOAc in iso-hexane afforded the title compounds;
LC-MS: Rt=1.76 mins; MS m/z [M+H]+422.3; Method 2minLowpHv03

Step 2: A mixture of ethyl 5-((2R,6S)-6-(tert-butyl)-5,6-dihydro-2H-pyran-2-yl)-4-methylisoxazole-3-carboxylate and ethyl 5-((2S,6R)-6-(tert-butyl)-5,6-dihydro-2H-pyran-2-yl)-4-methylisoxazole-3-carboxylate (1:1)

To a solution of a mixture of ethyl 5-((2R,6S)-6-(tert-butyl)-4-iodotetrahydro-2H-pyran-2-yl)-4-methylisoxazole-3- carboxylate and ethyl 5-((2S,6R)-6-(tert-butyl)-4-iodotetrahydro-2H-pyran-2-yl)-4-methylisoxazole-3-carboxylate (1:1) (794 mg, 1.885 mmol) in toluene (3.8 mL) was added DBU (0.284 ml, 1.885 mmol) and this was stirred at room temperature overnight. To the resulting mixture was added DBU (0.142 ml, 0.94 mmol) and this was stirred at room temperature for 4 hours. The resulting mixture was diluted with EtOAc and water and the layers were separated. The aqueous layer was extracted with EtOAc. The combined organic extracts were dried over MgSO$_4$, filtered and the solvent removed under reduced pressure. The crude material was then adsorbed onto silica and purification by chromatography eluting with 0-20% EtOAc in iso-hexane afforded the title compounds;

LC-MS: Rt=1.64 mins; MS m/z [M+H]+294.5; Method 2minLowpHv03

Step 3: A mixture of ethyl 5-((2R,6S)-6-(tert-butyl)tetrahydro-2H-pyran-2-yl)-4-methylisoxazole-3-carboxylate and ethyl 5-((2S,6R)-6-(tert-butyl)tetrahydro-2H-pyran-2-yl)-4-methylisoxazole-3-carboxylate To a solution of a mixture of ethyl 5-((2R,6S)-6-(tert-butyl)-5,6-dihydro-2H-pyran-2-yl)-4-methylisoxazole-3-carboxylate and ethyl 5-((2S,6R)-6-(tert-butyl)-5,6-dihydro-2H-pyran-2-yl)-4-methylisoxazole-3-carboxylate (1:1) (212 mg, 0.723 mmol) in Ethanol (14.5 mL) under nitrogen was added 10% Pd/C (769 mg, 0.723 mmol). The reaction mixture was stirred under an atmosphere of hydrogen at room temperature overnight. The resulting mixture was filtered through a Celite® cartridge under nitrogen, eluting with EtOAc. The organic solvent was removed under reduced pressure. The crude material was adsorbed onto silica and purification by chromatography eluting with 0-100% EtOAc in iso-hexane afforded the title compounds;

LC-MS: Rt=1.70 mins; MS m/z [M+H]+296.4; Method 2minLowpHv03

Step 4: 5-((2R,6S)-6-(tert-butyl)tetrahydro-2H-pyran-2-yl)-4-methylisoxazole-3-carboxylic acid and 5-((2S,6R)-6-(tert-butyl)tetrahydro-2H-pyran-2-yl)-4-methylisoxazole-3-carboxylic acid (1:1)

To a solution of a mixture of ethyl 5-((2R,6S)-6-(tert-butyl)tetrahydro-2H-pyran-2-yl)-4-methylisoxazole-3-carboxylate and ethyl 5-((2S,6R)-6-(tert-butyl)tetrahydro-2H-pyran-2-yl)-4-methylisoxazole-3-carboxylate (100 mg, 0.339 mmol) in THF (3 mL) and MeOH (1.8 mL) was added 2M NaOH (aq) (0.186 mL, 0.372 mmol). The reaction mixture was stirred at room temperature overnight. The resulting mixture was concentrated under reduced pressure and the residue diluted with EtOAc and water. The organic layer was extracted with 0.1M NaOH (aq). The combined aqueous layers were acidified with 1M HCl (aq) and extracted with EtOAc (×3). The combined organic extracts were dried over MgSO$_4$ and filtered. The solvent was removed under reduced pressure to afford the title compounds;

LC-MS: Rt=1.52 mins; MS m/z [M+H]+268.4; Method 2minLowpHv03

Step 5: A mixture of 5-((2R,6S)-6-(tert-butyl)tetrahydro-2H-pyran-2-yl)-N-(2-isopropyl-1,5-dimethyl-3-oxo-2,3-dihydro-1H-pyrazol-4-yl)-4-methylisoxazole-3-carboxamide and 5-((2S,6R)-6-(tert-butyl)tetrahydro-2H-pyran-2-yl)-N-(2-isopropyl-1,5-dimethyl-3-oxo-2,3-dihydro-1H-pyrazol-4-yl)-4-methylisoxazole-3-carboxamide (1:1)

To a solution of a mixture of 5-((2R,6S)-6-(tert-butyl)tetrahydro-2H-pyran-2-yl)-4-methylisoxazole-3-carboxylic acid and 5-((2S,6R)-6-(tert-butyl)tetrahydro-2H-pyran-2-yl)-4-methylisoxazole-3-carboxylic acid (1:1) (77 mg, 0.288 mmol) in DCM (2 mL) under nitrogen was added oxalyl chloride (0.026 mL, 0.302 mmol) and DMF (2.230 µl, 0.029 mmol). 4-Amino-2-isopropyl-1,5-dimethyl-1H-pyrazol-3 (2H)-one (Intermediate G) (48.7 mg, 0.288 mmol) and triethylamine (0.161 mL, 1.152 mmol) were added and the reaction mixture was stirred at room temperature overnight. To the resulting mixture was added 1M NaOH and DCM and the mixture was passed through a phase separating column. The organic layer was dried over MgSO$_4$, filtered and the solvent removed under reduced pressure. The crude material was then adsorbed onto silica and purification by chromatography eluting with 0-100% EtOAc in iso-hexane afforded the title compounds;

LC-MS: Rt=4.50 mins; MS m/z [M+H]+419.5; Method 8minLowpHv01

$^1$H NMR (400 MHz, DMSO-d6) δ 9.50 (1H, s), 4.72 (1H, mult), 4.36 (1H, mult), 3.22 (3H, s), 3.16 (1H, d), 2.14 (3H, s), 2.04 (3H, s), 1.99-1.90 (1H, mult), 1.84-1.78 (1H, mult), 1.70-1.59 (3H, br mult), 1.35 (6H, d), 1.38-1.23 (1H, br mult), 0.88 (9H, s).

Example 18

A mixture of N-(2-cyclohexyl-1,5-dimethyl-3-oxo-2,3-dihydro-1H-pyrazol-4-yl)-5-((2R,6R)-6-isopropyl-3,6-dihydro-2H-pyran-2-yl)-4-methylisoxazole-3-carboxamide and N-(2-cyclohexyl-1,5-dimethyl-3-oxo-2,3-dihydro-1H-pyrazol-4-yl)-5-((2R,6S)-6-isopropyl-5,6-dihydro-2H-pyran-2-yl)-4-methylisoxazole-3-carboxamide and N-(2-cyclohexyl-1,5-dimethyl-3-oxo-2,3-dihydro-1H-pyrazol-4-yl)-5-((2S,6R)-6-isopropyl-5,6-dihydro-2H-pyran-2-yl)-4-methylisoxazole-3-carboxamide and N-(2-cyclohexyl-1,5-dimethyl-3-oxo-2,3-dihydro-1H-pyrazol-4-yl)-5-((2S,6S)-6-isopropyl-3,6-dihydro-2H-pyran-2-yl)-4-methylisoxazole-3-carboxamide

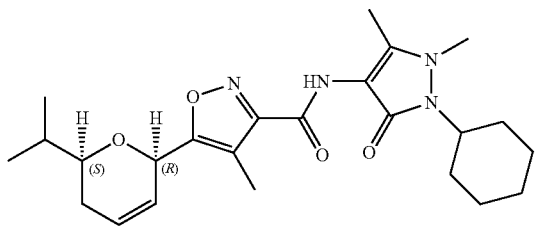

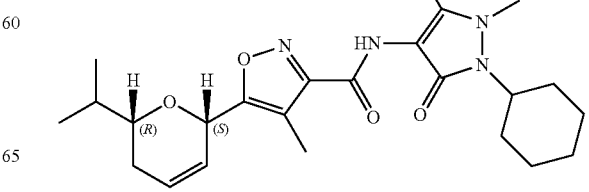

-continued

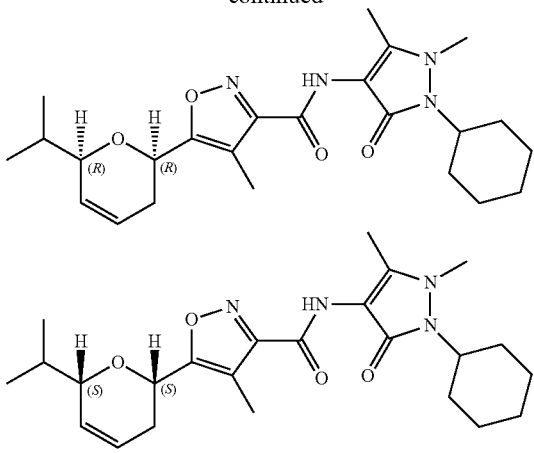

Step 1: Ethyl 4-methyl-5-vinylisoxazole-3-carboxylate

The title compound was prepared analogously to Intermediate C, Step 1.

$^1$H NMR (400 MHz, DMSO-d6) δ 6.86 (1H, dd), 6.02 (1H, d), 5.69 (1H, d), 4.37 (2H, q), 2.19 (3H, s), 1.33 (3H, t).

Step 2: 4-Methyl-5-vinylisoxazole-3-carboxylic acid

Ethyl 4-methyl-5-vinylisoxazole-3-carboxylate (250 mg, 0.993 mmol) was dissolved in THF (5.3 mL) and MeOH (3.2 mL) and to this was added 2M NaOH (aq) (497 μl, 0.993 mmol). The reaction mixture was stirred at room temperature for 15 minutes. The resulting mixture was concentrated under reduced pressure and treated with 2M HCl (5 mL) and water (5 mL). DCM was added to the aqueous resulting in the formation of an emulsion. The solvent was removed under reduced pressure. The resulting residue was suspended in DCM (25 mL) and passed through a phase separating column. The organic solvent was removed under reduced pressure to afford the title compound;

LC-MS: Rt=1.04 mins: MS m/z [M+H]+154.1: Method 2minLowpHv03

Step 3: N-(2-Cyclohexyl-1,5-dimethyl-3-oxo-2,3-dihydro-1H-pyrazol-4-yl)-4-methyl-5-vinylisoxazole-3-carboxamide A suspension of 4-methyl-5-vinylisoxazole-3-carboxylic acid (172 mg, 0.809 mmol) in DCM (10 mL) cooled to 0° C. was treated with oxalyl chloride (0.142 mL, 1.617 mmol) and DMF (4 drops). The reaction mixture was stirred at 0° C. for 1 hour and at room temperature for 30 minutes. The solvent was removed under reduced pressure and the residue dissolved in DCM (8 mL). 4-Amino-2-cyclohexyl-1,5-dimethyl-1H-pyrazol-3(2H)-one (169 mg, 0.809 mmol) (Intermediate D) and triethylamine (0.338 mL, 2.426 mmol) were added. The reaction mixture was stirred at room temperature overnight. The resulting mixture was diluted with water (15 mL) and extracted with DCM (×2). The organic extracts were combined and the solvent removed under reduced pressure. The crude material was adsorbed onto silica and purification by chromatography eluting with 20-100% EtOAc in iso-hexane afforded the title compound;

LC-MS: Rt 1.11 mins: MS m/z [M+H]+345.4: Method 2minLowpHv03

Step 4: N-(2-Cyclohexyl-1,5-dimethyl-3-oxo-2,3-dihydro-1H-pyrazol-4-yl)-5-formyl-4-methylisoxazole-3-carboxamide To a solution of N-(2-Cyclohexyl-1,5-dimethyl-3-oxo-2,3-dihydro-1H-pyrazol-4-yl)-4-methyl-5-vinylisoxazole-3-carboxamide (53 mg, 0.154 mmol) in THF (1 mL) and water (0.5 mL) was added sodium periodate (99 mg, 0.462 mmol) and Os EnCat™ (Microencapsulated OsO$_4$) (10.26 mg, 3.08 μmol). The reaction mixture was stirred at room temperature overnight. The resulting mixture was filtered through a cotton wool plug and the eluent was concentrated under reduced pressure to afford the title compound;

$^1$H NMR (400 MHz, CDCl$_3$) δ 10.09 (1H, s), 8.34 (1H, br s), 4.07 (1H, mult), 3.32 (3H, s), 2.57 (3H, s), 2.23 (3H, s), 2.08-1.95 (2H, br mults), 1.94-1.80 (4H, br mults), 1.71 (1H, br mult), 1.44-1.30 (2H, br mults), 1.30-1.16 (1H, br mult).

Step 5: N-(2-Cyclohexyl-1,5-dimethyl-3-oxo-2,3-dihydro-1H-pyrazol-4-yl)-5-(1-hydroxybut-3-en-1-yl)-4-methylisoxazole-3-carboxamide A solution of N-(2-cyclohexyl-1,5-dimethyl-3-oxo-2,3-dihydro-1H-pyrazol-4-yl)-5-formyl-4-methylisoxazole-3-carboxamide (53 mg, 0.153 mmol) in THF (1.5 mL) was cooled to 0° C. and 1M allylmagnesium bromide in Et$_2$O (337 μl, 0.337 mmol) was added dropwise over 15 mins. The reaction mixture was warmed to room temperature and saturated NH$_4$Cl (aq) was added. The aqueous layer was extracted with DCM (×3). The combined organic extracts were passed through a phase separating cartridge and the organic solvent was removed under reduced pressure. The crude material was adsorbed onto silica and purification by chromatography eluting with 50-100% EtOAc in iso-hexane afforded the title compound.

Step 6: A mixture of N-(2-cyclohexyl-1,5-dimethyl-3-oxo-2,3-dihydro-1H-pyrazol-4-yl)-5-((2R,6R)-6-isopropyl-3,6-dihydro-2H-pyran-2-yl)-4-methylisoxazole-3-carboxamide and N-(2-cyclohexyl-1,5-dimethyl-3-oxo-2,3-dihydro-1H-pyrazol-4-yl)-5-((2R,6S)-6-isopropyl-5,6-dihydro-2H-pyran-2-yl)-4-methylisoxazole-3-carboxamide and N-(2-cyclohexyl-1,5-dimethyl-3-oxo-2,3-dihydro-1H-pyrazol-4-yl)-5-((2S,6R)-6-isopropyl-5,6-dihydro-2H-pyran-2-yl)-4-methylisoxazole-3-carboxamide and N-(2-cyclohexyl-1,5-dimethyl-3-oxo-2,3-dihydro-1H-pyrazol-4-yl)-5-((2S,6S)-6-isopropyl-3,6-dihydro-2H-pyran-2-yl)-4-methylisoxazole-3-carboxamide A solution of N-(2-cyclohexyl-1,5-dimethyl-3-oxo-2,3-dihydro-1H-pyrazol-4-yl)-5-(1-hydroxybut-3-en-1-yl)-4-methylisoxazole-3-carboxamide (26 mg, 0.054 mmol) in DCM (0.5 mL) was cooled to 0° C. and isobutyraldehyde (5.38 μl, 0.059 mmol) and TMSOTf (10.66 μl, 0.059 mmol) were added. The reaction mixture was stirred at 0° C. for 1 hour and at room temperature overnight. To the resulting mixture was added a saturated NH$_4$Cl (aq) solution and this was extracted with DCM (×3). The combined organic extracts were passed through a phase separating cartridge and the organic solvent was removed under reduced pressure. The crude material was dissolved in DMSO and purified using UV-directed automated reverse phase chromatography over a 9.5 minute gradient of 30-70% MeCN in water (0.1% formic acid) using an Xselect CSH Prep C18 column to afford the title compounds as a mixture of alkenes, proposed ratio of products by NMR is 3:2 4-ene:3-ene; proposed stereochemistry is syn.

LC-MS: Rt=1.40 mins; MS m/z [M+H]+443.3: Method 2minLowpHv03

$^1$H NMR (400 MHz, CDCl$_3$) δ 8.13-8.07 (m, 2H), 6.08-6.03 (m, 1H), 5.936-5.92 (m, 1H), 5.80-5.73 (m, 2H), 5.46-5.42 (m, 1H), 4.85 (dd, J=10.37, 3.3, 1H), 4.18-4.14 (m, 1H), 4.10-4.04 (m, 3H), 3.43-3.40 (m, 1H), 3.32-3.24 (m, 7H), 2.30 (s, 3H), 2.27 (s, 3H), 2.24-2.21 (m, 8H), 2.02-1.50 (m, 16H), 1.44-1.06 (m, 8H), 1.01-0.94 (m, 12H).

Example 19

A mixture of N-(2-cyclohexyl-1,5-dimethyl-3-oxo-2,3-dihydro-1H-pyrazol-4-yl)-4-methyl-5-((2S,6S)-6-methyl-3,6-dihydro-2H-pyran-2-yl)isoxazole-3-carboxamide and N-(2-cyclohexyl-1,5-dimethyl-3-oxo-2,3-dihydro-1H-pyrazol-4-yl)-4-methyl-5-((2R,6R)-6-methyl-3,6-dihydro-2H-pyran-2-yl)isoxazole-3-carboxamide

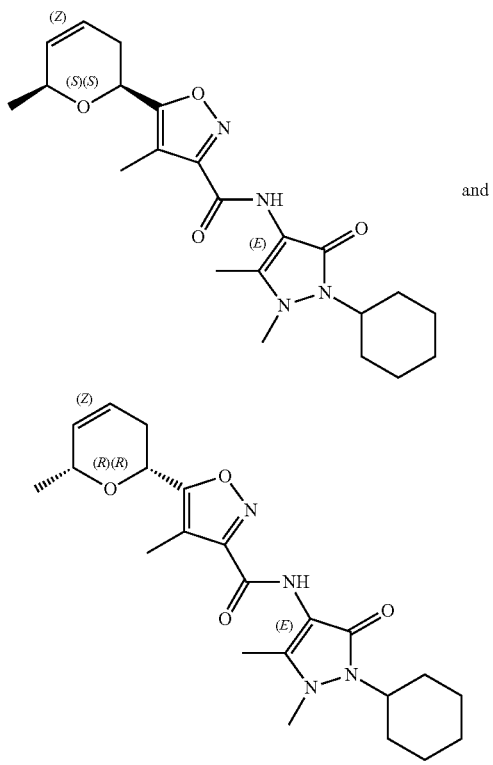

Step 1: Ethyl 5-(1-hydroxybut-3-en-1-yl)-4-methylisoxazole-3-carboxylate

A solution of boron trifluoride diethyletherate (54.1 µl, 0.427 mmoL) in DCM (0.3 mL) was cooled to −78° C. In a separate flask a solution of ethyl 5-formyl-4-methylisoxazole-3-carboxylate (Intermediate C) (68 mg, 0.371 mmol) and allyltrimethylsilane (59.0 µl, 0.371 mmol) in DCM were cooled to −78° C. and this solution was added dropwise to the boron trifluoride diethyletherate solution. The reaction mixture was stirred at −78° C. for 1 hour and at room temperature overnight. To the resulting mixture was added a saturated solution of NaHCO$_3$ (aq) (5 mL) and this was extracted with DCM (×3). The combined organic extracts were passed through a phase separating cartridge and the eluent was concentrated under reduced pressure. The crude material was adsorbed onto silica and purification by chromatography eluting with 0-50% EtOAc in iso-hexane afforded the title compound;

LC-MS: Rt=1.07 mins; MS m/z [M+H]+226.1: Method 2minLowpHv03

Step 2: Ethyl 4-methyl-5-(6-methyl-3,6-dihydro-2H-pyran-2-yl)isoxazole-3-carboxylate A solution of ethyl 5-(1-hydroxybut-3-en-1-yl)-4-methyl-isoxazole-3-carboxylate (35 mg, 0.155 mmol) in DCM (1 mL) was treated with acetaldehyde (8.72 µl, 0.155 mmol) and the reaction mixture was cooled to 0° C. A solution of TMSOTf (80.4 µL, 0.465 mmol) in DCM (1.5 mL) cooled to 0° C. was added and the reaction mixture was stirred at 0° C. for 30 minutes and at room temperature overnight. To the resulting mixture was added a saturated solution of ammonium chloride (aq) (2 mL) and this was extracted with DCM (×3). The combined organic extracts were passed through a phase separating cartridge and the eluent was concentrated under reduced pressure. The crude material was adsorbed onto silica and purification by chromatography eluting with 0-100% EtOAc in iso-hexane afforded the title compound;

LC-MS: Rt=1.32 mins: MS m/z [M+H]+252.2: Method 2minLowpHv03

Step 3: 4-Methyl-5-(6-methyl-3,6-dihydro-2H-pyran-2-yl)isoxazole-3-carboxylic acid To a solution of ethyl 4-methyl-5-(6-methyl-3,6-dihydro-2H-pyran-2-yl)isoxazole-3-carboxylate (14 mg, 0.056 mmol) in MeOH (0.2 mL) and THF (0.3 mL) was added 2M NaOH (aq) (27.9 µl, 0.056 mmol). The reaction mixture was stirred at room temperature for 3 hours. The resulting mixture was concentrated under reduced pressure and 2M NaOH (aq) (1 mL) and water (1 mL) added. The aqueous was extracted with DCM (×3) and the combined organic extracts passed through a phase separating cartridge. The eluent was concentrated under reduced pressure to afford the title compound.

Step 4: Racemic mixture of N-(2-cyclohexyl-1,5-dimethyl-3-oxo-2,3-dihydro-1H-pyrazol-4-yl)-4-methyl-5-((2S,6S)-6-methyl-3,6-dihydro-2H-pyran-2-yl)isoxazole-3-carboxamide and N-(2-cyclohexyl-1,5-dimethyl-3-oxo-2,3-dihydro-1H-pyrazol-4-yl)-4-methyl-5-((2R,6R)-6-methyl-3,6-dihydro-2H-pyran-2-yl)isoxazole-3-carboxamide A solution of 4-methyl-5-(6-methyl-3,6-dihydro-2H-pyran-2-yl)isoxazole-3-carboxylic acid) (12.03 mg, 0.054 mmoL) in NMP (0.5 mL) was added HATU (20.49 mg, 0.054 mmol). 4-Amino-2-cyclohexyl-1,5-dimethyl-1H-pyrazol-3(2H)-one (Intermediate D) (11.28 mg, 0.054 mmol) and triethylamine (7.49 µl, 0.054 mmoL) were added and the reaction mixture was stirred at room temperature overnight. The resulting mixture was partitioned between saturated aqueous sodium hydrogen carbonate (10 mL) and EtOAc (10 mL). The organics were washed with brine (10 mL), dried over MgSO$_4$, filtered and the solvent removed under reduced pressure. The crude material was adsorbed onto silica and purification by chromatography eluting with 40-100% EtOAc in iso-hexane afforded the title compound;

LC-MS: Rt=3.65 mins: MS m/z [M+H]+415.3: Method 8minLowpHv01

$^1$H NMR (400 MHz, CDCl$_3$) δ 7.98 (s, 1H), 5.86-5.77 (m, 1H), 5.68-5.60 (m, 1H), 4.77 (dd, J=10.9, 3.3 Hz, 1H), 4.37 (s, 1H), 4.04-3.93 (m, 1H), 3.31 (t, J=7.0 Hz, 1H), 3.26 (s, 3H), 2.67-2.54 (m, 1H), 2.31 (t, J=8.1 Hz, 1H), 2.19-2.08 (m, 7H), 2.02-1.87 (m, 2H), 1.86-1.72 (m, 2H), 1.64-1.59 (m, 1H), 1.36-1.05 (m, 7H).

Example 20

N-(2-Cyclohexyl-1,5-dimethyl-3-oxo-2,3-dihydro-1H-pyrazol-4-yl)-4-methyl-5-((2R,3S)-3,5,5-trimethyl-1,4-dioxan-2-yl)isoxazole-3-carboxamide

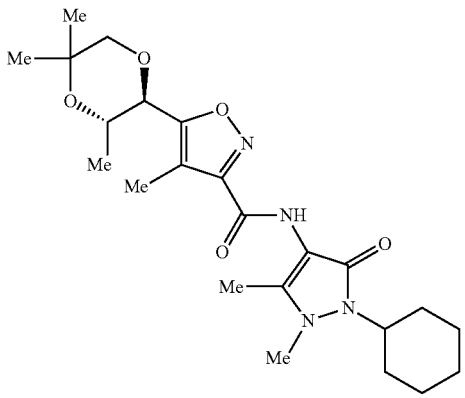 [SMILES: Cc1c(C(=O)Nc2c(C)n(C)n(C3CCCCC3)c2=O)noc1[C@@H]1OCC(C)(C)O[C@H]1C]

Step 1: Ethyl 5-((1R,2S)-2-((tert-butyldimethylsilyl)oxy)-1-hydroxypropyl)-4-methylisoxazole-3-carboxylate tertbutyldimethylsilyl chloride (6.3 g, 41.5 mmol) was added portionwise to ethyl 5-((1R,2S)-1,2-dihydroxypropyl)-4-methylisoxazole-3-carboxylate (Intermediate B)(8.65 g, 37.7 mmol), 4-dimethylaminopyridine (1.38 g, 11.32 mmol) and triethylamine (5.80 mL,) in DMF (100 mL) at 0° C. and the reaction was allowed to warm to room temperature. After 18 h the reaction was partitioned between EtOAc and brine, washed with saturated aqueous ammonium chloride, brine, dried over Na$_2$SO$_4$ and concentrated under reduced pressure. The crude material was adsorbed onto silica and purification by chromatography eluting with 15% EtOAc in iso-hexane afforded the title compound;

LC-MS: Rt=1.59 mins; MS m/z [M+H]+344.4; Method 2minLowpHv03

Step 2: ethyl 5-((1R,2S)-2-((tert-butyldimethylsilyl)oxy)-1-((2-methylallyl)oxy)propyl)-4-methylisoxazole-3-carboxylate and 2-methylallyl 5-((1R,2S)-2-((tert-butyldimethylsilyl)oxy)-1-((2-methylallyl)oxy)propyl)-4-methylisoxazole-3-carboxylate NaH (700 mg of a 60 wt % dispersion in mineral oil, 17.47 mmol) was added portionwise to ethyl 5-((1R,2S)-2-((tert-butyldimethylsilyl)oxy)-1-hydroxypropyl)-4-methylisoxazole-3-carboxylate (3.0 g, 8.73 mmol) in THF (75 mL) at room temperature, followed by 3-bromo-2-methylprop-1-ene (8.81 ml, 87 mmol) dropwise over 10 minutes. Tetrabutyl ammonium iodide (2.58 g, 6.99 mmol) was added and the resulting reaction was heated at 58° C. for 2 hours. The reaction was cooled to room temperature and quenched sequentially with brine (75 mL) and EtOAc (75 mL), dried over Na$_2$SO$_4$ and concentrated under reduced pressure to afford the crude title compounds as an approximate 9:1 mixture;

LC-MS: Rt=1.90 mins; MS m/z [M+H]+398.5; Method 2minLowpHv03

LC-MS: Rt=1.95 mins; MS m/z [M+H]+424.5; Method 2minLowpHv03

Step 3: 5-((1R,2S)-2-((tert-Butyldimethylsilyl)oxy)-1-((2-methylallyl)oxy)propyl)-4-methylisoxazole-3-carboxylic acid Lithium Hydroxide monohydrate (3.20 g, 76 mmol) was added portionwise to a mixture of ethyl 5-((1R,2S)-2-((tert-butyldimethyl silyl)oxy)-1-((2-methylallyl)oxy)propyl)-4-methylisoxazole-3-carboxylate and 2-methylallyl 5-((1R,2S)-2-((tert-butyldimethylsilyl)oxy)-1-((2-methylallyl)oxy)propyl)-4-methylisoxazole-3-carboxylate [4.5 g as an approximate 9:1 mixture containing residual Tetrabutyl ammonium iodide (25% w/w)] in THF/water (300 mL, 1.5/1.0) and the resulting mixture was heated gently at 70° C. After cooling to room temperature the layers were separated and the remaining aqueous was acidified with 1 M aqueous hydrochloric acid and extracted with EtOAc. The organic extracts were combined and washed with brine, dried over Na$_2$SO$_4$ and concentrated under reduced pressure to afford the crude title compound;

LC-MS: Rt=1.75 mins; MS m/z [M+H]+370.5; Method 2minLowpHv03

Step 4: 5-((1R,2S)-2-((tert-Butyldimethylsilyl)oxy)-1-((2-methylallyl)oxy)propyl)-N-(2-cyclohexyl-1,5-dimethyl-3-oxo-2,3-dihydro-1H-pyrazol-4-yl)-4-methylisoxazole-3-carboxamide 4-Amino-2-cyclohexyl-1,5-dimethyl-1H-pyrazol-3(2H)-one (Intermediate D) (2.63 g, 12.55 mmol) was added portionwise to 5-((1R,2S)-2-((tert-butyldimethylsilyl)oxy)-1-((2-methylallyl)oxy)propyl)-4-methylisoxazole-3-carboxylic acid (4.14 g, ~70% w/w) in DMF (100 mL) followed by DIPEA (7.8 ml, 44.8 mmol) and HATU (4.8 g, 12.55 mmol). After stirring at room temperature for 18 h the reaction mixture was partitioned between EtOAc and brine. The aqueous phase was extracted with EtOAc and the combined organic extracts were washed with brine, dried over Na$_2$SO$_4$ and concentrated under reduced pressure. The crude material was adsorbed onto silica and purification by chromatography eluting with 50-100% EtOAc in iso-hexane afforded the title compound;

LC-MS: Rt=1.77 mins; MS m/z [M+H]+561.8; Method 2minLowpHv03

Step 5: N-(2-Cyclohexyl-1,5-dimethyl-3-oxo-2,3-dihydro-1H-pyrazol-4-yl)-5-((1R,2S)-2-hydroxy-1-((2-methylallyl)oxy)propyl)-4-methylisoxazole-3-carboxamide Tetrabutyl ammonium fluoride (15.16 ml, 15.16 mmol) was added dropwise to 5-((1R,2S)-2-((tert-butyldimethylsilyl)oxy)-1-((2-methylallyl)oxy)propyl)-N-(2-cyclohexyl-1,5-dimethyl-3-oxo-2,3-dihydro-1H-pyrazol-4-yl)-4-methyl-isoxazole-3-carboxamide (5.06 g, 7.58 mmol (assuming 76% purity)) in THF (160 ml) and the resulting mixture was stirred at room temperature for 18 h.

The resulting mixture was quenched by the sequential addition of water (150 ml) and EtOAc (200 ml). The organics were washed with brine, dried over Na₂SO₄ and concentrated under reduced pressure. The crude material was adsorbed onto silica and purification by chromatography eluting with 50-100% EtOAc in iso-hexane afforded the title compound;

LC-MS: Rt=1.12 mins; MS m/z [M+H]+447.5; Method 2minLowpHv03

Step 6: N-(2-Cyclohexyl-1,5-dimethyl-3-oxo-2,3-dihydro-1H-pyrazol-4-yl)-4-methyl-5-((2R,3S)-3,5,5-trimethyl-1,4-dioxan-2-yl)isoxazole-3-carboxamide Mercuric trifluoroacetate (3.92 g, 9.19 mmol) was added portionwise to N-(2-cyclohexyl-1,5-dimethyl-3-oxo-2,3-dihydro-1H-pyrazol-4-yl)-5-((1R,2S)-2-hydroxy-1-((2-methylallyl)oxy)propyl)-4-methylisoxazole-3-carboxamide (3.59 g, 8.03 mmol) in THF (160 mL) at room temperature. Mercuric oxide red (1.99 g, 9.19 mmol) was added and the resulting reaction mixture was stirred at room temperature. After 1 h the reaction was cooled to −78° C. and triethylborane (16.84 ml, 16.84 mmol) was added dropwise followed by sodium borohydride (579 mg, 15.31 mmol) portionwise. After 1 h at −78° C. the reaction was allowed to warm gradually to room temperature. The resulting mixture was quenched by the addition of brine and EtOAc, separated, dried over Na₂SO₄ and concentrated under reduced pressure. DCM (200 ml) and Biotage Si-Thiol (17 g, 1.4 mmol/g load, ~3 eq) were added and the resulting suspension was stirred at room temperature for 18 h. The reaction was filtered, washed with DCM and concentrated under reduced pressure. The crude material was adsorbed onto silica and purification by chromatography eluting with 90-95% EtOAc in iso-hexane afforded the title compound (>95% ee);

LC-MS: Rt=1.16 mins; MS m/z [M+H]+447.5; Method 2minLowpHv03

¹H NMR. ([400 MHz], [DMSO] 9.55 (1H, s), 4.36 (1H, d), 4.09 (1H, m), 3.91 (1H, m), 3.65 (1H, d), 3.42 (1H, d), 3.21 (3H, s), 2.16 (3H, s), 2.03 (3H, s), 1.98 (2H, m), 1.78 (2H, m), 1.64 (3H, m), 1.37 (3H, s), 1.31 (2H, m), 1.17 (1H, m), 1.10 (3H, s), 0.87 (3H, d).

Example 21.1

21.1 [5-(4-Bromo-5-methyltetrahydro-2H-pyran-2-yl)-N-(2-cyclohexyl-1,5-dimethyl-3-oxo-2,3-dihydro-1H-pyrazol-4-yl)-4-methylisoxazole-3-carboxamide]

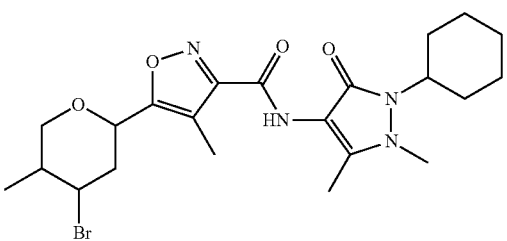 [SMILES: Cc1c(C(=O)Nc2c(C)n(C)n(C3CCCCC3)c2=O)noc1C1CC(Br)C(C)CO1]

and Example 21.2: N-(2-cyclohexyl-1,5-dimethyl-3-oxo-2,3-dihydro-1H-pyrazol-4-yl)-4-methyl-5-(5-methyl-3,6-dihydro-2H-pyran-2-yl)isoxazole-3-carboxamide

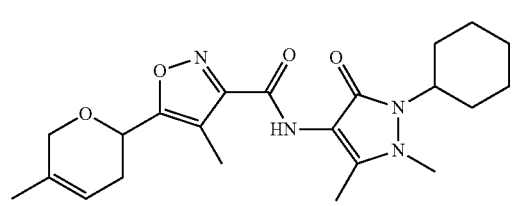 [SMILES: CC1=CCC(c2onc(C(=O)Nc3c(C)n(C)n(C4CCCCC4)c3=O)c2C)OC1]

Step 1: [Ethyl 5-(4-bromo-5-methyltetrahydro-2H-pyran-2-yl)-4-methylisoxazole-3-carboxylate]

To an ice-cooled mixture of 2-methylbut-3-en-1-ol (Aldrich) (0.171 mL, 1.638 mmol), indium (III) bromide (28.3 mg, 0.082 mmol) and dry DCM (10 mL) under nitrogen, was added bromotrimethylsilane (0.213 mL, 1.638 mmol). The reaction mixture was stirred with ice cooling for 30 mins. A solution of ice cold ethyl 5-formyl-4-methylisoxazole-3-carboxylate (Intermediate C) (300 mg, 1.638 mmol) in dry DCM (2 mL) was added to the reaction mixture over a 5 minute period. The reaction mixture was stirred with ice cooling and warmed to room temperature over the weekend. The resulting mixture was treated with saturated aqueous NaHCO₃ (10 ml) with stirring at 0° C. The resulting mixture was passed through a phase separating cartridge and the eluent solvent was removed under reduced pressure. The crude material was dissolved in DMSO and purified using UV-directed automated reverse phase chromatography over a 9.5 minute gradient of 50-98% MeCN in water (0.1% formic acid). The product fractions were added to EtOAc (50 mL) and washed with saturated aqueous NaHCO₃ (50 ml). The organics were dried over MgSO₄, filtered and the solvent removed under reduced pressure to afford the title compound;

LC-MS: Rt=1.47 mins; MS m/z [M+H]+332.2/334.2: Method 2minLowpHv03

Step 2: [Potassium 5-(4-bromo-5-methyltetrahydro-2H-pyran-2-yl)-4-methylisoxazole-3-carboxylate] and potassium (R)-4-methyl-5-(5-methyl-3,6-dihydro-2H-pyran-2-yl)isoxazole-3-carboxylate and potassium (S)-4-methyl-5-(5-methyl-3,6-dihydro-2H-pyran-2-yl)isoxazole-3-carboxylate To a solution of [ethyl 5-(4-bromo-5-methyltetrahydro-2H-pyran-2-yl)-4-methylisoxazole-3-carboxylate] (211 mg, 0.635 mmol) in dry THF (5 mL), potassium trimethylsilanolate (Aldrich) (107 mg, 0.953 mmol) was added. The reaction mixture was stirred at room temperature and sonicated. Further THF was added and the mixture was stirred for 3 hours. The resulting mixture was concentrated under reduced pressure to afford a mixture of the title compounds;

LC-MS: Rt=1.07 mins; MS m/z [M+H]+224.2; Rt=1.20 mins; MS m/z [M+H]+306.2: Method 2minLowpHv03.

Step 3: [5-(4-Bromo-5-methyltetrahydro-2H-pyran-2-yl)-N-(2-cyclohexyl-1,5-dimethyl-3-oxo-2,3-dihydro-1H-pyrazol-4-yl)-4-methylisoxazole-3-carboxamide] and a mixture of (R)—N-(2-cyclohexyl-1,5-dimethyl-3-oxo-2,3-dihydro-1H-pyrazol-4-yl)-4-methyl-5-(5-methyl-3,6-dihydro-2H-pyran-2-yl)isoxazole-3-carboxamide compound and (S)—N-(2-cyclohexyl-1,5-dimethyl-3-oxo-2,3-dihydro-1H-pyrazol-4-yl)-4-methyl-5-(5-methyl-3,6-dihydro-2H-pyran-2-yl)isoxazole-3-carboxamide (1:1)

To a stirred solution of potassium 5-(4-bromo-5-methyltetrahydro-2H-pyran-2-yl)-4-methylisoxazole-3-carboxylate and potassium 4-methyl-5-(5-methyl-3,6-dihydro-2H-pyran-2-yl)isoxazole-3-carboxylate (crude mixture) (217 mg, 0.634 mmol) in dry NMP (4 mL) was added HATU (Fluorochem) (265 mg, 0.697 mmol), 4-amino-2-cyclohexyl-1,5-dimethyl-1H-pyrazol-3(2H)-one (Intermediate D) (133 mg, 0.634 mmol) and triethylamine (0.194 mL, 1.395 mmol). The reaction mixture was stirred at room temperature overnight and partitioned between EtOAc (25 mL) and 1M NaOH (25 mL). The organics were washed with water (30 mL), brine (30 mL), dried over MgSO$_4$, filtered and concentrated under reduced pressure. The crude material was dissolved in DMSO and purified using UV-directed automated reverse phase chromatography over a 9.5 minute gradient of 30-70% MeCN in water (0.1% formic acid). The product fractions were added to EtOAc (50 mL) and washed with saturated aqueous NaHCO$_3$ (50 mL). The organic layers were dried over MgSO$_4$, filtered and the solvent removed under reduced pressure to afford the title compounds.

Example 21.1

[5-(4-bromo-5-methyltetrahydro-2H-pyran-2-yl)-N-(2-cyclohexyl-1,5-dimethyl-3-oxo-2,3-dihydro-1H-pyrazol-4-yl)-4-methylisoxazole-3-carboxamide] LC-MS: Rt=1.30 mins; MS m/z [M+H]+497.5: Method 2minLowpHv03

$^1$H NMR (400 MHz, CDCl$_3$) δ 7.88 (1H, s), 4.47 (1H, mult), 4.03-3.87 (2H, br mults), 3.80-3.72 (1H, mult), 3.14 (3H, s), 2.43-2.36 (1H, br mult), 2.13 (3H, s), 2.08 (3H, s), 2.01 (1H, br mult), 1.91-1.80 (3H, br mults), 1.79-1.68 (5H, br mults), 1.58 (1H, br mult), 1.31-1.18 (2H, br mults), 1.16-1.05 (1H, br mult), 0.95 (3H, d).

Example 21.2

N-(2-cyclohexyl-1,5-dimethyl-3-oxo-2,3-dihydro-1H-pyrazol-4-yl)-4-methyl-5-(5-methyl-3,6-dihydro-2H-pyran-2-yl)isoxazole-3-carboxamide LC-MS: Rt=1.25 mins; MS m/z [M+H]+415.4: Method 2min-LowpHv03

$^1$H NMR (400 MHz, CDCl$_3$) δ 8.04 (1H, s), 5.63 (1H, mult), 4.78 (1H, dd), 4.26-4.00 (3H, br mults), 3.26 (3H, s), 2.72-2.61 (1H, br mult), 2.28 (3H, s), 2.21 (3H, s), 2.07-1.93 (3H, br mults), 1.92-1.81 (5H, br mults), 1.75-1.66 (2H, br mults), 1.67 (3H, s), 1.44-1.30 (2H, br mults), 1.30-1.18 (1H, br mult).

Example 22

N-(2-cyclohexyl-1,5-dimethyl-3-oxo-2,3-dihydro-1H-pyrazol-4-yl)-4-methyl-5-((2R,5R)-5-methyltetrahydro-2H-pyran-2-yl)isoxazole-3-carboxamide

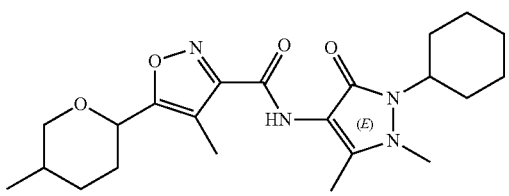 [SMILES: Cc1c(C(=O)Nc2c(C)n(C)n(C3CCCCC3)c2=O)noc1C1CCC(C)CO1]

To a mixture of (R)—N-(2-cyclohexyl-1,5-dimethyl-3-oxo-2,3-dihydro-1H-pyrazol-4-yl)-4-methyl-5-(5-methyl-3,6-dihydro-2H-pyran-2-yl)isoxazole-3-carboxamide compound and (S)—N-(2-cyclohexyl-1,5-dimethyl-3-oxo-2,3-dihydro-1H-pyrazol-4-yl)-4-methyl-5-(5-methyl-3,6-dihydro-2H-pyran-2-yl)isoxazole-3-carboxamide (1:1) (Example 21.2) (35 mg, 0.084 mmol) in EtOH (15 mL) under a flow of nitrogen was added Pd—C (3.59 mg, 0.034 mmol). The reaction mixture was stirred at room temperature under an atmosphere of hydrogen at 0.35 bar for 2 hours. The resulting mixture was filtered through Celite®, washing with Ethanol. The filtrate was concentrated under reduced pressure and passed through a 1 g Biotage Silica-TMT cartridge under gravity. The cartridge was washed with ethanol and the eluent was concentrated under reduced pressure. The crude material was dissolved in DMSO and purified using UV-directed automated reverse phase chromatography over a 9.5 minute gradient of 30-70% MeCN in water (0.1% formic acid). The product fractions were added to EtOAc (30 mL) and washed with saturated aqueous NaHCO$_3$ (30 mL). The organic extracts were dried over MgSO$_4$, filtered and concentrated under reduced pressure to afford the title compound;

LC-MS: Rt 1.23 mins; MS m/z [M+H]+417.4; Method 2minLowpHv03

$^1$H NMR (400 MHz, CDCl$_3$) δ 8.35 (1H, mult), 4.77 (1H, mult), 4.17-3.99 (2H, mults), 3.72 (1H, dd), 3.50 (1H, dd), 3.34 (3H, mult), 2.29-2.22 (6H, mults), 2.08-1.97 (4H, mults), 1.86 (3H, mults), 1.75 (1H, mult), 1.63 (1H mult), 1.37 (2H, mult), 1.30-1.22 (3H, mult), 1.05 (2H, mult), 0.87 (1H, mult).

Chiral separation of Example 22 using Supercritical Fluid Chromatography afforded two individual enantiomer of the cis diastereomer and a racemic mixture of the trans diastereomer:

Method Details:

Column: Chiralpak AD-H 250×10 mm, 5 um @35 deg C.

Mobile phase: 30% Methanol/70% CO2

Flow: 10 ml/min

Detection: UV @220 nm

Instrument: Berger Minigram SFC2

Example 22.a

Single stereoisomer of N-(2-cyclohexyl-1,5-dimethyl-3-oxo-2,3-dihydro-1H-pyrazol-4-yl)-4-methyl-5-(5-methyltetrahydro-2H-pyran-2-yl)isoxazole-3-carboxamide

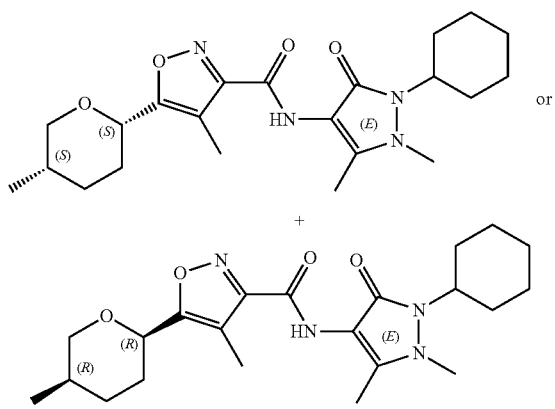

SFC retention time=9.74 mins $^1$H NMR (400 MHz, CDCl$_3$) δ 8.04 (1H, br s), 4.80-4.75 (1H, br mult), 4.05 (1H, tt), 3.76-3.70 (1H, dd), 3.55-3.48 (1H, dd), 3.25 (3H, s), 2.28 (3H, s), 2.21 (3H, s), 2.07-1.93 (2H, br mults), 1.93-1.75 (8H, br mults), 1.71 (1H, br mult), 1.67-1.58 (1H, br mult), 1.44-1.30 (2H, br mults), 1.30-1.18 (1H, br mult), 1.05 (3H, d).

Example 22.b

Single stereoisomer of N-(2-cyclohexyl-1,5-dimethyl-3-oxo-2,3-dihydro-1H-pyrazol-4-yl)-4-methyl-5-(5-methyltetrahydro-2H-pyran-2-yl)isoxazole-3-carboxamide

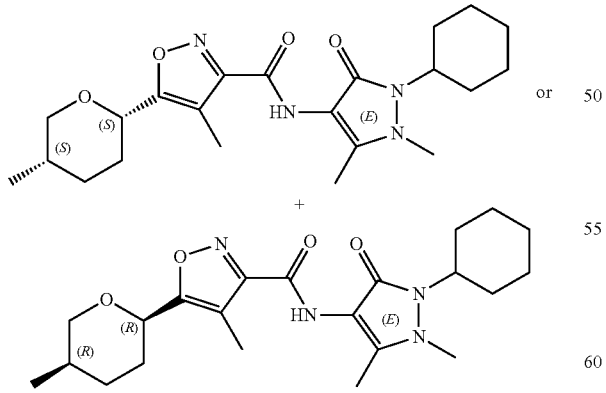

SFC retention time=8.12 mins $^1$H NMR (400 MHz, CDCl$_3$) δ 8.10 (1H, br s), 4.79-4.76 (1H, br mult), 4.06 (1H, tt), 3.75-3.70 (1H, dd), 3.53-3.48 (1H, dd), 3.27 (3H, s), 2.28 (3H, s), 2.22 (3H, s), 2.03-1.95 (2H, mult), 1.92-1.77 (8H, br mults), 1.71 (1H, br mult), 1.66-1.59 (1H, br mult), 1.42-1.32 (2H, br mults), 1.27-1.20 (1H, br mult), 1.05 (3H, d).

Example 22.c

A mixture of N-(2-Cyclohexyl-1,5-dimethyl-3-oxo-2,3-dihydro-1H-pyrazol-4-yl)-4-methyl-5-((2S,5R)-5-methyltetrahydro-2H-pyran-2-yl)isoxazole-3-carboxamide and N-(2-Cyclohexyl-1,5-dimethyl-3-oxo-2,3-dihydro-1H-pyrazol-4-yl)-4-methyl-5-((2R,5S)-5-methyltetrahydro-2H-pyran-2-yl)isoxazole-3-carboxamide

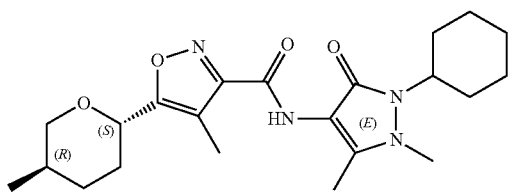

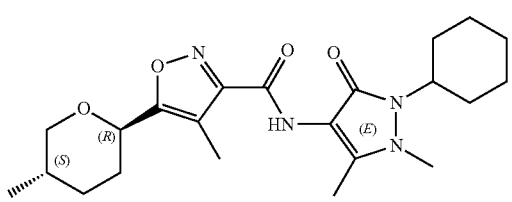

SFC retention time=5.84 mins $^1$H NMR (400 MHz, CDCl$_3$) δ 8.10 (1H, br s), 4.50 (1H, dd), 4.10-3.98 (2H, br mults), 3.26 (3H, s), 3.17 (1H, t), 2.27 (3H, s), 2.21 (3H, s), 2.09-1.92 (4H, br mults), 1.93-0.177 (7H, br mults), 1.71 (1H, br d), 1.42-1.17 (3H, br mults), 0.87 (3H, d).

Example 23

A mixture of 5-((2R,4S)-4-(2-bromopropan-2-yl)tetrahydrofuran-2-yl)-N-(2-cyclohexyl-1,5-dimethyl-3-oxo-2,3-dihydro-1H-pyrazol-4-yl)-4-methylisoxazole-3-carboxamide and 5-((2S,4R)-4-(2-bromopropan-2-yl)tetrahydrofuran-2-yl)-N-(2-cyclohexyl-1,5-dimethyl-3-oxo-2,3-dihydro-1H-pyrazol-4-yl)-4-methylisoxazole-3-carboxamide

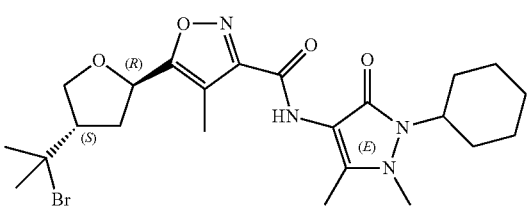

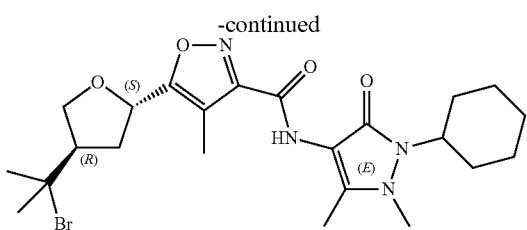

Step 1: 2,2-Dimethylbut-3-en-1-ol

A solution of 2,2-dimethylbut-3-yn-1-ol (PharmaBlocks) (3 g, 30.6 mmol) in dry diethyl ether (40 mL) was added 2,2'-(ethane-1,2-diylbis(sulfanediyl))diethanol (5.57 g, 30.6 mmol), followed by 5% Pd on barium sulphate (Aldrich) (6.51 g, 3.06 mmol). The mixture was degassed thoroughly refilling with nitrogen and stirred under an atmosphere of hydrogen at room temperature for 4 hours. The resulting mixture was filtered under reduced pressure, washing the catalyst with diethyl ether. The filtrate was concentrated carefully under reduced pressure to remove most of the solvent. The resulting suspension was filtered and the filtrate concentrated under reduced pressure to afford the title compound;

$^1$H NMR (400 MHz, CDCl$_3$) δ 5.71 (1H, dd), 5.05-4.97 (2H, mults), 3.27 (2H, s), 1.41 (1H, br mult), 0.95 (6H, s).

Step 2: A mixture of ethyl 5-((2R,4S)-4-(2-bromopropan-2-yl)tetrahydrofuran-2-yl)-4-methylisoxazole-3-carboxylate and ethyl 5-((2S,4R)-4-(2-bromopropan-2-yl)tetrahydrofuran-2-yl)-4-methylisoxazole-3-carboxylate To an ice-cooled mixture of 2,2-dimethylbut-3-en-1-ol (328 mg, 3.28 mmol), indium (III) bromide (56.6 mg, 0.164 mmol) and dry DCM (20 mL) under nitrogen was added bromotrimethylsilane (0.425 mL, 3.28 mmol) and the resulting mixture was stirred with ice cooling for 30 mins. A solution of ice cold ethyl 5-formyl-4-methylisoxazole-3-carboxylate (Intermediate C) (600 mg, 3.28 mmol) in dry DCM (2 mL) was added to the reaction mixture over a 15 minute period and the reaction mixture was stirred with ice-cooling for 85 minutes. The resulting mixture was treated with saturated aqueous NaHCO$_3$ (10 mL) with stirring at 0° C. The biphasic mixture was passed through a phase separating cartridge and the filtrate was concentrated under reduced pressure. The crude material was adsorbed onto silica and purification by chromatography eluting with 0-60% EtOAc in isohexane afforded the title compound;

LC-MS: Rt=1.48 mins; MS m/z [M+H]+346.2/348.2: Method 2minLowpHv03

$^1$H NMR (400 MHz, CDCl$_3$) δ 5.12 (1H, dd), 4.45 (2H, q), 4.10-4.01 (2H, mult), 2.73-2.65 (1H, mult), 2.46-2.39 (1H, mult), 2.27 (3H, s), 1.82 (3H, s), 1.80 (3H, s), 1.43 (3H, t).

Step 3: A mixture of 5-((2R,4S)-4-(2-bromopropan-2-yl)tetrahydrofuran-2-yl)-4-methylisoxazole-3-carboxylic acid and 5-((2S,4R)-4-(2-bromopropan-2-yl)tetrahydrofuran-2-yl)-4-methylisoxazole-3-carboxylic acid To a stirred solution of a mixture of ethyl 5-((2R,4S)-4-(2-bromopropan-2-yl)tetrahydrofuran-2-yl)-4-methylisoxazole-3-carboxylate and ethyl 5-((2S,4R)-4-(2-bromopropan-2-yl)tetrahydrofuran-2-yl)-4-methylisoxazole-3-carboxylate (442 mg, 1.277 mmol) in THF (10 mL) and MeOH (1 mL) was added 2M NaOH (aq) (1.277 mL, 2.55 mmol). The reaction mixture was stirred at room temperature. Upon completion the reaction was added to water (20 mL) and acidified to pH 5-6 by addition of 1M HCl (aq). The aqueous was extracted with EtOAc (40 mL) and the combined organic extracts were washed with brine (20 mL), dried over MgSO$_4$ and filtered. The solvent was removed under reduced pressure to afford the title compound;

LC-MS: Rt=1.18 mins; MS m/z [M+H]+318.4/320.5: Method 2minLowpHv03

Step 4: A mixture of 5-((2R,4S)-4-(2-bromopropan-2-yl)tetrahydrofuran-2-yl)-N-(2-cyclohexyl-1,5-dimethyl-3-oxo-2,3-dihydro-1H-pyrazol-4-yl)-4-methylisoxazole-3-carboxamide and 5-((2S,4R)-4-(2-bromopropan-2-yl)tetrahydrofuran-2-yl)-N-(2-cyclohexyl-1,5-dimethyl-3-oxo-2,3-dihydro-1H-pyrazol-4-yl)-4-methylisoxazole-3-carboxamide To a stirred mixture of DMF (0.073 mL, 0.943 mmol) in dry DCM (15 mL) under nitrogen at 0° C., oxalyl chloride (0.045 mL, 0.519 mmol) was added. After 5 minutes a solution of a mixture of 5-((2R,4S)-4-(2-bromopropan-2-yl)tetrahydrofuran-2-yl)-4-methylisoxazole-3-carboxylic acid and 5-((2S,4R)-4-(2-bromopropan-2-yl)tetrahydrofuran-2-yl)-4-methylisoxazole-3-carboxylic acid (150 mg, 0.471 mmol) in dry DCM (3 mL) was added and the reaction mixture was stirred for 10 minutes. A solution of 4-amino-2-cyclohexyl-1,5-dimethyl-1H-pyrazol-3(2H)-one (Intermediate D) (109 mg, 0.519 mmol) in dry DCM (2 mL) and triethylamine (0.197 mL, 1.414 mmol) were added and the reaction mixture was stirred at 0° C. for 40 minutes. The resulting mixture was partitioned between DCM (30 mL) and saturated aqueous NaHCO$_3$ (30 mL). The organics were passed through a phase separating column and the eluent was concentrated under reduced pressure. The crude material was dissolved in DMSO and purified using UV-directed automated reverse phase chromatography over a 9.5 minute gradient of 30-70% MeCN in water (0.1% formic acid). The product fractions were added to EtOAc (50 mL) and washed with saturated aqueous NaHCO$_3$ (50 mL). The organic layers were dried over MgSO$_4$, filtered and the solvent removed under reduced pressure to afford the title compounds;

LC: Rt=1.26 mins: Method 2minLowpHv03

$^1$H NMR (400 MHz, CDCl$_3$) δ 8.06 (1H, br s), 5.19 (1H, t), 4.53 (1H, mult), 4.40 (1H, mult), 4.05 (1H, tt), 3.26 (3H, s), 2.92-2.77 (2H, br mult), 2.28 (3H, s), 2.21 (3H, s), 2.06-1.94

(2H, br mults), 1.92-1.83 (4H, br mults), 1.72 (3H, s), 1.72-1.63 (1H, br mults), 1.64 (3H, s), 1.44-1.30 (2H, br mults), 1.29-1.19 (1H, br mult).

Example 24

A mixture of N-(2-cyclohexyl-1,5-dimethyl-3-oxo-2,3-dihydro-1H-pyrazol-4-yl)-5-((2R,4R)-4-isopropyltetrahydrofuran-2-yl)-4-methylisoxazole-3-carboxamide and N-(2-cyclohexyl-1,5-dimethyl-3-oxo-2,3-dihydro-1H-pyrazol-4-yl)-5-((2S,4S)-4-isopropyltetrahydrofuran-2-yl)-4-methylisoxazole-3-carboxamide

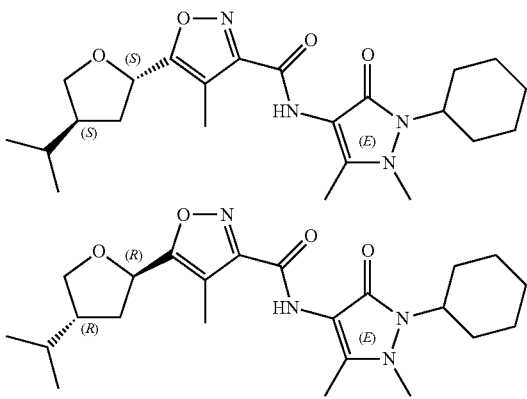

To 5-(4-(2-bromopropan-2-yl)tetrahydrofuran-2-yl)-N-(2-cyclohexyl-1,5-dimethyl-3-oxo-2,3-dihydro-1H-pyrazol-4-yl)-4-methylisoxazole-3-carboxamide (62 mg, 0.122 mmol) in ethanol (10 mL) under a flow of nitrogen was added Pd—C (5.18 mg, 0.049 mmol). The mixture was stirred under an atmosphere of hydrogen at 0.35 bar and room temperature overnight. To the reaction mixture was added NaHCO$_3$ (40.9 mg, 0.487 mmol) and the reaction mixture was stirred under an atmosphere of hydrogen at 0.35 bar and room temperature for 2.5 hours. The resulting mixture was filtered through Celite®, washing with EtOH. The filtrate was passed through a Biotage 1 g Silica-TMT cartridge and the eluent was removed under reduced pressure. The crude material was purified by Preparative HPLC-MS over a 9.5 minute gradient of 30-98% MeCN in water (0.1% TFA). The product fractions were dissolved in EtOAc (20 mL) and washed with saturated aqueous NaHCO$_3$ (20 mL). The organic layer was washed with brine (10 mL), dried over MgSO$_4$, filtered and the solvent removed under reduced pressure to afford the title compounds;

LC-MS: Rt=1.30 mins; MS m/z [M+H]+431.5: Method 2minLowpHv03.

Chiral separation of Example 24 using Supercritical Fluid Chromatography afforded the single enantiomers.

Method Details:

Column: Chiralpak IB, 250×10 mm, 5 um @35 deg C.

Mobile phase: 40% Isopropanol+0.1% v/v DEA/60% CO2

Flow: 10 ml/min

Detection: UV @220 nm

Instrument: Berger Minigram SFC1

Example 24.a

N-(2-Cyclohexyl-1,5-dimethyl-3-oxo-2,3-dihydro-1H-pyrazol-4-yl)-5-((2R,4R)-4-isopropyltetrahydrofuran-2-yl)-4-methylisoxazole-3-carboxamide or N-(2-cyclohexyl-1,5-dimethyl-3-oxo-2,3-dihydro-1H-pyrazol-4-yl)-5-((2S,4S)-4-isopropyltetrahydrofuran-2-yl)-4-methylisoxazole-3-carboxamide SFC Rt=3.99 mins LC-MS; Rt=1.30 mins; MS m/z [M+H]+431.5; Method 2minLowpHv03

$^1$H NMR (400 MHz, CDCl$_3$) δ 7.99 (1H, br s), 5.09 (1H, mult), 4.09 (1H, t), 4.10-4.00 (1H, tt), 3.69 (1H, t), 3.24 (3H, s), 2.45-2.36 (1H, mult), 2.25 (3H, s), 2.21 (3H, s), 2.18-2.09 (1H, br mult), 2.06-1.93 (2H, br mults), 1.91-1.83 (5H, br mults), 1.71 (1H, br mult), 1.67-1.60 (1H, br mult), 1.44-1.30 (2H, br mults), 1.29-1.19 (1H, br mult), 1.00 (3H, d), 0.95 (3H, d).

Example 24.b

N-(2-Cyclohexyl-1,5-dimethyl-3-oxo-2,3-dihydro-1H-pyrazol-4-yl)-5-((2R,4R)-4-isopropyltetrahydrofuran-2-yl)-4-methylisoxazole-3-carboxamide or N-(2-cyclohexyl-1,5-dimethyl-3-oxo-2,3-dihydro-1H-pyrazol-4-yl)-5-((2S,4S)-4-isopropyltetrahydrofuran-2-yl)-4-methylisoxazole-3-carboxamide SFC Rt=5.42 mins LC-MS: Rt 1.30 mins; MS m/z [M+H]+431.6: Method 2minLowpHv03

$^1$H NMR (400 MHz, CDCl$_3$) δ 8.06 (1H, br s), 5.12-5.06 (1H, mult), 4.12-4.01 (2H, mults), 3.69 (1H, t), 3.26 (3H, s), 2.44-2.36 (1H, mult), 2.26 (3H, s), 2.21 (3H, s), 2.18-2.08 (1H, mult), 2.05-1.95 (2H, br mults), 1.91-1.83 (5H, br mults), 1.71 (1H, br mult), 1.68-1.59 (1H, mult), 1.44-1.31 (2H, br mults), 1.30-1.19 (1H, br mult), 1.00 (3H, s), 0.95 (3H, s).

Example 25

5-(4-(tert-butyl)-1,3-dioxolan-2-yl)-N-(2-cyclohexyl-1,5-dimethyl-3-oxo-2,3-dihydro-1H-pyrazol-4-yl)-4-methylisoxazole-3-carboxamide

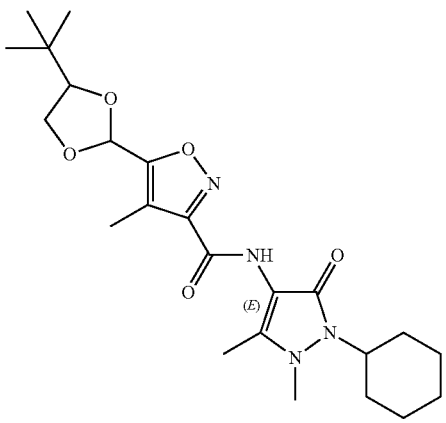 [SMILES: Cc1c(C(=O)Nc2c(C)n(C)n(C3CCCCC3)c2=O)noc1C1OCC(C(C)(C)C)O1]

Step 1: Ethyl 5-(4-(tert-butyl)-1,3-dioxolan-2-yl)-4-methylisoxazole-3-carboxylate To a solution of ethyl 5-formyl-4-methylisoxazole-3-carboxylate (Intermediate C) (50 mg, 0.273 mmol) in toluene (0.5 mL) was added 3,3-dimethylbutane-1,2-diol (32.3 mg, 0.273 mmol) and the mixture was heated at 110° C. for 4.5 hours. The resulting mixture was partitioned between EtOAc and water and the organic layer was dried over MgSO$_4$, filtered and the solvent removed under reduced pressure. The crude material was adsorbed onto silica and purification by chromatography eluting with 0-100% EtOAc in iso-hexane afforded the title compound;

LC-MS: Rt=1.42 mins; MS m/z [M+H]+284.3: Method 2minHighpHv03

Step 2: Potassium 5-(4-(tert-butyl)-1,3-dioxolan-2-yl)-4-methylisoxazole-3-carboxylate To a solution of ethyl 5-(4-(tert-butyl)-1,3-dioxolan-2-yl)-4-methylisoxazole-3-carboxylate (42 mg, 0.148 mmol) in THF (4 mL) was added potassium trimethylsilanolate (19.02 mg, 0.148 mmol) and the mixture was stirred at room temperature for 1.5 hours. The resulting mixture was concentrated under reduced pressure to afford the title compound.

Step 3: A mixture of 5-((2R,4R)-4-(tert-butyl)-1,3-dioxolan-2-yl)-N-(2-cyclohexyl-1,5-dimethyl-3-oxo-2,3-dihydro-1H-pyrazol-4-yl)-4-methylisoxazole-3-carboxamide and 5-((2R,4S)-4-(tert-butyl)-1,3-dioxolan-2-yl)-N-(2-cyclohexyl-1,5-dimethyl-3-oxo-2,3-dihydro-1H-pyrazol-4-yl)-4-methylisoxazole-3-carboxamide and 5-((2S,4R)-4-(tert-butyl)-1,3-dioxolan-2-yl)-N-(2-cyclohexyl-1,5-dimethyl-3-oxo-2,3-dihydro-1H-pyrazol-4-yl)-4-methylisoxazole-3-carboxamide and 5-((2S,4S)-4-(tert-butyl)-1,3-dioxolan-2-yl)-N-(2-cyclohexyl-1,5-dimethyl-3-oxo-2,3-dihydro-1H-pyrazol-4-yl)-4-methylisoxazole-3-carboxamide To a solution of potassium 5-(4-(tert-butyl)-1,3-dioxolan-2-yl)-4-methylisoxazole-3-carboxylate (43.5 mg, 0.148 mmol) in NMP (0.7 mL) was added HATU (62.0 mg, 0.163 mmol), triethylamine (45.5 µl, 0.326 mmol) and 4-amino-2-cyclohexyl-1,5-dimethyl-1H-pyrazol-3(2H)-one (Intermediate D) (31.0 mg, 0.148 mmol) and the reaction mixture was stirred at room temperature overnight. To the resulting mixture was added water and EtOAc. The organics were washed with brine (×2), dried over MgSO$_4$, filtered and the solvent removed under reduced pressure. The crude material was adsorbed onto silica and purification by chromatography eluting with 0-100% EtOAc in iso-hexane afforded the title compound as a mixture of diastereoisomers.

Example 25a-25d 5-((2R,4R)-4-(tert-butyl)-1,3-dioxolan-2-yl)-N-(2-cyclohexyl-1,5-dimethyl-3-oxo-2,3-dihydro-1H-pyrazol-4-yl)-4-methylisoxazole-3-carboxamide or
5-((2R,4S)-4-(tert-butyl)-1,3-dioxolan-2-yl)-N-(2-cyclohexyl-1,5-dimethyl-3-oxo-2,3-dihydro-1H-pyrazol-4-yl)-4-methylisoxazole-3-carboxamide or
5-((2S,4R)-4-(tert-butyl)-1,3-dioxolan-2-yl)-N-(2-cyclohexyl-1,5-dimethyl-3-oxo-2,3-dihydro-1H-pyrazol-4-yl)-4-methylisoxazole-3-carboxamide or
5-((2S,4S)-4-(tert-butyl)-1,3-dioxolan-2-yl)-N-(2-cyclohexyl-1,5-dimethyl-3-oxo-2,3-dihydro-1H-pyrazol-4-yl)-4-methylisoxazole-3-carboxamide

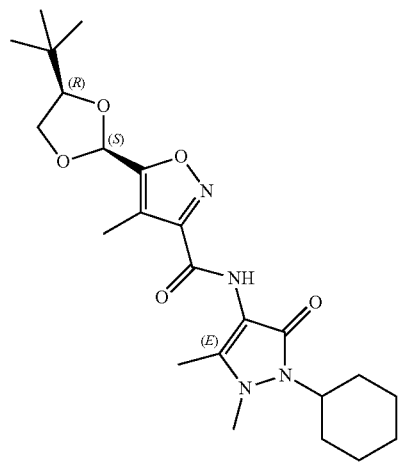

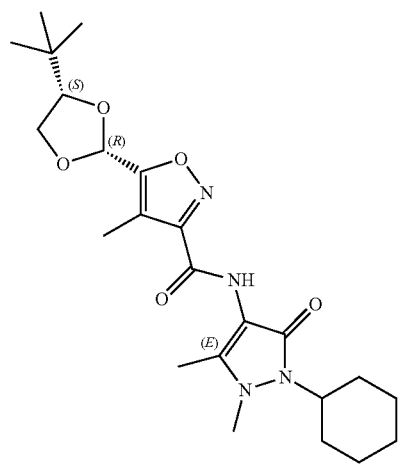

103
-continued

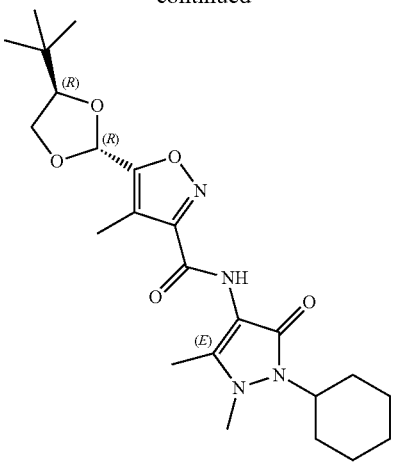

Chiral separation of 5-(4-(tert-butyl)-1,3-dioxolan-2-yl)-N-(2-cyclohexyl-1,5-dimethyl-3-oxo-2,3-dihydro-1H-pyrazol-4-yl)-4-methylisoxazole-3-carboxamide using Supercritical Fluid Chromatography afforded the individual enantiomers.

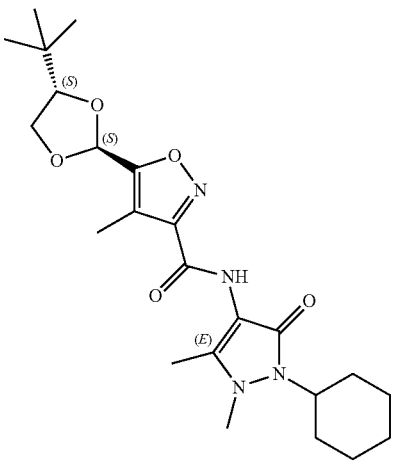

Method Details:
Column: Chiralpak IB, 250×10 mm, 5 um @35 deg C.
Mobile phase: 35% Isopropanol+0.1% v/v DEA/65% CO2
Flow: 10 ml/min
Detection: UV @220 nm
Instrument: Berger Minigram SFC1

Example 25a

Single stereoisomer of 5-(4-(tert-butyl)-1,3-dioxolan-2-yl)-N-(2-cyclohexyl-1,5-dimethyl-3-oxo-2,3-dihydro-1H-pyrazol-4-yl)-4-methylisoxazole-3-carboxamide SFC: Rt=3.36 mins LC-MS: Rt=4.11 mins; MS m/z [M+H]+447.6: Method 8minLowpHv01
$^1$H NMR (400 MHz, CDCl$_3$) δ 8.29 (1H, br s), 6.02 (1H, s), 4.14-4.00 (2H, mults), 3.97-3.87 (2H, mults), 3.36 (3H, s), 2.31 (3H, s), 2.23 (3H, s), 2.09-1.97 (2H, mults), 1.88 (3H, br t), 1.73 (1H, br d), 1.44-1.31 (2H, mults), 1.30-1.20 (2H, mults), 1.01 (9H, s).

Example 25b

Single stereoisomer of 5-(4-(tert-Butyl)-1,3-dioxolan-2-yl)-N-(2-cyclohexyl-1,5-dimethyl-3-oxo-2,3-dihydro-1H-pyrazol-4-yl)-4-methylisoxazole-3-carboxamide Chiral SFC: Rt=3.78 mins LC-MS: Rt=4.12 mins; MS m/z [M+H]+447.5; Method 8minLowpHv01
$^1$H NMR (400 MHz, CDCl$_3$) δ 8.06 (1H, br s), 6.19 (1H, s), 4.16-4.00 (3H, mults), 3.85 (1H, t), 3.30 (3H, s), 2.30 (3H, s), 2.22 (3H, s), 2.07-1.94 (2H, mults), 1.87 (3H, br t), 1.72 (1H, br d), 1.45-1.20 (4H, mults), 0.99 (9H, s).

Example 25c

Single stereoisomer of 5-(4-(tert-Butyl)-1,3-dioxolan-2-yl)-N-(2-cyclohexyl-1,5-dimethyl-3-oxo-2,3-dihydro-1H-pyrazol-4-yl)-4-methylisoxazole-3-carboxamide Chiral SFC: Rt=4.05 mins LC-MS: Rt=4.09 mins; MS m/z [M+H]+447.5; Method 8minLowpHv01
$^1$H NMR (400 MHz, CDCl$_3$) δ 7.99 (1H, br s), 6.02 (1H, s), 4.10-4.01 (2H, mults), 3.97-3.87 (2H, mults), 3.25 (3H, s), 2.32 (3H, s), 2.21 (3H, s), 2.06-1.93 (2H, mults), 1.88 (3H, br t), 1.71 (1H, br d), 1.44-1.30 (2H, mults), 1.30-1.20 (2H, mults), 1.00 (9H, s).

Example 25d

Single stereoisomer of 5-(4-(tert-Butyl)-1,3-dioxolan-2-yl)-N-(2-cyclohexyl-1,5-dimethyl-3-oxo-2,3-dihydro-1H-pyrazol-4-yl)-4-methylisoxazole-3-carboxamide Chiral SFC: Rt=5.95 mins LC-MS: Rt=4.15 mins; MS m/z [M+H]+447.6; Method 8minLowpHv01
$^1$H NMR (400 MHz, CDCl$_3$) δ 8.00 (1H, br s), 6.20 (1H, s), 4.16-4.09 (2H, mults), 4.07-4.00 (2H, mults), 3.27 (3H, s), 2.30 (3H, s), 2.21 (3H, s), 2.07-1.94 (2H, mults), 1.87 (3H, br t), 1.72 (1H, br d), 1.45-1.20 (4H, mults), 0.99 (9H, s).

Example 26

N-(2-Cyclohexyl-1,5-dimethyl-3-oxo-2,3-dihydro-1H-pyrazol-4-yl)-5-(5,5-dimethyl-1,3-dioxan-2-yl)-4-methylisoxazole-3-carboxamide

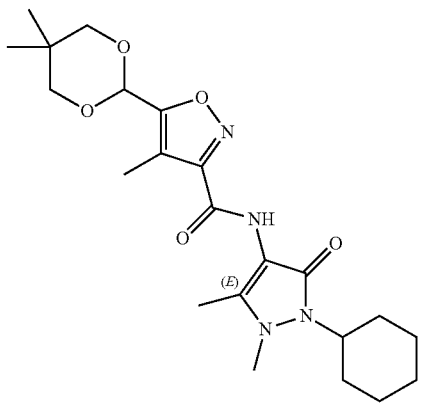 [SMILES: Cc1c(C(=O)Nc2c(C)n(C)n(C3CCCCC3)c2=O)noc1C1OCC(C)(C)CO1]

The title compound was prepared by a method similar to that of Example 25 by replacing 3,3-dimethylbutane-1,2-diol (Step 1) with 2,2-dimethylpropane-1,3-diol;

LC-MS: Rt=3.68 mins; MS m/z [M+H]+433.4; Method 8minLowpHv01

$^1$H NMR (400 MHz, CDCl$_3$) δ 7.98 (1H, s), 5.58 (1H, s), 3.96 (1H, tt), 3.71 (2H, d), 3.55 (2H, d), 3.18 (3H, s), 2.26 (3H, s), 2.11 (3H, s), 1.97-1.86 (2H, mults), 1.80-1.74 (3H, mults), 1.62 (1H, br d), 1.33-1.11 (4H, mults), 1.23 (3H, s), 0.75 (3H, s).

Intermediate A

Ethyl 5-bromo-4-methylisoxazole-3-carboxylate

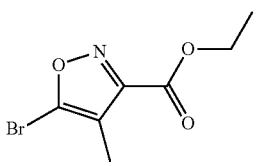

Step 1: Ethyl 4-methyl-5-oxo-4,5-dihydroisoxazole-3-carboxylate

To diethyl oxalyl propionate (300 g, 1.48 mol) in Ethanol (2 l) was added hydroxylamine hydrochloride (124 g, 1.78 mol) and the reaction mixture was heated at 80° C. for 3 hours. The resulting mixture was cooled to room temperature and the solvent removed under reduced pressure. The residue was treated with water and DCM and the aqueous extracted with DCM. The combined organics were dried and the solvent removed under reduced pressure to afford the title compound;

$^1$H NMR (400 MHz, CDCl$_3$) δ 4.40 (2H, q), 2.09 (3H, s), 1.38 (3H, t).

Step 2: Ethyl 5-bromo-4-methylisoxazole-3-carboxylate

Ethyl 4-methyl-5-oxo-4,5-dihydroisoxazole-3-carboxylate (42.5 g, 248 mmol) and phosphorous oxybromide (199 g, 695 mmol) were stirred together and heated to 80° C. Triethylamine (34.6 mL, 248 mmol) was added dropwise over 15 mins and the reaction mixture was stirred at 80° C. for 3 hours. The resulting mixture was cooled to room temperature. DCM (400 mL) was added and the mixture was poured into ice (~400 mL) with stirring. 2M NaOH (aq) (1250 mL) was added until pH 7 and the resulting layers were separated. The aqueous layer was extracted with DCM (2×300 mL) and the resulting organic extracts were combined, washed with water (400 mL), sodium thiosulfate (5% w/v solution, 400 mL), water (400 mL) and brine (400 mL). The organics were dried over MgSO$_4$ and charcoal, filtered and the solvent removed under reduced pressure. The crude material was adsorbed onto silica and purification by chromatography eluting with 0-30% EtOAc in iso-hexane afforded the title compound;

LC-MS: Rt=1.02 mins: MS m/z [M+H]+234.0: Method 2minLowpH $^1$H NMR (400 MHz, CDCl$_3$) δ 4.47 (2H, q), 2.21 (3H, s), 1.44 (3H, t).

Intermediate B

Ethyl 5-((1R,2S)-1,2-dihydroxypropyl)-4-methylisoxazole-3-carboxylate

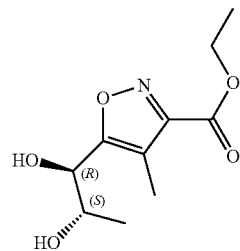

Step 1: (E)-Ethyl 4-methyl-5-(prop-1-en-1-yl)isoxazole-3-carboxylate

A suspension of potassium trans-1-propenyltrifluoroborate (9.86 g, 66.7 mmol), PdCl$_2$(dppf).DCM adduct (907 mg, 1.11 mmol), ethyl 5-bromo-4-methylisoxazole-3-carboxylate (Intermediate A) (13 g) and triethylamine (7.7 mL) in EtOH (250 mL) was degassed under vacuum and back-filled with nitrogen before heating at 90° C. for 18 h. After cooling to room temperature, the reaction was partitioned between EtOAc and brine, separated, dried over MgSO$_4$ and concentrated under reduced pressure. The crude material was adsorbed onto silica and purification by chromatography eluting with 5-10% EtOAc in iso-hexane afforded the title compound;

LC-MS: Rt=1.30 mins; MS m/z [M+H]+196.2; Method 2minLowpHv03

Step 2: Ethyl 5-((1R,2S)-1,2-dihydroxypropyl)-4-methylisoxazole-3-carboxylate (E)-Ethyl 4-methyl-5-(prop-1-en-1-yl)isoxazole-3-carboxylate (500 mg, 2.56 mmol) in tert-BuOH-water (1 mL)

was added portionwise to a mixture of AD-mix-beta (3.59 g, 7.63 mmol), methane sulfonamide (731 mg, 7.68 mmol), modified AD-mix-β (DHQD)₂PHAL (80 mg, 0.102 mmol) and osmium tetroxide (0.836 mL of a 2.5 wt % solution in tert-BuOH, 0.067 mmol) in tert-BuOH-water (1:1, 19 mL) and the resulting reaction mixture was stirred at room temperature for 1.5 hr. Sodium sulfite (3.9 g) was added in one portion and the reaction was left to stir for 30 mins. The phases were separated and the EtOAc phase was dried over Na₂SO₄ and concentrated under reduced pressure. The crude material was adsorbed onto silica and purification by chromatography eluting with 65-75% EtOAc in iso-hexane afforded the title compound (96% ee);

LC-MS: Rt=0.78 mins; MS m/z [M+H]+230.2; Method 2minLowpHv03

Intermediate C

Ethyl 5-formyl-4-methylisoxazole-3-carboxylate

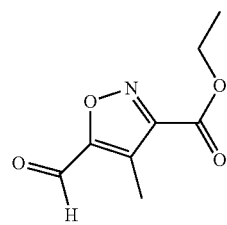

Step 1: Ethyl 4-methyl-5-vinylisoxazole-3-carboxylate

Ethyl 5-bromo-4-methylisoxazole-3-carboxylate (Intermediate A) (15 g, 64.1 mmol) and tributyl(vinyl)stannane (22.48 mL, 77 mmol) were stirred in dry dioxane (250 mL) and purged with nitrogen for 90 minutes at room temperature. Tetrakis(triphenylphosphine)palladium (3.70 g, 3.20 mmol) was added and the reaction mixture was stirred at 100° C. overnight. The reaction mixture was partitioned in ethyl acetate (250 mL) and water (250 mL) and separated. To the organic layer was added sodium fluoride solution (~1M, 250 ml) and the resulting suspension was filtered through Celite®. The layers were separated and the organics were washed with water, brine, dried over MgSO₄ and filtered. The solvent was removed under reduced pressure. The crude material was adsorbed onto silica and purification by chromatography eluting with 0-30% EtOAc in iso-hexane afforded the title compound;

LC-MS: Rt=1.20 mins: MS m/z [M+H]+182.5: Method 2minLowpHv03

Step 2: Ethyl 5-formyl-4-methylisoxazole-3-carboxylate

To ethyl 4-methyl-5-vinylisoxazole-3-carboxylate (3 g, 16.56 mmol) in THF (40 mL) and water (20 mL) at room temperature, was added sodium periodate (10.62 g, 49.7 mmol) and Osmium ENCAT 40 (828 mg, 0.248 mmol). The reaction mixture was stirred at room temperature over the weekend. The resulting mixture was filtered over Celite® (5 g), washing with EtOAc. The layers were separated and the aqueous layer was extracted with EtOAc. The combined organic extracts were dried over MgSO₄, filtered and the solvent was removed under reduced pressure. The crude material was suspended in DCM, sonicated and passed through a phase separating cartridge. The eluent was collected and the solvent removed under reduced pressure to afford the title compound;

¹H NMR (400 MHz, CDCl₃) δ 10.12 (1H, s), 4.50 (2H, q), 2.56 (3H, s), 1.46 (3H, s).

Intermediate D

4-Amino-2-cyclohexyl-1,5-dimethyl-1H-pyrazol-3 (2H)-one

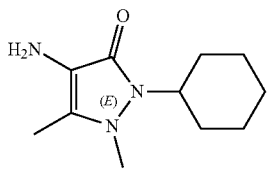

Step 1:
2-Cyclohexyl-5-methyl-1H-pyrazol-3(2H)-one

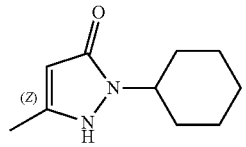

Cyclohexylhydrazine hydrochloride (AK Scientific) (700 g, 4643 mmol) was added to a stirred solution of DCM (3000 mL) and ice cold 2M sodium hydroxide solution (1778 mL, 3556 mmol). The reaction mixture was stirred for 10 minutes at room temperature. The resulting phases were separated and the aqueous layer was extracted with DCM (4×2000 mL). The combined organic extracts were dried over anhydrous sodium sulphate, filtered and concentrated under reduced pressure. The resulting solid was dissolved in water (1300 mL), to which acetic acid (1300 mL) and ethyl acetoacetate (Fluka) (450 mL, 3556 mmol) were added and the reaction mixture was stirred at 85° C. for 1 hour. The resulting mixture was concentrated to dryness under reduced pressure and the residue was dissolved in DCM (3000 mL) and water (1000 mL). The pH was adjusted to pH 9 using 2M K₂CO₃ (aq), the phases were separated and the organic extract was washed with brine (1×2 L). The first aqueous layer was saturated with sodium chloride and the combined aqueous phases were extracted with DCM (4×2 L). The combined organic extracts were dried over anhydrous sodium sulfate, filtered and concentrated under reduced pressure to yield a solid. The crude solid was pulverized, TBME (2000 mL) was added and the mixture was stirred at 50° C. for 1 hour, followed by 1 hour at room temperature. The resulting suspension was filtered, washing the solid with TBME (4×500 mL). The isolated solid was dried under vacuum at 45° C. for 16 hours to afford the title compound;

¹H NMR (400 MHz, DMSO-d6) δ 10.62 (1H, br s), 5.06 (1H, s), 3.89 (1H, mult), 1.98 (3H, s), 1.81-1.55 (7H, mults), 1.36-1.22 (2H, mults), 1.18-1.05 (1H, mult).

Step 2:
2-Cyclohexyl-1,5-dimethyl-1H-pyrazol-3(2H)-one

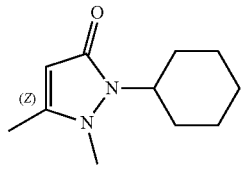

A suspension of 2-cyclohexyl-5-methyl-1H-pyrazol-3(2H)-one (525 g, 2834 mmol) in N,N-dimethylformamide (2200 mL) was heated to 40° C. and methyl iodide (532 mL, 8502 mmol) was added. The reaction mixture was heated to 70° C. for 20 hours. Further methyl iodide (177 mL, 2834 mmol) was added and the mixture was stirred at 75° C. for 3.5 hours, then 80° C. for 20 hours. The resulting mixture was concentrated under reduced pressure and the residue was triturated with TBME (2000 mL). The product was collected by filtration, washing with TBME (5×500 mL) to give a solid. The isolated solid was suspended in DCM (2500 mL) and water (500 mL) and the pH adjusted to pH 9 using an aqueous 2M K₂CO₃ solution (1700 mL). The phases were separated and the aqueous layer was extracted with DCM (3×500 mL). The combined organic extracts were washed with brine (1000 mL) and concentrated under reduced pressure. The resulting residue was dissolved in ethyl acetate (2000 mL), dried over anhydrous sodium sulfate and filtered through 200 g of silica gel (40-63 μm), eluting with 10% MeOH in EtOAc (7×300 mL). The filtrate was concentrated under reduced pressure and dried at 65° C. to afford the title compound;

¹H NMR (400 MHz, DMSO-d6) δ 5.02 (1H, s), 3.84 (1H, tt), 3.14 (3H, s), 2.06 (3H, s), 1.98-1.86 (2H, mults), 1.78-1.53 (5H, mults), 1.33-1.20 (2H, mults), 1.18-1.04 (1H, mult).

Step 3: 2-Cyclohexyl-1,5-dimethyl-4-nitro-1H-pyrazol-3(2H)-one

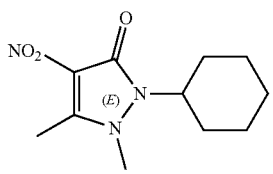 [SMILES: Cc1c([N+](=O)[O-])c(=O)n(C2CCCCC2)n1C]

To trifluoroacetic acid (1940 mL) cooled to −15° C. was added 2-cyclohexyl-1,5-dimethyl-1H-pyrazol-3(2H)-one (535 g, 2231 mmol) and the reaction mixture was cooled to 0° C. Nitric acid 90% (211 mL, 4461 mmol) was added dropwise over 90 minutes maintaining the temperature below 15° C. and the reaction mixture was stirred for 30 minutes at 10° C. The resulting mixture was slowly poured into ice water (8 L) and stirred for 30 minutes. The solid was collected by filtration and washed with water (2×2 L), saturated sodium bicarbonate solution (1×2 L), water (2×2 L), TBME (3×2 L) and heptane (2×2 L). The isolated solid was dried in the vacuum oven to afford the title compound;

¹H NMR (400 MHz, DMSO-d6) δ 4.06 (1H, tt), 3.61 (3H, s), 2.57 (3H, t), 2.15-2.03 (2H, mults), 1.81-1.65 (4H, mults), 1.64-1.55 (1H, mult), 1.38-1.24 (2H, mults), 1.19-1.06 (1H, mult).

Step 4: 4-Amino-2-cyclohexyl-1,5-dimethyl-1H-pyrazol-3(2H)-one

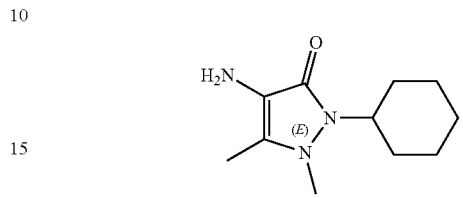

To 2-cyclohexyl-1,5-dimethyl-4-nitro-1H-pyrazol-3(2H)-one (415 g, 1.73 mol) in MeOH (4500 ml) and THF (4500 ml) was added 10% Pd/C (70 g) and the reaction mixture was hydrogenated at 0.1 bar and RT for 57.5 h. The resulting mixture was filtered through a pressure strainer and washed with methanol (1×1 L) and THF (2×1 L). The filtrate was concentrated under reduced pressure to give a dark red oil. The oil was dissolved immediately in TBME (4 L), concentrated under reduced pressure to ca. 2 L and seeded (100 mg). The suspension was stirred for 2 h at RT and cooled in an ice bath for 1 hr. The solid was collected by filtration and washed with ice cold TBME in portionwise until the filtrate was colourless and dried under vacuum to give the title compound;

LC-MS: Rt 0.55 mins; MS m/z 210.1 [M+H]⁺; Method (SRPb)

¹H NMR (400 MHz, DMSO-d6) δ 3.68 (1H, tt), 3.53 (2H, br s), 2.77 (3H, s), 1.96-1.83 (2H, mults), 1.92 (3H, s), 1.78-1.69 (2H, mults), 1.64-1.53 (3H, mults), 1.33-1.19 (2H, mults), 1.17-1.04 (1H, mult).

Intermediate E

4-Amino-2-cyclobutyl-1,5-dimethyl-1H-pyrazol-3(2H)-one

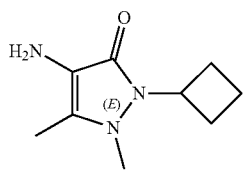

Step 1: tert-Butyl 2-cyclobutylidenehydrazinecarboxylate

A mixture of cyclobutanone (16.96 ml, 227 mmol) and tert-butyl hydrazinecarboxylate (30 g, 227 mmol) in isohexane (378 mL), under nitrogen was stirred at reflux for 1 hour. The reaction mixture was cooled to room temperature and stirred for 1 hour. The resulting suspension was filtered, rinsing the solid with iso-hexane (×2). The solid was dried under vacuum at 30° C. to afford the title compound;

¹H NMR (400 MHz, CDCl₃) δ 7.16 (1H, br s), 3.02 (2H, mult), 2.81 (2H, mult), 2.10-2.00 (2H, mult), 1.53 (9H, s).

Step 2: tert-Butyl 2-cyclobutylhydrazinecarboxylate

A solution of tert-butyl 2-cyclobutylidenehydrazinecarboxylate (5.0 g, 27.1 mmol) in THF (50 mL) was added dropwise over 1.5 hours to a solution of borane tetrahydrofuran complex (33.9 mL, 33.9 mmol) under a nitrogen atmosphere. The reaction mixture was stirred at room temperature for 2.5 hours. Borane tetrahydrofuran (3 mL, 3 mmol) was added dropwise and the mixture was stirred at room temperature overnight. The resulting mixture was quenched cautiously by the addition of water (50 mL) and the mixture was concentrated under reduced pressure. The residue was diluted with water (30 mL) and extracted with EtOAc (2×200 mL), using brine to aid the separation. The combined organic extracts were washed with brine, dried over MgSO$_4$, filtered and the solvent was removed under reduced pressure. The crude material was adsorbed onto silica and purification by chromatography eluting with 0-10% EtOAc in iso-hexane afforded the title compound.

Step 3: 1-Cyclobutyl-2-methylhydrazine

A solution of tert-butyl 2-cyclobutylhydrazinecarboxylate (1.0 g, 5.37 mmol) in THF (26.8 mL) was added dropwise to a solution of 2.4 M lithium aluminum hydride in THF (11.63 mL, 27.9 mmol) under a nitrogen atmosphere. Once the addition was complete the reaction mixture was stirred at reflux for 20 hours. The resulting mixture was cooled using an ice-bath to which water (1 mL), 15% NaOH (1 mL) and water (3 mL) were added. The resulting suspension was stirred for 15 minutes and then filtered through Celite®. To the filtrate was added HCl (4M in dioxane, 1.4 mL, 5.6 mmol) and the solvent removed under reduced pressure, azeotroping with EtOH (×2). The mixture was triturated with ether and the resulting solid filtered and washed with ether. The solid was dried under reduced pressure to afford the title compound.

Step 4: (S)-Methyl 2-((tert-butoxycarbonyl)amino)-3-oxobutanoate

A solution of Dess-Martin periodinane (2.84 g, 6.69 mmol) in DCM (50 mL) was added to a solution of Boc-L-threonine methyl ester (1.3 g, 5.57 mmol) in DCM (20 mL) at room temperature and under a nitrogen atmosphere. The white suspension was stirred at room temperature for 3 hours. The resulting mixture was diluted with DCM (50 mL) and quenched by the addition of saturated NaHCO$_3$ (aq) (50 mL) containing 0.5 M of sodium sulfite (6.2 g). The phases were separated and the organic layer was washed with saturated NaHCO$_3$ (aq) (50 mL) and water, dried over MgSO$_4$, filtered and the solvent removed under reduced pressure. The crude material was adsorbed onto silica and purification by chromatography eluting with 10-50% EtOAc in iso-hexane afforded the title compound;

$^1$H NMR (400 MHz, CDCl$_3$) δ 5.72 (1H, br d), 5.07 (1H, d), 3.84 (3H, s), 2.38 (3H, s), 1.46 (9H, s).

Step 5: tert-Butyl (2-cyclobutyl-1,5-dimethyl-3-oxo-2,3-dihydro-1H-pyrazol-4-yl)carbamate A solution of (S)-methyl 2-((tert-butoxycarbonyl)amino)-3-oxobutanoate (400 mg, 1.730 mmol) in EtOAc (6.407 mL) was treated with 1-cyclobutyl-2-methylhydrazine (284 mg, 2.076 mmol) followed by sodium acetate (213 mg, 2.59 mmol). The suspension was stirred at room temperature for 30 minutes and at 80° C. for 4 hours. The resulting mixture was diluted with water (10 mL) and EtOAc was added. The layers were separated and aqueous extracted with EtOAc. The combined organic layers were washed with brine, dried over MgSO$_4$, filtered and the solvent removed under reduced pressure. The residue was dissolved in EtOAc and iso-hexane was added. The resulting suspension was filtered and the solid rinsed with iso-hexane. The filtrate was concentrated under reduced pressure. The crude material was then adsorbed onto silica and purification by chromatography eluting with 50-100% EtOAc in iso-hexane afforded the title compound;

$^1$H NMR (400 MHz, CDCl$_3$) δ 6.19 (1H, br s), 4.61 (1H, mult), 3.23 (3H, s), 2.85-2.72 (2H, mults), 2.39-2.30 (2H, mults), 2.17 (3H, s), 1.93-1.83 (1H, mult), 1.81-1.71 (1H, mult), 1.48 (9H, s).

Step 6: 4-Amino-2-cyclobutyl-1,5-dimethyl-1H-pyrazol-3(2H)-one

To a solution of tert-butyl (2-cyclobutyl-1,5-dimethyl-3-oxo-2,3-dihydro-1H-pyrazol-4-yl)carbamate in DCM (5 mL) was added sulfuric acid (0.034 mL, 0.634 mmol). The reaction mixture was stirred at room temperature overnight. Further sulfuric acid (0.068 mL, 1.268 mmol) was added to the reaction mixture and it was stirred for 2 hours. The resulting mixture was diluted with DCM and water and the layers separated. The aqueous layer was made basic by the dropwise addition of 2M NaOH (aq). The aqueous layer was extracted with DCM (×3) and the combined organic extracts were passed through a phase separating cartridge. The eluent was concentrated under reduced pressure to afford the title compound;

$^1$H NMR (400 MHz, CDCl$_3$) δ 4.54 (1H, mult), 2.94 (3H, s), 2.72 (2H, mults), 2.43 (2H, br s), 2.36-2.26 (2H, mults), 2.04 (3H, s), 1.90-1.78 (1H, mult), 1.78-1.67 (1H, mult).

Intermediate F 2,2-Dimethylhex-5-en-3-ol

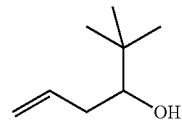

To a solution of trimethylacetaldehyde (10.2 mL, 90.9 mmol) in diethyl ether (200 mL) at 0° C. was added allylmagnesium bromide (100 mL, 1M in ether). The reaction mixture was stirred at 0° C. for 1 hour. The resulting mixture was quenched with saturated ammonium chloride and extracted with diethyl ether. The organic extracts were washed with brine, dried over Na$_2$SO$_4$ and filtered. The solvent was carefully removed under reduced pressure to afford the title compound;

$^1$H NMR (400 MHz, CDCl$_3$) δ 5.95-5.83 (1H, mult), 5.18 (1H, mult), 5.15 (1H, mult), 3.28 (1H, mult), 2.45-2.35 (1H, mult), 2.06-1.95 (1H, mult), 1.62 (1H, s), 0.95 (9H, s).

Intermediate G

4-Amino-2-isopropyl-1,5-dimethyl-1H-pyrazol-3(2H)-one

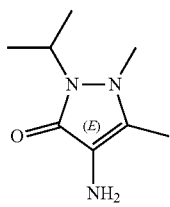

Step 1: Methyl 2-((((9H-fluoren-9-yl)methoxy)carbonyl)amino)-3-hydroxybutanoate

To a solution of 2-((((9H-fluoren-9-yl)methoxy)carbonyl)amino)-3-hydroxybutanoic acid (5 g, 14.65 mmol) in MeOH (50 mL) was added H$_2$SO$_4$ (0.781 mL, 14.65 mmol). The reaction mixture was stirred at reflux overnight. The resulting mixture was cooled to room temperature and the solvent removed under reduced pressure. The crude material was adsorbed onto silica and purification by chromatography using a gradient of 0-100% EtOAc in iso-hexane afforded the title compound;
LC-MS: Rt=1.27 mins; MS m/z [M+H]+356.3: Method 2minLowpHv03

Step 2: Methyl 2-((((9H-fluoren-9-yl)methoxy)carbonyl)amino)-3-oxobutanoate

To a solution of methyl 2-((((9H-fluoren-9-yl)methoxy)carbonyl)amino)-3-hydroxybutanoate (1.5 g, 4.22 mmol) in DCM (25 mL) was added portionwise Dess-Martin periodinane (1.790 g, 4.22 mmol). The reaction mixture was stirred at room temperature overnight. The resulting mixture was diluted with DCM and a 1:1 2M sodium carbonate (aq) and saturated sodium sulphite solution (aq) were added and stirred at room temperature for 15 minutes. The layers were separated and the organic layer dried over MgSO$_4$ and filtered. The solvent was removed under reduced pressure to afford the title compound;
LC-MS: Rt=1.36 mins; MS m/z [M+H]+354.3: Method 2minLowpHv03

Step 3: (9H-Fluoren-9-yl)methyl (2-isopropyl-5-methyl-3-oxo-2,3-dihydro-1H-pyrazol-4-yl)carbamate To a solution of methyl 2-((((9H-fluoren-9-yl)methoxy)carbonyl)amino)-3-oxobutanoate (2.766 g, 7.83 mmol) in 1.25M HCl in ethanol (25 mL) was added isopropylhydrazine hydrochloride (1.298 g, 11.74 mmol). The reaction mixture was stirred at reflux. Upon completion the reaction mixture was cooled to room temperature and the solvent was removed under reduced pressure. The crude material was adsorbed onto silica and purification by chromatography using a gradient of 0-100% EtOAc in iso-hexane and 10% MeOH in EtOAc afforded crude material. The crude material was dissolved in IPA to which water was added to give a cloudy mixture that was sonicated and left to stand at room temperature. The resulting suspension was filtered and the solid dried under reduced pressure to afford the title compound;
LC-MS: Rt=1.14 mins; MS m/z [M+H]+378.3/379.3: Method 2minLowpHv03

Step 4: (9H-Fluoren-9-yl)methyl (2-isopropyl-1,5-dimethyl-3-oxo-2,3-dihydro-1H-pyrazol-4-yl)carbamate To a solution of (9H-fluoren-9-yl)methyl (2-isopropyl-5-methyl-3-oxo-2,3-dihydro-1H-pyrazol-4-yl)carbamate (2.109 g, 5.59 mmol) in DMF (30 mL) was added methyl iodide (2.80 mL, 44.7 mmol). The reaction mixture was stirred at 90° C. overnight. The resulting mixture was quenched with IPA and water and extracted with EtOAc. The combined organic extracts were washed with brine, dried over MgSO$_4$, filtered and the solvent removed under reduced pressure. The crude material was adsorbed onto silica and purification by chromatography using a gradient of 0-10% MeOH in EtOAc afforded the title compound;
LC-MS: Rt=1.20 mins; MS m/z [M+H]+392.4: Method 2minLowpHv03

Step 5: 4-Amino-2-isopropyl-1,5-dimethyl-1H-pyrazol-3(2H)-one

To a solution of (9H-fluoren-9-yl)methyl (2-isopropyl-1,5-dimethyl-3-oxo-2,3-dihydro-1H-pyrazol-4-yl)carbamate (2.047 g, 5.23 mmol) in DMF (30 mL) was added piperidine (2.59 mL, 26.1 mmol) at room temperature. Upon completion of addition the reaction mixture was added to water (30 mL). The resulting suspension was diluted with water (100 mL) and extracted with EtOAc. The combined organics were extracted with 2M HCl (aq) and the acidic aqueous extracts were neutralised with a saturated sodium bicarbonate solution and loaded onto a C18 cartridge. The column was eluted with water and the collected aqueous was slurried with SCX-2 and filtered. The resin was rinsed with MeOH and 7M ammonia in MeOH. The MeOH and aqueous filtrate solvent was removed under reduced pressure. MeOH (150 mL) was added to the resulting mixture, sonicated, filtered and the filtrate was concentrated under reduced pressure. EtOH was added to the resulting mixture and it was filtered. The filtrate was concentrated under reduced pressure. The crude material was adsorbed onto silica and purification by chromatography using a gradient of 0-10% MeOH in DCM afforded crude material. The crude material in MeOH was slurried with SCX-2 (30 g). The suspension was filtered and washed with MeOH. The resin was then eluted with 7M NH$_3$ in MeOH. The methanolic ammonia was concentrated under reduced pressure to afford crude material. The crude material was then adsorbed onto silica and purification by chromatography using a gradient of 0-10% MeOH in DCM afforded the title compound;
LC-MS: Rt=1.48 mins; MS m/z [M+H]+170.2: 8minHighpHv01
$^1$H NMR (400 MHz, DMSO-d6) δ 9.72 (2H, br s), 4.42 (1H, mult), 3.28 (3H, s), 2.25 (3H, s), 1.36 (6H, d).

The invention claimed is:

1. A compound of formula (I):

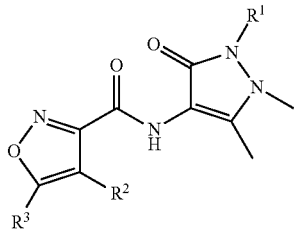

or a pharmaceutically acceptable salt thereof, wherein

R$^1$ is (C$_3$-C$_6$)alkyl or (C$_3$-C$_6$)cycloalkyl;

R$^2$ is methyl;

R$^3$ is selected from (C$_6$-C$_{10}$)branched alkyl, (C$_6$-C$_{10}$) branched alkenyl, (C$_5$-C$_8$)cycloalkenyl, (C$_5$-C$_8$)cycloalkyl, or Het; wherein the (C$_5$-C$_8$)cycloalkenyl or (C$_5$-C$_8$)cycloalkyl is unsubstituted or is substituted by one, two, three or four substituents R$^4$; and wherein Het is substituted by one, two, three or four substituents R$^4$;

each R$^4$ is independently selected from halo, (C$_1$-C$_4$)alkyl, halo(C$_1$-C$_4$)alkyl, (C$_1$-C$_4$)alkoxy, or halo(C$_1$-C$_4$) alkoxy; or two R$^4$ groups, when attached to the same carbon atom, may be taken together with the carbon atom to which they are attached to form a cyclopentyl, tetrahydrofuran or dioxolane ring; wherein Het is a 5 or 6 membered fully saturated or partially saturated heterocyclic ring comprising a) 1 oxygen atom in the 2- or 3-position, or b) 2 oxygen atoms in the 2- and 5-, or 2- and 6-positions, wherein the numbering is relative to the point of attachment; and (C$_5$-C$_8$)cycloalkyl may be a monocyclic ring or a bridged ring system containing 5, 6, 7 or 8 carbon atoms.

2. A compound according to claim 1 or a pharmaceutically acceptable salt thereof, wherein R$^1$ is iso-propyl, cyclobutyl or cyclohexyl.

3. A compound according to according to claim 1, or a pharmaceutically acceptable salt thereof, wherein R$^3$ is selected from 2,2-dimethylpentyl, 2,2-dimethylpent-2-enyl, cyclopentyl, cyclohexyl, cyclohexenyl, tetrahydropyranyl, dihydropyranyl, dioxanyl, tetrahydrofuranyl, dioxolanyl and bicyclo[2.2.2]octanyl; wherein the cyclopentyl, cyclohexyl, cyclohexenyl, tetrahydropyranyl, dihydropyranyl, dioxanyl, tetrahydrofuranyl, dioxolanyl or bicyclo[2.2.2]octanyl ring is unsubstituted or is substituted by one, two, three or four substituents R$^4$; and each R$^4$ is independently selected from halo, (C$_1$-C$_4$)alkyl, halo(C$_1$-C$_4$)alkyl, (C$_1$-C$_4$)alkoxy, or halo(C$_1$-C$_4$) alkoxy; or two R$^4$ groups, when attached to the same carbon atom, may be taken together with the carbon atom to which they are attached to form a tetrahydrofuran or dioxolane ring.

4. A compound according to according to claim 1, or a pharmaceutically acceptable salt thereof, wherein R$^3$ is

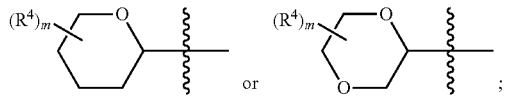

and m is 1, 2, 3 or 4.

5. A compound according to claim 1, or a pharmaceutically acceptable salt thereof, wherein each R$^4$ is independently selected from methyl, isopropyl, tert-butyl and methoxy.

6. A compound according to claim 1 which is selected from the group consisting of:

[N-(2-Cyclohexyl-1,5-dimethyl-3-oxo-2,3-dihydro-1H-pyrazol-4-yl)-5-(4-isopropylcyclohex-1-en-1-yl)-4-methylisoxazole-3-carboxamide];

N-(2-Cyclohexyl-1,5-dimethyl-3-oxo-2,3-dihydro-1H-pyrazol-4-yl)-5-(6-ethyl-4-methylcyclohex-1-en-1-yl)-4-methylisoxazole-3-carboxamide;

N-(2-Cyclohexyl-1,5-dimethyl-3-oxo-2,3-dihydro-1H-pyrazol-4-yl)-5-(6,6-dimethylcyclohex-1-en-1-yl)-4-methylisoxazole-3-carboxamide;

[N-(2-Cyclohexyl-1,5-dimethyl-3-oxo-2,3-dihydro-1H-pyrazol-4-yl)-5-(4-ethylcyclohex-1-en-1-yl)-4-methyl-isoxazole-3-carboxamide];

[5-(4-(tert-Butyl)cyclohex-1-en-1-yl)-N-(2-cyclohexyl-1,5-dimethyl-3-oxo-2,3-dihydro-1H-pyrazol-4-yl)-4-methylisoxazole-3-carboxamide];

[N-(2-Cyclohexyl-1,5-dimethyl-3-oxo-2,3-dihydro-1H-pyrazol-4-yl)-4-methyl-5-(4-methylcyclohex-1-en-1-yl)isoxazole-3-carboxamide];

5-(Cyclohept-1-en-1-yl)-N-(2-cyclohexyl-1,5-dimethyl-3-oxo-2,3-dihydro-1H-pyrazol-4-yl)-4-methylisoxazole-3-carboxamide;

[N-(2-Cyclohexyl-1,5-dimethyl-3-oxo-2,3-dihydro-1H-pyrazol-4-yl)-4-methyl-5-(4-(trifluoromethyl)cyclohex-1-en-1-yl)isoxazole-3-carboxamide];

N-(2-Cyclohexyl-1,5-dimethyl-3-oxo-2,3-dihydro-1H-pyrazol-4-yl)-4-methyl-5-(spiro[4.5]dec-7-en-8-yl) isoxazole-3-carboxamide;

[N-(2-Cyclohexyl-1,5-dimethyl-3-oxo-2,3-dihydro-1H-pyrazol-4-yl)-4-methyl-5-(1-oxaspiro[4.5]dec-7-en-8-yl)isoxazole-3-carboxamide];

N-(2-Cyclohexyl-1,5-dimethyl-3-oxo-2,3-dihydro-1H-pyrazol-4-yl)-5-(4,4-dimethylcyclohex-1-en-1-yl)-4-methylisoxazole-3-carboxamide;

N-(2-Cyclohexyl-1,5-dimethyl-3-oxo-2,3-dihydro-1H-pyrazol-4-yl)-5-(4,4-dimethylcyclopent-1-en-1-yl)-4-methylisoxazole-3-carboxamide;

[N-(2-Cyclohexyl-1,5-dimethyl-3-oxo-2,3-dihydro-1H-pyrazol-4-yl)-4-methyl-5-(2-oxaspiro[4.5]dec-7-en-8-yl)isoxazole-3-carboxamide];

[N-(2-Cyclohexyl-1,5-dimethyl-3-oxo-2,3-dihydro-1H-pyrazol-4-yl)-5-(4-isopropoxycyclohex-1-en-1-yl)-4-methylisoxazole-3-carboxamide];

N-(2-Cyclohexyl-1,5-dimethyl-3-oxo-2,3-dihydro-1H-pyrazol-4-yl)-5-(4,4-dimethylcyclohexyl)-4-methyl-isoxazole-3-carboxamide;

[N-(2-Cyclohexyl-1,5-dimethyl-3-oxo-2,3-dihydro-1H-pyrazol-4-yl)-5-(3,3-dimethylcyclopentyl)-4-methyl-isoxazole-3-carboxamide];

N-(2-Cyclohexyl-1,5-dimethyl-3-oxo-2,3-dihydro-1H-pyrazol-4-yl)-5-(3,3-dimethylbutyl)-4-methylisoxazole-3-carboxamide;

(Z)—N-(2-Cyclohexyl-1,5-dimethyl-3-oxo-2,3-dihydro-1H-pyrazol-4-yl)-5-(3,3-dimethylbut-1-en-1-yl)-4-methylisoxazole-3-carboxamide;

(E)-N-(2-Cyclohexyl-1,5-dimethyl-3-oxo-2,3-dihydro-1H-pyrazol-4-yl)-5-(3,3-dimethylbut-1-en-1-yl)-4-methylisoxazole-3-carboxamide;
5-Cyclohexyl-N-(2-cyclohexyl-1,5-dimethyl-3-oxo-2,3-dihydro-1H-pyrazol-4-yl)-4-methylisoxazole-3-carboxamide;
N-(2-Cyclohexyl-1,5-dimethyl-3-oxo-2,3-dihydro-1H-pyrazol-4-yl)-4-methyl-5-(1,4-dioxaspiro[4.5]decan-8-yl)isoxazole-3-carboxamide;
5-(6-(tert-butyl)-4-methoxytetrahydro-2H-pyran-2-yl)-N-(2-cyclohexyl-1,5-dimethyl-3-oxo-2,3-dihydro-1H-pyrazol-4-yl)-4-methylisoxazole-3-carboxamide;
5-(6-(tert-butyl)-4-methoxytetrahydro-2H-pyran-2-yl)-N-(2-cyclobutyl-1,5-dimethyl-3-oxo-2,3-dihydro-1H-pyrazol-4-yl)-4-methylisoxazole-3-carboxamide;
5-(6-(tert-butyl)tetrahydro-2H-pyran-2-yl)-N-(2-cyclobutyl-1,5-dimethyl-3-oxo-2,3-dihydro-1H-pyrazol-4-yl)-4-methylisoxazole-3-carboxamide;
5-(6-(tert-butyl)tetrahydro-2H-pyran-2-yl)-N-(2-cyclohexyl-1,5-dimethyl-3-oxo-2,3-dihydro-1H-pyrazol-4-yl)-4-methylisoxazole-3-carboxamide;
5-(6-(tert-butyl)tetrahydro-2H-pyran-2-yl)-N-(2-isopropyl-1,5-dimethyl-3-oxo-2,3-dihydro-1H-pyrazol-4-yl)-4-methylisoxazole-3-carboxamide;
N-(2-cyclohexyl-1,5-dimethyl-3-oxo-2,3-dihydro-1H-pyrazol-4-yl)-5-(6-isopropyl-3,6-dihydro-2H-pyran-2-yl)-4-methylisoxazole-3-carboxamide;
N-(2-cyclohexyl-1,5-dimethyl-3-oxo-2,3-dihydro-1H-pyrazol-4-yl)-4-methyl-5-(6-methyl-3,6-dihydro-2H-pyran-2-yl)isoxazole-3-carboxamide;
N-(2-Cyclohexyl-1,5-dimethyl-3-oxo-2,3-dihydro-1H-pyrazol-4-yl)-4-methyl-5-((2R,3S)-3,5,5-trimethyl-1,4-dioxan-2-yl)isoxazole-3-carboxamide;
[5-(4-Bromo-5-methyltetrahydro-2H-pyran-2-yl)-N-(2-cyclohexyl-1,5-dimethyl-3-oxo-2,3-dihydro-1H-pyrazol-4-yl)-4-methylisoxazole-3-carboxamide];
N-(2-cyclohexyl-1,5-dimethyl-3-oxo-2,3-dihydro-1H-pyrazol-4-yl)-4-methyl-5-(5-methyl-3,6-dihydro-2H-pyran-2-yl)isoxazole-3-carboxamide;
N-(2-cyclohexyl-1,5-dimethyl-3-oxo-2,3-dihydro-1H-pyrazol-4-yl)-4-methyl-5-(5-methyltetrahydro-2H-pyran-2-yl)isoxazole-3-carboxamide;
5-(4-(2-bromopropan-2-yl)tetrahydrofuran-2-yl)-N-(2-cyclohexyl-1,5-dimethyl-3-oxo-2,3-dihydro-1H-pyrazol-4-yl)-4-methylisoxazole-3-carboxamide;
N-(2-cyclohexyl-1,5-dimethyl-3-oxo-2,3-dihydro-1H-pyrazol-4-yl)-5-(4-isopropyltetrahydrofuran-2-yl)-4-methylisoxazole-3-carboxamide;
5-(4-(tert-butyl)-1,3-dioxolan-2-yl)-N-(2-cyclohexyl-1,5-dimethyl-3-oxo-2,3-dihydro-1H-pyrazol-4-yl)-4-methylisoxazole-3-carboxamide; and
N-(2-Cyclohexyl-1,5-dimethyl-3-oxo-2,3-dihydro-1H-pyrazol-4-yl)-5-(5,5-dimethyl-1,3-dioxan-2-yl)-4-methylisoxazole-3-carboxamide;
or a pharmaceutically acceptable salt thereof.

7. A pharmaceutical composition comprising a therapeutically effective amount of a compound according to claim 1 or a pharmaceutically acceptable salt thereof and one or more pharmaceutically acceptable carriers.

8. A combination comprising a therapeutically effective amount of a compound according to claim 1 or a pharmaceutically acceptable salt thereof and one or more therapeutically active agents.

9. A method of modulating Smurf-1 activity in a subject, wherein the method comprises administering to the subject a therapeutically effective amount of the compound according to claim 1 or a pharmaceutically acceptable salt thereof.

10. A compound which is N-(2-cyclohexyl-1,5-dimethyl-3-oxo-2,3-dihydro-1H-pyrazol-4-yl)-4-methyl-5-((2R,3S)-3,5,5-trimethyl-1,4-dioxan-2-yl)isoxazole-3-carboxamide having the following formula:

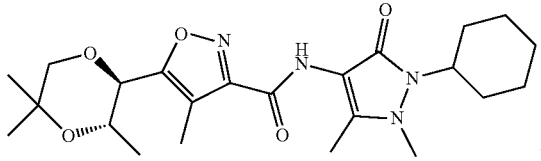

11. A compound which is N-(2-Cyclohexyl-1,5-dimethyl-3-oxo-2,3-dihydro-1H-pyrazol-4-yl)-5-(5,5-dimethyl-1,3-dioxan-2-yl)-4-methylisoxazole-3-carboxamide having the following formula:

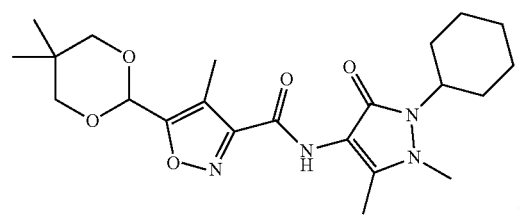

12. A compound which is 5-(6-(tert-butyl)-4-methoxytetrahydro-2H-pyran-2-yl)-N-(2-cyclohexyl-1,5-dimethyl-3-oxo-2,3-dihydro-1H-pyrazol-4-yl)-4-methylisoxazole-3-carboxamide having the following formula:

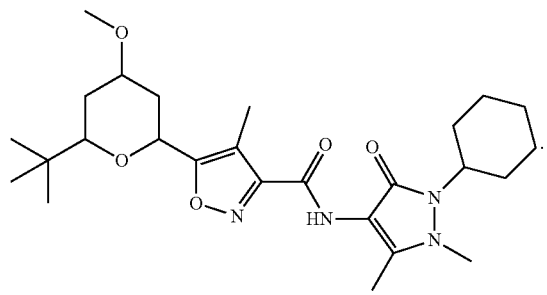 [SMILES: COC1CC(c2onc(C(=O)Nc3c(C)n(C)n(C4CCCCC4)c3=O)c2C)OC(C(C)(C)C)C1]

13. A compound which is N-(2-cyclohexyl-1,5-dimethyl-3-oxo-2,3-dihydro-1H-pyrazol-4-yl)-4-methyl-5-(6-methyl-3,6-dihydro-2H-pyran-2-yl)isoxazole-3-carboxamide having the following formula:

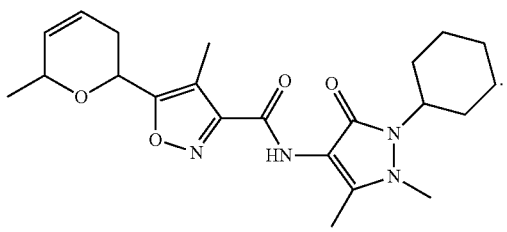 [SMILES: Cc1c(C(=O)Nc2c(C)n(C)n(C3CCCCC3)c2=O)noc1C1CC=CC(C)O1]

14. A pharmaceutical composition comprising a therapeutically effective amount of a compound according to claim 10 or a pharmaceutically acceptable salt thereof and one or more pharmaceutically acceptable carriers.

15. A pharmaceutical composition comprising a therapeutically effective amount of a compound according to claim 11 or a pharmaceutically acceptable salt thereof and one or more pharmaceutically acceptable carriers.

16. A pharmaceutical composition comprising a therapeutically effective amount of a compound according to claim 12 or a pharmaceutically acceptable salt thereof and one or more pharmaceutically acceptable carriers.

17. A pharmaceutical composition comprising a therapeutically effective amount of a compound according to claim 13 or a pharmaceutically acceptable salt thereof and one or more pharmaceutically acceptable carriers.

* * * * *